(12) United States Patent
Kohn et al.

(10) Patent No.: US 11,976,293 B2
(45) Date of Patent: May 7, 2024

(54) OPTIMIZED LENTIVIRAL VECTOR FOR STEM CELL GENE THERAPY OF HEMOGLOBINOPATHIES

(71) Applicant: The Regents of the University of California, Oakland, CA (US)

(72) Inventors: Donald B. Kohn, Tarzana, CA (US); Richard A. Morgan, Los Angeles, CA (US); Roger P. Hollis, Los Angeles, CA (US)

(73) Assignee: THE REGENTS OF THE UNIVERSITY OF CALIFORNIA, Oakland, CA (US)

( * ) Notice: Subject to any disclaimer, the term of this patent is extended or adjusted under 35 U.S.C. 154(b) by 707 days.

(21) Appl. No.: 16/466,970

(22) PCT Filed: Dec. 5, 2017

(86) PCT No.: PCT/US2017/064766
§ 371 (c)(1),
(2) Date: Jun. 5, 2019

(87) PCT Pub. No.: WO2018/106724
PCT Pub. Date: Jun. 14, 2018

(65) Prior Publication Data
US 2020/0109416 A1   Apr. 9, 2020

Related U.S. Application Data

(60) Provisional application No. 62/430,157, filed on Dec. 5, 2016.

(51) Int. Cl.
| | | |
|---|---|---|
| *C12N 15/86* | (2006.01) | |
| *A61K 35/28* | (2015.01) | |
| *A61K 48/00* | (2006.01) | |
| *A61P 7/00* | (2006.01) | |
| *C12N 7/00* | (2006.01) | |

(52) U.S. Cl.
CPC ............. *C12N 15/86* (2013.01); *A61K 35/28* (2013.01); *A61K 48/005* (2013.01); *A61P 7/00* (2018.01); *C12N 7/00* (2013.01); *C12N 2740/15043* (2013.01)

(58) Field of Classification Search
CPC ................. C12N 15/86; C12N 7/00; C12N 2740/15043; C12N 2740/16043; C12N 15/63; A61K 35/28; A61K 48/005; A61P 7/00
See application file for complete search history.

(56) References Cited

U.S. PATENT DOCUMENTS

| 11,203,768 B2 | 12/2021 | Uchida et al. |
|---|---|---|
| 2008/0069805 A1 | 3/2008 | Williams |
| 2015/0224209 A1 * | 8/2015 | Kohn .............. A61P 7/06 435/372.3 |
| 2017/0173185 A1 * | 6/2017 | Sadelain ........... A61K 48/0058 |
| 2019/0038775 A1 | 2/2019 | Leboulch et al. |

FOREIGN PATENT DOCUMENTS

| WO | WO 2013/173599 A1 | 11/2013 |
|---|---|---|
| WO | WO 2014/043131 A1 | 3/2014 |
| WO | WO 2016/037138 A1 | 3/2016 |
| WO | WO 2016/118715 A1 | 7/2016 |

OTHER PUBLICATIONS

PCT International Search Report and Written Opinion dated Mar. 19, 2018 issued in PCT/US2017/064766.
PCT International Preliminary Search Report on Patentability dated Jun. 11, 2019 issued in PCT/US2017/064766.
European Extended Search Report dated May 20, 2020 issued in EP 17878597.8.
Hoban et al. (2016) "Genetic treatment of a molecular disorder: gene therapy approaches to sickle cell disease," *Blood*, 127(7): 839-848.
Lisowski et al. (2008) "Current status of globin gene therapy for the treatment of β-thalassaemia" *British Journal of Haematology*, 141(3): 335-345.
Miccio et al. (2008) "In vivo selection of genetically modified erythrobalistic progenitors leads to long-term correction of—thalassemia" *Proc. Natl. Acad. Sci. USA*, 105(30): 10547-10552.
Negre et al. (2016) "Gene Therapy of the β-Hemoglobinopathies by Lentiviral Transfer of the $β^{A(T87Q)}$-Globin Gene" *Human Gene Therapy*, 27(2): 148-165.
Romero et al. (2013) "β-globin gene transfer to human bone marrow for sickle cell disease" *J. Clin. Invest.*, 128(8): 3317-3330.
Sadelain et al. (2004) "Globin gene transfer for treatment of the β-thalassemias and sickle cell disease," *Best Practice & Research Clinical Haematology*, 17(3): 517-534.
Levasseur, D.N., et al., "Correction of a Mouse Model of Sickle Cell Disease: Lentiviral/antisickling Beta-globin Gene Transduction of Unmobilized, Purified Hematopoietic Stem Cells", Blood, 2003, vol. 102(13), pp. 4312-4319.
European Office Action dated Nov. 9, 2022 in Application No. EP17878597.8.

* cited by examiner

*Primary Examiner* — Janet L Epps-Smith
*Assistant Examiner* — Alexander W Nicol
(74) *Attorney, Agent, or Firm* — Mark S. Cohen; PEARL COHEN ZEDEK LATZER BARATZ LLP

(57) ABSTRACT

In certain embodiments an optimized derivative of the CCLc-βAS3-FB lentiviral vector termed (CCLc-mGata/ANK-CoreLCR-βAS3-FB), is provided which is capable of driving lineage-restricted expression of a beta-globin gene (e.g., an anti-sickling β-globin like gene (βA83)). In certain embodiments the vectors described herein comprise novel defined LCR HS core sequences (HS2(~420 bp), HS3β40 bp), HS4(~410 bp)) which can be used to replace the putative LCR HS sequences present within the "mini-LCR" (~3.6 kb reduced to ~1.2 kb) to produce an "optimized mini-LCR".

12 Claims, 37 Drawing Sheets

Specification includes a Sequence Listing.

From Junction Marker:
ATTTTTACGGTTCCTGGCCTTTTGCTGGCCTTTTGCTCACATGTTCTTTCCTGCGTTATCC
CCTGATTCTGTGGATAACCGTATTACCGCCTTTGAGTGAGCTGATACCGCTCGCCGCAGCC
GAACGACCGAGCGCAGCGAGTCAGTGAGCGAGGAAGCGGAAGAGCGCCCAATACGCAAACC
GCCTCTCCCCGCGCGTTGGCCGATTCATTAATGCAGCTGGCACGACAGGTTTCCCGACTGG
AAAGCGGGCAGTGAGCGCAACGCAATTAATGTGAGTTAGCTCACTCATTAGGCACCCCAGG
CTTTACACTTTATGCTTCCGGCTCGTATGTTGTGTGGAATTGTGAGCGGATAACAATTTCA
CACAGGAAACAGCTATGACCATGATTACGCCAAGCGCGCAATTAACCCTCACTAAAGGGAA
CAAAAGCTGGAGCTGCAAGCTTGGCCATTGCATACGTTGTATCCATATCATAATATGTACA
TTTATATTGGCTCATGTCCAACATTACCGCCATGTTGACATTGATTATTGACTAGTTATTA
ATAGTAATCAATTACGGGGTCATTAGTTCATAGCCCATATATGGAGTTCCGCGTTACATAA
CTTACGGTAAATGGCCCGCCTGGCTGACCGCCCAACGACCCCCGCCCATTGACGTCAATAA
TGACGTATGTTCCCATAGTAACGCCAATAGGGACTTTCCATTGACGTCAATGGGTGGAGTA
TTTACGGTAAACTGCCCACTTGGCAGTACATCAAGTGTATCATATGCCAAGTACGCCCCCT
ATTGACGTCAATGACGGTAAATGGCCCGCCTGGCATTATGCCCAGTACATGACCTTATGGG
ACTTTCCTACTTGGCAGTACATCTACGTATTAGTCATCGCTATTACCATGGTGATGCGGTT
TTGGCAGTACATCAATGGGCGTGGATAGCGGTTTGACTCACGGGGATTTCCAAGTCTCCAC
CCCATTGACGTCAATGGGAGTTTGTTTTGGCACCAAAATCAACGGGACTTTCCAAAATGTC
GTAACAACTCCGCCCCATTGACGCAAATGGGCGGTAGGCGTGTACGGTGGGAGGTCTATAT
AAGCAGAGCTCGTTTAGTGAACCGGGGTCTCTCTGGTTAGACCAGATCTGAGCCTGGGAGC
TCTCTGGCTAACTAGGGAACCCACTGCTTAAGCCTCAATAAAGCTTGCCTTGAGTGCTTCA
AGTAGTGTGTGCCCGTCTGTTGTGTGACTCTGGTAACTAGAGATCCCTCAGACCCTTTTAG
TCAGTGTGGAAAATCTCTAGCAGTGGCGCCCGAACAGGGACTTGAAAGCGAAAGGGAAACC
AGAGGAGCTCTCTCGACGCAGGACTCGGCTTGCTGAAGCGCGCACGGCAAGAGGCGAGGGG
CGGCGACTGGTGAGTACGCCAAAAATTTTGACTAGCGGAGGCTAGAAGGAGAGAGATGGGT
GCGAGAGCGTCAGTATTAAGCGGGGAGAATTAGATCGCGATGGGAAAAAATTCGGTTAAG
GCCAGGGGGAAAGAAAAAATATAAATTAAAACATATAGTATGGGCAAGCAGGGAGCTAGAA
CGATTCGCAGTTAATCCTGGCCTGTTAGAAACATCAGAAGGCTGTAGACAAATACTGGGAC
AGCTACAACCATCCCTTCAGACAGGATCAGAAGAACTTAGATCATTATATAATACAGTAGC
AACCCTCTATTGTGTGCATCAAAGGATAGAGATAAAAGACACCAAGGAAGCTTTAGACAAG
ATAGAGGAAGAGCAAAACAAAAGTAAGACCACCGCACAGCAAGCGGCCGCTGATCTTCAGA
CCTGGAGGAGGAGATATGAGGGACAATTGGAGAAGTGAATTATATAAATATAAAGTAGTAA
AAATTGAACCATTAGGAGTAGCACCCACCAAGGCAAAGAGAAGAGTGGTGCAGAGAGAAAA
AAGAGCAGTGGGAATAGGAGCTTTGTTCCTTGGGTTCTTGGGAGCAGCAGGAAGCACTATG
GGCGCAGCGTCAATGACGCTGACGGTACAGGCCAGACAATTATTGTCTGGTATAGTGCAGC
AGCAGAACAATTTGCTGAGGGCTATTGAGGCGCAACAGCATCTGTTGCAACTCACAGTCTG
GGGCATCAAGCAGCTCCAGGCAAGAATCCTGGCTGTGGAAAGATACCTAAAGGATCAACAG
CTCCTGGGGATTTGGGGTTGCTCTGGAAAACTCATTTGCACCACTGCTGTGCCTTGGAATG
CTAGTTGGAGTAATAAATCTCTGGAACAGATTTGGAATCACACGACCTGGATGGAGTGGGA
CAGAGAAATTAACAATTACACAAGCTTAATACACTCCTTAATTGAAGAATCGCAAAACCAG
CAAGAAAAGAATGAACAAGAATTATTGGAATTAGATAAATGGGCAAGTTTGTGGAATTGGT
TTAACATAACAAATTGGCTGTGGTATATAAAATTATTCATAATGATAGTAGGAGGCTTGGT

Fig. 15B

```
AGGTTTAAGAATAGTTTTTGCTGTACTTTCTATAGTGAATAGAGTTAGGCAGGGATATTCA
CCATTATCGTTTCAGACCCACCTCCCAACCCCGAGGGGACCCGACAGGCCCGAAGGAATAG
AAGAAGAAGGTGGAGAGAGAGACAGAGACAGATCCATTCGATTAGTGAACGGATCTCGACG
GTATCGATCTCGACACAAATGGCAGTATTCATCCACAATTTTAAAAGAAAAGGGGGGATTG
GGGGGTACAGTGCAGGGAAAGAATAGTAGACATAATAGCAACAGACATACAAACTAAAGA
ATTACAAAAACAAATTACAAAAATTCAAAATTTTCGGGTTTATTACAGGGACAGCAGAGAT
CCAGTTTGGGTCGAGGATATCGGATCGGAATTCTCTAGATGATCAGGATCCCTCGAGCCCT
TATCGATCACGAGACTAGCCTCGACTACTAGTGGAGATCCCCGGGCTGCAGAGCCAGAAG
CACCATAAGGGACATGATAAGGGAGCCAGCAGACCTCTGATCTCTTCCTGAATGCTAATCT
TAAACATCCTGAGGAAGAATGGGACTTCCATTTGGGGTGGGCCTATGATAGGGTAATAAGA
CAGTAGTGAATATCAAGCTACAAAAAGCCCCCTTTCAAATTCTTCTCAGTCCTAACTTTTC
ATACTAAGCCCAGTCCTTCCAAAGCAGACTGTGAAAGAGTGATAGTTCCGGGAGACTAGCA
CTGCAGATTCCGGGTCACTGTGAGTGGGGAGGCAGGGAAGAAGGGCTCACAGGACAGTCA
AACCATGCCCCTGTTTTTCCTTCTTCAAGTAGACCTCTATAAGACAACAGAGACAACTAA
GGCTGAGTGGCCAGGCGAGGAGAAACCATCTCGCCGTAAAACATGGAAGGAACACTTCAGG
GGAAAGGTGGTATCTCTAAGCAAGAGAACTGAGTGGAGTCAAGGCTGAGAGATGCAGGATA
AGCAAATGGGTAGTGAAAGACATTCATGAGGACAGCTAAAACAATAAGTAATGTAAAATA
CAGCATAGCAAAACTTTAACCTCCAAATCAAGCCTCTACTTGAATCCTTTTCTGAGGGATG
AATAAGGCATAGGCATCAGGGGCTGTTGCCAATGTGCATTAGCTGTTTGCAGCCTCACCTT
CTTTCATGGAGTTTAAGATATAGTGTATTTTCCCAAGGTTTGAACTAGCTCTTCATTTCTT
TATGTTTTAAATGCACTGACCTCCCACATTCCCTTTTTAGTAAAATATTCAGAAATAATTT
AAATACATCATTGCAATGAAAATAAATGTTTTTTATTAGGCAGAATCCAGATGCTCAAGGC
CCTTCATAATATCCCCAGTTTAGTAGTTGGACTTAGGGAACAAAGGAACCTTTAATAGAA
ATTGGACAGCAAGAAAGCGAGCTTAGTGATACTTGTGGGCCAGGGCATTAGCCACACCAGC
CACCACTTTCTGATAGGCAGCCTGCACTGGTGGGGTGAATTCTTTGCCAAAGTGATGGGCC
AGCACACAGACCAGCACGTTGCCCAGGAGCTGTGGGAGGAAGATAAGAGGTATGAACATGA
TTAGCAAAAGGGCCTAGCTTGGACTCAGAATAATCCAGCCTTATCCCAACCATAAAATAAA
AGCAGAATGGTAGCTGGATTGTAGCTGCTATTAGCAATATGAAACCTCTTACATCAGTTAC
AATTTATATGCAGAAATATTTATATGCAGAAATATTGCTATTGCCTTAACCCAGAAATTAT
CACTGTTATTCTTTAGAATGGTGCAAAGAGGCATGATACATTGTATCATTATTGCCCTGAA
AGAAAGAGATTAGGGAAAGTATTAGAAATAAGATAAACAAAAAGTATATTAAAAGAAGAA
AGCATTTTTTAAAATTACAAATGCAAAATTACCCTGATTTGGTCAATATGTGTACCCTGTT
ACTTCTCCCCTTCCTATGACATGAACTTAACCATAGAAAAGAAGGGGAAAGAAAACATCAA
GGGTCCCATAGACTCACCCTGAAGTTCTCAGGATCCACGTGCAGCTTGTCACAGTGCAGCT
CACTCAGCTGGGCAAAGGTGCCCTTGAGGTTGTCCAGGTGAGCCAGGCCATCACTAAAGGC
ACCGAGCACTTTCTTGCCATGAGCCTTCACCTTAGGGTTGCCCATAACAGCATCAGGAGTG
GACAGATCCCCAAAGGACTCAAAGAACCTCTGGGTCCAAGGGTAGACCACCAGCAGCCTAA
GGGTGGGAAAATAGACCAATAGGCAGAGAGAGTCAGTGCCTATCAGAAACCCAAGAGTCTT
CTCTGTCTCCACATGCCCAGTTTCTATTGGTCTCCTTAAACCTGTCTTGTAACCTTGATAC
```

*Fig. 15B, cont'd.*

```
CAACCTGCCCAGGGCCTCACCACCAACGGCATCCACGTTCACCTTGTCCCACAGGGCAGTA
ACGGCAGACTTCTCCTCAGGAGTCAGGTGCACCATGGTGTCTGTTTGAGGTTGCTAGTGAA
CACAGTTGTGTCAGAAGCAAATGTAAGCAATAGATGGCTCTGCCCTGACTTTTATGCCCAG
CCCTGGCTCCTGCCCTCCCTGCTCCTGGGAGTAGATTGGCCAACCCTAGGGTGTGGCTCCA
CAGGGTGAGGTCTAAGTGATGACAGCCGTACCTGTCCTTGGCTCTTCTGGCACTGGCTTAG
GAGTTGGACTTCAAACCCTCAGCCCTCCCTCTAAGATATATCTCTTGGCCCCATACCATCA
GTACAAATTGCTACTAAAAACATCCTCCTTTGCAAGTGTATTTACCCGACGCGTCGGCGAT
AAGCTTGATCCATCGATGACGTGCGGGCCAGGCCCCGAGGGCCTTAACGGCCCAGAGGC
GCTTGCTGTCGGGCCGGGCGCTCCCGGCACGGGCGGGCGGAGGGGTGGCGCCCGCCTGGGG
ACCGCAGATTACAAGAGCACCTCCTCCCCAACCCCAGGAGGCCCCGCTCCCCATACGTAT
ATGTGTATATATATATATATTCAGGAAATAATATATTCTAGAATATGTCACATTCTGTC
TCAGGCATCCATTTTCTTTATGATGCCGTTTGAGGTGGAGTTTTAGTCAGGTGGTCAGCTT
CTCCTTTTTTTTGCCATCTGCCCTGTAAGCATCCTGCTGGGGACCCAGATAGGAGTCATCA
CTCTAGGCTGAGAACATCTGGGCACACACCCTAAGCCTCAGCATGACTCATCATGACTCAG
CATTGCTGTGCTTGAGCCAGAAGGTTTGCTTAGAAGGTTACACAGAACCAGAAGGCGGGGG
TGGGGCACTGACCCCGACAGGGGCCTGGCCAGAACTGCTCATGCTTGGACTATGGGAGGTC
ACTAATGGAGACACACAGAAATGTAACAGGAACTAAGGAAAAACTGAAGCTTTGGGGGTAT
AGGGGAGCAGTCCCATGTAGTAGTAGAATGAAAAATGCTGCTATGCTGTGCCTCCCCACC
TTTCCCATGTCTGCCCTCTACTCATGGTCTATCTCTCCTGGCTCCTGGGAGTCATGGACTC
CACCCAGCACCACCAACCTGACCTAACCACCTATCTGAGCCTGCCAGCCTATAACCCATCT
GGGCCCTGATAGCTGGTGGCCAGCCCTGACCCCACCCCACCCTCCCTGGAACCTCTGATAG
ACACATCTGGCACACCAGCTCGCAAAGTCACCGTGAGGGTCTTGTGTTTGCTGAGTCAAAA
TTCCTTGAAATCCAAGTCCTTAGAGACTCCCAGGCTTGGATTCAAAGCTCCTGACTTTCTG
TCTAGTGTATGTGCAGTGAGCCCCTTTTCCTCTAACTGAAAGAAGGAAAAAAAAATGGAAC
CCAAAATATTCTACATAGTTTCCATGTCACAGCCAGGGCTGGGCAGTCTCCTGTTATTTCT
TTTAAAATAAATATATCATTTAAATGCATAAATAAGCAAACCCTGCTCGGGAATGGGAGGG
AGAGTCTCTGGAGTCCACCCCTTCTCGGCCCTGGCTCTGCAGATAGTGCTATCAAAGCCCT
GACAGAGCCCTGCCCATTGCTGGGCCTTGGAGTGAGTCAGCCTAGTAGAGAGGCAGGGCAA
GCCATCTCATAGCTGCTGAGTGGGAGAGAGAAAAGGGCTCATTGTCTATAAACTCAGGTCA
TGGCTATTCTTATGGCCTACTCGACCACGAGGGAATTCCGATAATCAACCTCTGGATTACA
AAATTTGTGAAAGATTGACTGGTATTCTTAACTATGTTGCTCCTTTTACGCTATGTGGATA
CGCTGCTTTAATGCCTTTGTATCATGCTATTGCTTCCCGTATGGCTTTCATTTTCTCCTCC
TTGTATAAATCCTGGTTGCTGTCTCTTTATGAGGAGTTGTGGCCCGTTGTCAGGCAACGTG
GCGTGGTGTGCACTGTGTTTGCTGACGCAACCCCCACTGGTTGGGGCATTGCCACCACCTG
TCAGCTCCTTTCCGGGACTTTCGCTTTCCCCCTCCCTATTGCCACGGCGGAACTCATCGCC
GCCTGCCTTGCCCGCTGCTGGACAGGGGCTCGGCTGTTGGGCACTGACAATTCCGTGGTGT
TGTCGGGGAAATCATCGTCCTTTCCTTGGCTGCTCGCCTGTGTTGCCACCTGGATTCTGCG
CGGGACGTCCTTCTGCTACGTCCCTTCGGCCCTCAATCCAGCGGACCTTCCTTCCCGCGG
CTGCTGCCGGCTCTGCGGCCTCTTCCGCGTCTTCGCCTTCGCCCTCAGACGAGTCGGATCT
CCCTTTGGGCCGCCTCCCCGCATCGATACCGTCGACCTCGAGACCTAGAAAAACATGGCCA
ATTCGAGCTCGGTACCTTTAAGACCAATGACTTACAAGGCAGCTGTAGATCTTAGCCACTT
```

*Fig. 15B, cont'd.*

```
TTTAAAAGAAAAGGGGGGACTGGAAGGGCTAATTCACTCCCAACGAAGACAAGATCCCAGG
GATGTACGTCCCTAACCCGCTAGGGGGCAGCACCCAGGCCTGCACTGCCGCCTGCCGGCAG
GGGTCCAGTCCTGCTTTTTGCTTGTACTGGGTCTCTCTGGTTAGACCAGATCTGAGCCTGG
GAGCTCTCTGGCTAACTAGGGAACCCACTGCTTAAGCCTCAATAAAGCTTGCCTTGAGTGC
TTCAAGTAGTGTGTGCCCGTCTGTTGTGTGACTCTGGTAACTAGAGATCCCTCAGACCCTT
TTAGTCAGTGTGGAAAATCTCTAGCAGTAGTAGTTCATGTCATCTTATTATTCAGTATTTA
TAACTTGCAAAGAAATGAATATCAGAGAGTGAGAGGAACTTGTTTATTGCAGCTTATAATG
GTTACAAATAAAGCAATAGCATCACAAATTTCACAAATAAAGCATTTTTTCACTGCATTC
TAGTTGTGGTTTGTCCAAACTCATCAATGTATCTTATCATGTCTGGCTCTAGCTATCCCGC
CCCTAACTCCGCCCATCCCGCCCCTAACTCCGCCCAGTTCCGCCCATTCTCCGCCCCATGG
CTGACTAATTTTTTTATTTATGCAGAGGCCGAGGCCGCCTCGGCCTCTGAGCTATTCCAG
AAGTAGTGAGGAGGCTTTTTTGGAGGCCTAGGCTTTTGCGTCGAGACGTACCCAATTCGCC
CTATAGTGAGTCGTATTACGCGCGCTCACTGGCCGTCGTTTTACAACGTCGTGACTGGGAA
AACCCTGGCGTTACCCAACTTAATCGCCTTGCAGCACATCCCCCTTTCGCCAGCTGGCGTA
ATAGCGAAGAGGCCCGCACCGATCGCCCTTCCCAACAGTTGCGCAGCCTGAATGGCGAATG
GCGCGACGCGCCCTGTAGCGGCGCATTAAGCGCGGCGGGTGTGGTGGTTACGCGCAGCGTG
ACCGCTACACTTGCCAGCGCCCTAGCGCCCGCTCCTTTCGCTTTCTTCCCTTCCTTTCTCG
CCACGTTCGCCGGCTTTCCCCGTCAAGCTCTAAATCGGGGGCTCCCTTTAGGGTTCCGATT
TAGTGCTTTACGGCACCTCGACCCCAAAAAACTTGATTAGGGTGATGGTTCACGTAGTGGG
CCATCGCCCTGATAGACGGTTTTTCGCCCTTTGACGTTGGAGTCCACGTTCTTTAATAGTG
GACTCTTGTTCCAAACTGGAACAACACTCAACCCTATCTCGGTCTATTCTTTTGATTTATA
AGGGATTTTGCCGATTTCGGCCTATTGGTTAAAAAATGAGCTGATTTAACAAAAATTTAAC
GCGAATTTTAACAAATATTAACGTTTACAATTTCCCAGGTGGCACTTTTCGGGGAAATGT
GCGCGGAACCCCTATTTGTTTATTTTTCTAAATACATTCAAATATGTATCCGCTCATGAGA
CAATAACCCTGATAAATGCTTCAATAATATTGAAAAAGGAAGAGTATGAGTATTCAACATT
TCCGTGTCGCCCTTATTCCCTTTTTTGCGGCATTTTGCCTTCCTGTTTTTGCTCACCCAGA
AACGCTGGTGAAAGTAAAAGATGCTGAAGATCAGTTGGGTGCACGAGTGGGTTACATCGAA
CTGGATCTCAACAGCGGTAAGATCCTTGAGAGTTTTCGCCCCGAAGAACGTTTTCCAATGA
TGAGCACTTTTAAAGTTCTGCTATGTGGCGCGGTATTATCCCGTATTGACGCCGGGCAAGA
GCAACTCGGTCGCCGCATACACTATTCTCAGAATGACTTGGTTGAGTACTCACCAGTCACA
GAAAAGCATCTTACGGATGGCATGACAGTAAGAGAATTATGCAGTGCTGCCATAACCATGA
GTGATAACACTGCGGCCAACTTACTTCTGACAACGATCGGAGGACCGAAGGAGCTAACCGC
TTTTTTGCACAACATGGGGGATCATGTAACTCGCCTTGATCGTTGGGAACCGGAGCTGAAT
GAAGCCATACCAAACGACGAGCGTGACACCACGATGCCTGTAGCAATGGCAACAACGTTGC
GCAAACTATTAACTGGCGAACTACTTACTCTAGCTTCCCGGCAACAATTAATAGACTGGAT
GGAGGCGGATAAAGTTGCAGGACCACTTCTGCGCTCGGCCCTTCCGGCTGGCTGGTTTATT
GCTGATAAATCTGGAGCCGGTGAGCGTGGGTCTCGCGGTATCATTGCAGCACTGGGGCCAG
ATGGTAAGCCCTCCCGTATCGTAGTTATCTACACGACGGGGAGTCAGGCAACTATGGATGA
ACGAAATAGACAGATCGCTGAGATAGGTGCCTCACTGATTAAGCATTGGTAACTGTCAGAC
```

*Fig. 15B, cont'd.*

```
CAAGTTTACTCATATATACTTTAGATTGATTTAAAACTTCATTTTTAATTTAAAAGGATCT
AGGTGAAGATCCTTTTTGATAATCTCATGACCAAAATCCCTTAACGTGAGTTTTCGTTCCA
CTGAGCGTCAGACCCCGTAGAAAAGATCAAAGGATCTTCTTGAGATCCTTTTTTTCTGCGC
GTAATCTGCTGCTTGCAAACAAAAAAACCACCGCTACCAGCGGTGGTTTGTTTGCCGGATC
AAGAGCTACCAACTCTTTTTCCGAAGGTAACTGGCTTCAGCAGAGCGCAGATACCAAATAC
TGTCCTTCTAGTGTAGCCGTAGTTAGGCCACCACTTCAAGAACTCTGTAGCACCGCCTACA
TACCTCGCTCTGCTAATCCTGTTACCAGTGGCTGCTGCCAGTGGCGATAAGTCGTGTCTTA
CCGGGTTGGACTCAAGACGATAGTTACCGGATAAGGCGCAGCGGTCGGGCTGAACGGGGGG
TTCGTGCACACAGCCCAGCTTGGAGCGAACGACCTACACCGAACTGAGATACCTACAGCGT
GAGCTATGAGAAAGCGCCACGCTTCCCGAAGGGAGAAAGGCGGACAGGTATCCGGTAAGCG
GCAGGGTCGGAACAGGAGAGCGCACGAGGGAGCTTCCAGGGGGAAACGCCTGGTATCTTTA
TAGTCCTGTCGGGTTTCGCCACCTCTGACTTGAGCGTCGATTTTTGTGATGCTCGTCAGGG
GGGCGGAGCCTATGGAAAAACGCCAGCAACGCGGCC
```

*Fig. 15B, cont'd.*

From Junction Marker:
ATTTTTACGGTTCCTGGCCTTTTGCTGGCCTTTTGCTCACATGTTCTTTCCTGCGTTATCC
CCTGATTCTGTGGATAACCGTATTACCGCCTTTGAGTGAGCTGATACCGCTCGCCGCAGCC
GAACGACCGAGCGCAGCGAGTCAGTGAGCGAGGAAGCGGAAGAGCGCCCAATACGCAAACC
GCCTCTCCCCGCGCGTTGGCCGATTCATTAATGCAGCTGGCACGACAGGTTTCCCGACTGG
AAAGCGGGCAGTGAGCGCAACGCAATTAATGTGAGTTAGCTCACTCATTAGGCACCCCAGG
CTTTACACTTTATGCTTCCGGCTCGTATGTTGTGTGGAATTGTGAGCGGATAACAATTTCA
CACAGGAAACAGCTATGACCATGATTACGCCAAGCGCGCAATTAACCCTCACTAAAGGGAA
CAAAAGCTGGAGCTGCAAGCTTGGCCATTGCATACGTTGTATCCATATCATAATATGTACA
TTTATATTGGCTCATGTCCAACATTACCGCCATGTTGACATTGATTATTGACTAGTTATTA
ATAGTAATCAATTACGGGGTCATTAGTTCATAGCCCATATATGGAGTTCCGCGTTACATAA
CTTACGGTAAATGGCCCGCCTGGCTGACCGCCCAACGACCCCGCCCATTGACGTCAATAA
TGACGTATGTTCCCATAGTAACGCCAATAGGGACTTTCCATTGACGTCAATGGGTGGAGTA
TTTACGGTAAACTGCCCACTTGGCAGTACATCAAGTGTATCATATGCCAAGTACGCCCCCT
ATTGACGTCAATGACGGTAAATGGCCCGCCTGGCATTATGCCCAGTACATGACCTTATGGG
ACTTTCCTACTTGGCAGTACATCTACGTATTAGTCATCGCTATTACCATGGTGATGCGGTT
TTGGCAGTACATCAATGGGCGTGGATAGCGGTTTGACTCACGGGGATTTCCAAGTCTCCAC
CCCATTGACGTCAATGGGAGTTTGTTTTGGCACCAAAATCAACGGGACTTTCCAAAATGTC
GTAACAACTCCGCCCCATTGACGCAAATGGGCGGTAGGCGTGTACGGTGGGAGGTCTATAT
AAGCAGAGCTCGTTTAGTGAACCGGGGTCTCTCTGGTTAGACCAGATCTGAGCCTGGGAGC
TCTCTGGCTAACTAGGGAACCCACTGCTTAAGCCTCAATAAAGCTTGCCTTGAGTGCTTCA
AGTAGTGTGTGCCCGTCTGTTGTGTGACTCTGGTAACTAGAGATCCCTCAGACCCTTTTAG
TCAGTGTGGAAAATCTCTAGCAGTGGCGCCCGAACAGGGACTTGAAAGCGAAAGGGAAACC
AGAGGAGCTCTCTCGACGCAGGACTCGGCTTGCTGAAGCGCGCACGGCAAGAGGCGAGGGG
CGGCGACTGGTGAGTACGCCAAAAATTTTGACTAGCGGAGGCTAGAAGGAGAGAGATGGGT
GCGAGAGCGTCAGTATTAAGCGGGGGAGAATTAGATCGCGATGGGAAAAAATTCGGTTAAG
GCCAGGGGGAAAGAAAAAATATAAATTAAAACATATAGTATGGGCAAGCAGGGAGCTAGAA
CGATTCGCAGTTAATCCTGGCCTGTTAGAAACATCAGAAGGCTGTAGACAAATACTGGGAC
AGCTACAACCATCCCTTCAGACAGGATCAGAAGAACTTAGATCATTATATAATACAGTAGC
AACCCTCTATTGTGTGCATCAAAGGATAGAGATAAAAGACACCAAGGAAGCTTTAGACAAG
ATAGAGGAAGAGCAAAACAAAAGTAAGACCACCGCACAGCAAGCGGCCGCTGATCTTCAGA
CCTGGAGGAGGAGATATGAGGGACAATTGGAGAAGTGAATTATATAAATATAAAGTAGTAA
AAATTGAACCATTAGGAGTAGCACCCACCAAGGCAAAGAGAAGAGTGGTGCAGAGAGAAAA
AAGAGCAGTGGGAATAGGAGCTTTGTTCCTTGGGTTCTTGGGAGCAGCAGGAAGCACTATG
GGCGCAGCGTCAATGACGCTGACGGTACAGGCCAGACAATTATTGTCTGGTATAGTGCAGC
AGCAGAACAATTTGCTGAGGGCTATTGAGGCGCAACAGCATCTGTTGCAACTCACAGTCTG
GGGCATCAAGCAGCTCCAGGCAAGAATCCTGGCTGTGGAAAGATACCTAAAGGATCAACAG
CTCCTGGGGATTTGGGGTTGCTCTGGAAAACTCATTTGCACCACTGCTGTGCCTTGGAATG
CTAGTTGGAGTAATAAATCTCTGGAACAGATTTGGAATCACACGACCTGGATGGAGTGGGA
CAGAGAAATTAACAATTACACAAGCTTAATACACTCCTTAATTGAAGAATCGCAAAACCAG
CAAGAAAAGAATGAACAAGAATTATTGGAATTAGATAAATGGGCAAGTTTGTGGAATTGGT

*Fig. 16B*

```
TTAACATAACAAATTGGCTGTGGTATATAAAATTATTCATAATGATAGTAGGAGGCTTGGT
AGGTTTAAGAATAGTTTTTGCTGTACTTTCTATAGTGAATAGAGTTAGGCAGGGATATTCA
CCATTATCGTTTCAGACCCACCTCCCAACCCCGAGGGGACCCGACAGGCCCGAAGGAATAG
AAGAAGAAGGTGGAGAGAGAGACAGAGACAGATCCATTCGATTAGTGAACGGATCTCGACG
GTATCGATCTCGACACAAATGGCAGTATTCATCCACAATTTTAAAAGAAAAGGGGGGATTG
GGGGGTACAGTGCAGGGGAAAGAATAGTAGACATAATAGCAACAGACATACAAACTAAAGA
ATTACAAAAACAAATTACAAAAATTCAAAATTTTCGGGTTTATTACAGGGACAGCAGAGAT
CCAGTTTGGGTCGAGGATATCGGATCGGAATTCTCTAGATGATCAGGATCCCTCGAGCCCT
TATCGATCACGAGACTAGCCTCGACTACTAGTGGAGATCCCCCGGGCTGCAGAGCCAGAAG
CACCATAAGGGACATGATAAGGGAGCCAGCAGACCTCTGATCTCTTCCTGAATGCTAATCT
TAAACATCCTGAGGAAGAATGGGACTTCCATTTGGGGTGGGCCTATGATAGGGTAATAAGA
CAGTAGTGAATATCAAGCTACAAAAAGCCCCTTTCAAATTCTTCTCAGTCCTAACTTTTC
ATACTAAGCCCAGTCCTTCCAAAGCAGACTGTGAAAGAGTGATAGTTCCGGGAGACTAGCA
CTGCAGATTCCGGGTCACTGTGAGTGGGGAGGCAGGGAAGAAGGGCTCACAGGACAGTCA
AACCATGCCCCTGTTTTTCCTTCTTCAAGTAGACCTCTATAAGACAACAGAGACAACTAA
GGCTGAGTGGCCAGGCGAGGAGAAACCATCTCGCCGTAAAACATGGAAGGAACACTTCAGG
GGAAAGGTGGTATCTCTAAGCAAGAGAACTGAGTGGAGTCAAGGCTGAGAGATGCAGGATA
AGCAAATGGGTAGTGAAAGACATTCATGAGGACAGCTAAAACAATAAGTAATGTAAAATA
CAGCATAGCAAAACTTTAACCTCCAAATCAAGCCTCTACTTGAATCCTTTTCTGAGGGATG
AATAAGGCATAGGCATCAGGGGCTGTTGCCAATGTGCATTAGCTGTTTGCAGCCTCACCTT
CTTTCATGGAGTTTAAGATATAGTGTATTTTCCCAAGGTTTGAACTAGCTCTTCATTTCTT
TATGTTTTAAATGCACTGACCTCCCACATTCCCTTTTTAGTAAAATATTCAGAAATAATTT
AAATACATCATTGCAATGAAAATAAATGTTTTTTATTAGGCAGAATCCAGATGCTCAAGGC
CCTTCATAATATCCCCAGTTTAGTAGTTGGACTTAGGGAACAAAGGAACCTTTAATAGAA
ATTGGACAGCAAGAAAGCGAGCTTAGTGATACTTGTGGGCCAGGGCATTAGCCACACCAGC
CACCACTTTCTGATAGGCAGCCTGCACTGGTGGGGTGAATTCTTTGCCAAAGTGATGGGCC
AGCACACAGACCAGCACGTTGCCCAGGAGCTGTGGGAGGAAGATAAGAGGTATGAACATGA
TTAGCAAAAGGGCCTAGCTTGGACTCAGAATAATCCAGCCTTATCCCAACCATAAAATAAA
AGCAGAATGGTAGCTGGATTGTAGCTGCTATTAGCAATATGAAACCTCTTACATCAGTTAC
AATTTATATGCAGAAATACCCTGTTACTTCTCCCCTTCCTATGACATGAACTTAACCATAG
AAAAGAAGGGGAAAGAAAACATCAAGGGTCCCATAGACTCACCCTGAAGTTCTCAGGATCC
ACGTGCAGCTTGTCACAGTGCAGCTCACTCAGCTGGGCAAAGGTGCCCTTGAGGTTGTCCA
GGTGAGCCAGGCCATCACTAAAGGCACCGAGCACTTTCTTGCCATGAGCCTTCACCTTAGG
GTTGCCCATAACAGCATCAGGAGTGGACAGATCCCCAAAGGACTCAAAGAACCTCTGGGTC
CAAGGGTAGACCACCAGCAGCCTAAGGGTGGGAAAATAGACCAATAGGCAGAGAGAGTCAG
TGCCTATCAGAAACCCAAGAGTCTTCTCTGTCTCCACATGCCCAGTTTCTATTGGTCTCCT
TAAACCTGTCTTGTAACCTTGATACCAACCTGCCCAGGGCCTCACCACCAACGGCATCCAC
GTTCACCTTGTCCCACAGGGCAGTAACGGCAGACTTCTCCTCAGGAGTCAGGTGCACCATG
GTGTCTGTTTGAGGTTGCTAGTAACACAGTTGTGTCAGAAGCAAATGTAAGCAATAGATG
GCTCTGCCCTGACTTTATGCCCAGCCCTGGCTCCTGCCCTCCCTGCTCCTGGGAGTAGAT
TGGCCAACCCTAGGGTGTGGCTCCACAGGGTGAGGTCTAAGTGATGACAGCCGTACCTGTC
```

*Fig. 16B, cont'd.*

```
CTTGGCTCTTCTGGCACTGGCTTAGGAGTTGGACTTCAAACCCTCAGCCCTCCCTCTAAGA
TATATCTCTTGGCCCCATACCATCAGTACAAATTGCTACTAAAACATCCTCCTTTGCAAG
TGTATTTACCCGATACGTATATGTGTATATATATATATATTCAGGAAATAATATATTCT
AGAATATGTCACATTCTGTCTCAGGCATCCATTTTCTTTATGATGCCGTTTGAGGTGGAGT
TTTAGTCAGGTGGTCAGCTTCTCCTTTTTTTGCCATCTGCCCTGTAAGCATCCTGCTGGG
GACCCAGATAGGAGTCATCACTCTAGGCTGAGAACATCTGGGCACACACCCTAAGCCTCAG
CATGACTCATCATGACTCAGCATTGCTGTGCTTGAGCCAGAAGGTTTGCTTAGAAGGTTAC
ACAGAACCAGAAGGCGGGGTGGGGCACTGACCCCGACAGGGGCCTGGCCAGAACTGCTCA
TGCTTGGACTATGGAGGTCACTAATGGAGACACACAGAAATGTAACAGGAACTAAGGAAA
AACTGAAGCTTTGGGGGTATAGGGGAGCAGTCCCATGTAGTAGTAGAATGAAAAATGCTGC
TATGCTGTGCCTCCCCACCTTTCCCATGTCTGCCCTCTACTCATGGTCTATCTCTCCTGG
CTCCTGGGAGTCATGGACTCCACCCAGCACCACCAACCTGACCTAACCACCTATCTGAGCC
TGCCAGCCTATAACCCATCTGGGCCCTGATAGCTGGTGGCCAGCCCTGACCCCACCCCACC
CTCCTGGAACCTCTGATAGACACATCTGGCACACCAGCTCGCAAAGTCACCGTGAGGGTC
TTGTGTTTGCTGAGTCAAAATTCCTTGAAATCCAAGTCCTTAGAGACTCCCAGGCTTGGAT
TCAAAGCTCCTGACTTTCTGTCTAGTGTATGTGCAGTGAGCCCCTTTTCCTCTAACTGAAA
GAAGGAAAAAAAATGGAACCCAAAATATTCTACATAGTTTCCATGTCACAGCCAGGGCTG
GGCAGTCTCCTGTTATTTCTTTAAAATAAATATATCATTTAAATGCATAAATAAGCAAAC
CCTGCTCGGGAATGGGAGGGAGAGTCTCTGGAGTCCACCCCTTCTCGGCCCTGGCTCTGCA
GATAGTGCTATCAAAGCCCTGACAGAGCCCTGCCCATTGCTGGGCCTTGGAGTGAGTCAGC
CTAGTAGAGAGGCAGGGCAAGCCATCTCATAGCTGCTGAGTGGGAGAGAGAAAAGGGCTCA
TTGTCTATAAACTCAGGTCATGGCTATTCTTATCCTGTCCCTCCTTTTCATGTACCATATT
TCTCTTCCTCTTTCTGTGTCTCCTCTTTCCTTCCTCCTTTACTTTCCTTCTAACCTTCCTC
TTTCTCCTCCTCCGGCAAGCCTTTGCTTCTCTTTCTCCCATTCTTCAAGGCCTCCTCCATT
TCCTCTTTTTATTCTCTCTTCCCCTTCCTTTCTTTCCTTCTGCAGAGGCAGAGACGTGCGG
GCCAGGCCCCGAGGGCCTTAACGGCCCCAGAGGCGCTTGCTGTCGGGCCGGGCGCTCCCG
GCACGGGCGGGCGGAGGGGTGGCGCCCGCCTGGGGACCGCAGATTACAAGAGCACCTCCTC
CCCCAACCCCAGGAGGCCCCGCTCCCCATGGCCTACTCGACCACGAGGGAATTCCGATAAT
CAACCTCTGGATTACAAAATTTGTGAAAGATTGACTGGTATTCTTAACTATGTTGCTCCTT
TTACGCTATGTGGATACGCTGCTTTAATGCCTTTGTATCATGCTATTGCTTCCCGTATGGC
TTTCATTTTCTCCTCCTTGTATAAATCCTGGTTGCTGTCTCTTTATGAGGAGTTGTGGCCC
GTTGTCAGGCAACGTGGCGTGGTGTGCACTGTGTTTGCTGACGCAACCCCACTGGTTGGG
GCATTGCCACCACCTGTCAGCTCCTTTCCGGGACTTTCGCTTTCCCCCTCCCTATTGCCAC
GGCGGAACTCATCGCCGCCTGCCTTGCCCGCTGCTGGACAGGGGCTCGGCTGTTGGCACT
GACAATTCCGTGGTGTTGTCGGGGAAATCATCGTCCTTCCTTGGCTGCTCGCCTGTGTTG
CCACCTGGATTCTGCGCGGGACGTCCTTCTGCTACGTCCCTTCGGCCCTCAATCCAGCGGA
CCTTCCTTCCCGCGGCCTGCTGCCGGCTCTGCGGCCTCTTCCGCGTCTTCGCCTTCGCCCT
CAGACGAGTCGGATCTCCCTTTGGGCCGCCTCCCGCATCGATACCGTCGACCTCGAGACC
TAGAAAACATGGCCAATTCGAGCTCGGTACCTTTAAGACCAATGACTTACAAGGCAGCTG
TAGATCTTAGCCACTTTTTAAAAGAAAAGGGGGGACTGGAAGGGCTAATTCACTCCCAACG
AAGACAAGATCCCAGGGATGTACGTCCCTAACCCGCTAGGGGCAGCACCCAGGCCTGCAC
```

*Fig. 16B, cont'd.*

```
TGCCGCCTGCCGGCAGGGGTCCAGTCCTGCTTTTTGCTTGTACTGGGTCTCTCTGGTTAGA
CCAGATCTGAGCCTGGGAGCTCTCTGGCTAACTAGGGAACCCACTGCTTAAGCCTCAATAA
AGCTTGCCTTGAGTGCTTCAAGTAGTGTGTGCCCGTCTGTTGTGTGACTCTGGTAACTAGA
GATCCCTCAGACCCTTTTAGTCAGTGTGGAAAATCTCTAGCAGTAGTAGTTCATGTCATCT
TATTATTCAGTATTTATAACTTGCAAAGAAATGAATATCAGAGAGTGAGAGGAACTTGTTT
ATTGCAGCTTATAATGGTTACAAATAAAGCAATAGCATCACAAATTTCACAAATAAAGCAT
TTTTTTCACTGCATTCTAGTTGTGGTTTGTCCAAACTCATCAATGTATCTTATCATGTCTG
GCTCTAGCTATCCCGCCCTAACTCCGCCCATCCCGCCCCTAACTCCGCCCAGTTCCGCCC
ATTCTCCGCCCCATGGCTGACTAATTTTTTTATTTATGCAGAGGCCGAGGCCGCCTCGGC
CTCTGAGCTATTCCAGAAGTAGTGAGGAGGCTTTTTGGAGGCCTAGGCTTTTGCGTCGAG
ACGTACCCAATTCGCCCTATAGTGAGTCGTATTACGCGCGCTCACTGGCCGTCGTTTTACA
ACGTCGTGACTGGGAAAACCCTGGCGTTACCCAACTTAATCGCCTTGCAGCACATCCCCCT
TTCGCCAGCTGGCGTAATAGCGAAGAGGCCCGCACCGATCGCCCTTCCCAACAGTTGCGCA
GCCTGAATGGCGAATGGCGCGACGCGCCCTGTAGCGGCGCATTAAGCGCGGCGGGTGTGGT
GGTTACGCGCAGCGTGACCGCTACACTTGCCAGCGCCCTAGCGCCCGCTCCTTTCGCTTTC
TTCCCTTCCTTTCTCGCCACGTTCGCCGGCTTTCCCCGTCAAGCTCTAAATCGGGGGCTCC
CTTTAGGGTTCCGATTTAGTGCTTTACGGCACCTCGACCCCAAAAAACTTGATTAGGGTGA
TGGTTCACGTAGTGGGCCATCGCCCTGATAGACGGTTTTCGCCCTTTGACGTTGGAGTCC
ACGTTCTTTAATAGTGGACTCTTGTTCCAAACTGGAACAACACTCAACCCTATCTCGGTCT
ATTCTTTTGATTTATAAGGGATTTTGCCGATTTCGGCCTATTGGTTAAAAAATGAGCTGAT
TTAACAAAAATTTAACGCGAATTTTAACAAATATTAACGTTTACAATTTCCCAGGTGGCA
CTTTTCGGGGAAATGTGCGCGGAACCCCTATTTGTTTATTTTTCTAAATACATTCAAATAT
GTATCCGCTCATGAGACAATAACCCTGATAAATGCTTCAATAATATTGAAAAAGGAAGAGT
ATGAGTATTCAACATTTCCGTGTCGCCCTTATTCCCTTTTTGCGGCATTTTGCCTTCCTG
TTTTTGCTCACCCAGAAACGCTGGTGAAAGTAAAAGATGCTGAAGATCAGTTGGGTGCACG
AGTGGGTTACATCGAACTGGATCTCAACAGCGGTAAGATCCTTGAGAGTTTTCGCCCCGAA
GAACGTTTTCCAATGATGAGCACTTTTAAAGTTCTGCTATGTGGCGCGGTATTATCCCGTA
TTGACGCCGGGCAAGAGCAACTCGGTCGCCGCATACACTATTCTCAGAATGACTTGGTTGA
GTACTCACCAGTCACAGAAAAGCATCTTACGGATGGCATGACAGTAAGAGAATTATGCAGT
GCTGCCATAACCATGAGTGATAACACTGCGGCCAACTTACTTCTGACAACGATCGGAGGAC
CGAAGGAGCTAACCGCTTTTTTGCACAACATGGGGGATCATGTAACTCGCCTTGATCGTTG
GGAACCGGAGCTGAATGAAGCCATACCAAACGACGAGCGTGACACCACGATGCCTGTAGCA
ATGGCAACAACGTTGCGCAAACTATTAACTGGCGAACTACTTACTCTAGCTTCCCGGCAAC
AATTAATAGACTGGATGGAGGCGGATAAAGTTGCAGGACCACTTCTGCGCTCGGCCCTTCC
GGCTGGCTGGTTTATTGCTGATAAATCTGGAGCCGGTGAGCGTGGGTCTCGCGGTATCATT
GCAGCACTGGGGCCAGATGGTAAGCCCTCCCGTATCGTAGTTATCTACACGACGGGGAGTC
AGGCAACTATGGATGAACGAAATAGACAGATCGCTGAGATAGGTGCCTCACTGATTAAGCA
TTGGTAACTGTCAGACCAAGTTTACTCATATATACTTTAGATTGATTTAAAACTTCATTTT
TAATTTAAAAGGATCTAGGTGAAGATCCTTTTGATAATCTCATGACCAAAATCCCTTAAC
GTGAGTTTTCGTTCCACTGAGCGTCAGACCCCGTAGAAAAGATCAAAGGATCTTCTTGAGA
TCCTTTTTTTCTGCGCGTAATCTGCTGCTTGCAAACAAAAAAACCACCGCTACCAGCGGTG
```

*Fig. 16B, cont'd.*

```
GTTTGTTTGCCGGATCAAGAGCTACCAACTCTTTTTCCGAAGGTAACTGGCTTCAGCAGAG
CGCAGATACCAAATACTGTCCTTCTAGTGTAGCCGTAGTTAGGCCACCACTTCAAGAACTC
TGTAGCACCGCCTACATACCTCGCTCTGCTAATCCTGTTACCAGTGGCTGCTGCCAGTGGC
GATAAGTCGTGTCTTACCGGGTTGGACTCAAGACGATAGTTACCGGATAAGGCGCAGCGGT
CGGGCTGAACGGGGGGTTCGTGCACACAGCCCAGCTTGGAGCGAACGACCTACACCGAACT
GAGATACCTACAGCGTGAGCTATGAGAAAGCGCCACGCTTCCCGAAGGGAGAAAGGCGGAC
AGGTATCCGGTAAGCGGCAGGGTCGGAACAGGAGAGCGCACGAGGGAGCTTCCAGGGGGAA
ACGCCTGGTATCTTTATAGTCCTGTCGGGTTTCGCCACCTCTGACTTGAGCGTCGATTTTT
GTGATGCTCGTCAGGGGGGCGGAGCCTATGGAAAAACGCCAGCAACGCGGCC
```

*Fig. 16B, cont'd.*

CCLc-βAS3-FB-mGATA/ANK-ΔHS4/ΔIVS2

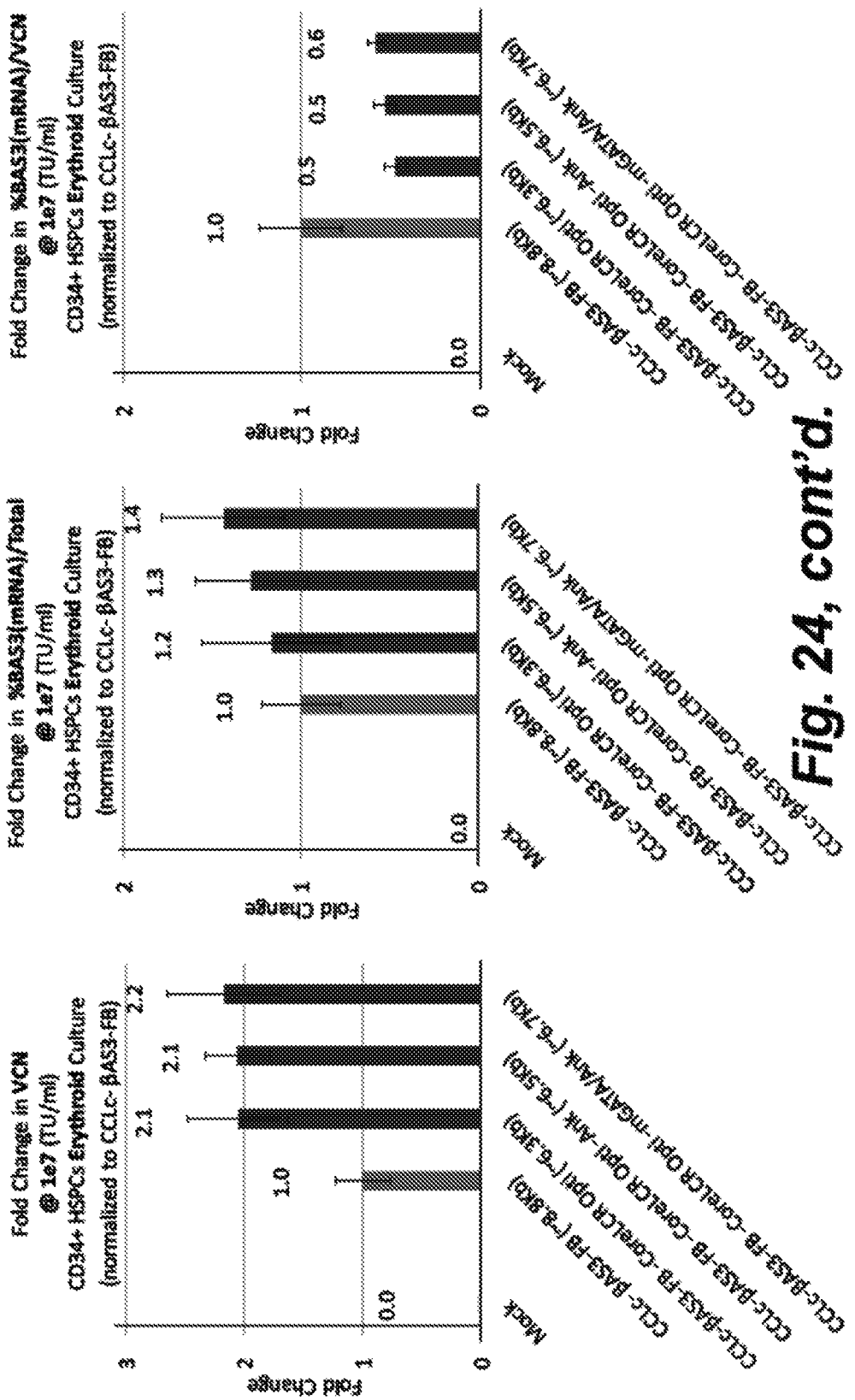
Fig. 24, cont'd.

SEQUENCE LISTING

<160> NUMBER OF SEQ ID NOS: 3

<210> SEQ ID NO 1
<211> LENGTH: 10528
<212> TYPE: DNA
<213> ORGANISM: Artificial
<220> FEATURE:
<223> OTHER INFORMATION: Optimized lentiviral vector

<400> SEQUENCE: 1

```
attttacgg ttcctggcct tttgctggcc ttttgctcac atgttctttc ctgcgttatc      60
ccctgattct gtggataacc gtattaccgc ctttgagtga gctgataccg ctcgccgcag     120
ccgaacgacc gagcgcagcg agtcagtgag cgaggaagcg gaagagcgcc caatacgcaa     180
accgcctctc cccgcgcgtt ggccgattca ttaatgcagc tggcacgaca gtttcccga     240 ctggaaagcg ggcagtgagc gcaacgcaat taatgtgagt tagctcactc attaggcacc     300
ccaggcttta cactttatgc ttccggctcg tatgttgtgt ggaattgtga gcggataaca     360
```

```
atttcacaca ggaaacagct atgaccatga ttacgccaag cgcgcaatta accctcacta    420
aagggaacaa aagctggagc tgcaagcttg gccattgcat acgttgtatc catatcataa    480
tatgtacatt tatattggct catgtccaac attaccgcca tgttgacatt gattattgac    540
tagttattaa tagtaatcaa ttacggggtc attagttcat agcccatata tggagttccg    600
cgttacataa cttacggtaa atggcccgcc tggctgaccg cccaacgacc cccgcccatt    660
gacgtcaata atgacgtatg ttcccatagt aacgccaata gggactttcc attgacgtca    720
atgggtggag tatttacggt aaactgccca cttggcagta catcaagtgt atcatatgcc    780
aagtacgccc cctattgacg tcaatgacgg taaatggccc gcctggcatt atgcccagta    840
catgacctta tgggactttc ctacttggca gtacatctac gtattagtca tcgctattac    900
catggtgatg cggttttggc agtacatcaa tgggcgtgga tagcggtttg actcacgggg    960
atttccaagt ctccacccca ttgacgtcaa tgggagtttg ttttggcacc aaaatcaacg   1020
ggactttcca aaatgtcgta acaactccgc cccattgacg caaatgggcg gtaggcgtgt   1080
acggtgggag gtctatataa gcagagctcg tttagtgaac cggggtctct ctggttagac   1140
cagatctgag cctgggagct ctctggctaa ctagggaacc cactgcttaa gcctcaataa   1200
agcttgcctt gagtgcttca agtagtgtgt gcccgtctgt tgtgtgactc tggtaactag   1260
agatccctca gacccttta gtcagtgtgg aaaatctcta gcagtggcgc ccgaacaggg   1320
acttgaaagc gaaagggaaa ccagaggagc tctctcgacg caggactcgg cttgctgaag   1380
cgcgcacggc aagaggcgag gggcggcgac tggtgagtac gccaaaaatt ttgactagcg   1440
gaggctagaa ggagagagat gggtgcgaga gcgtcagtat taagcggggg agaattagat   1500
cgcgatggga aaaaattcgg ttaaggccag ggggaaagaa aaatatataa ttaaaacata   1560
tagtatgggc aagcagggag ctagaacgat tcgcagttaa tcctggcctg ttagaaacat   1620
cagaaggctg tagacaaata ctgggacagc tacaaccatc ccttcagaca ggatcagaag   1680
aacttagatc attatataat acagtagcaa ccctctattg tgtgcatcaa aggatagaga   1740
taaaagacac caaggaagct ttagacaaga tagaggaaga gcaaaacaaa agtaagacca   1800
ccgcacagca agcggccgct gatcttcaga cctggaggag gagatatgag ggacaattgg   1860
agaagtgaat tatataaata taaagtagta aaaattgaac cattaggagt agcacccacc   1920
aaggcaaaga gaagagtggt gcagagagaa aaaagagcag tgggaatagg agctttgttc   1980
cttgggttct tgggagcagc aggaagcact atgggcgcag cgtcaatgac gctgacggta   2040
caggccagac aattattgtc tggtatagtg cagcagcaga caatttgct gagggctatt   2100 gaggcgcaac agcatctgtt gcaactcaca gtctgggca tcaagcagct ccaggcaaga   2160
atcctggctg tggaaagata cctaaaggat caacagctcc tggggatttg gggttgctct   2220
ggaaaactca tttgcaccac tgctgtgcct tggaatgcta gttggagtaa taatctctg   2280 gaacagattt ggaatcacac gacctggatg gagtgggaca gagaaattaa caattacaca   2340
agcttaatac actccttaat tgaagaatcg caaaaccagc aagaaaagaa tgaacaagaa   2400
ttattggaat tagataaatg ggcaagtttg tggaattggt ttaacataac aaattggctg   2460
tggtatataa aattattcat aatgatagta ggaggcttgg taggtttaag aatagttttt   2520
gctgtacttt ctatagtgaa tagagttagg cagggatatt caccattatc gtttcagacc   2580 caccteccaa ccccgagggg acccgacagg cccgaaggaa tagaagaaga aggtggagag   2640
agagacagag acagatccat tcgattagtg aacggatctc gacggtatcg atctcgacac   2700
aaatggcagt attcatccac aatttttaaaa gaaaaggggg gattgggggg tacagtgcag   2760
```

```
gggaaagaat agtagacata atagcaacag acatacaaac taaagaatta caaaaacaaa    2820
ttacaaaaat tcaaaatttt cgggtttatt acagggacag cagagatcca gtttgggtcg    2880
aggatatcgg atcggaattc tctagatgat caggatccct cgagcccta tcgatcacga    2940 gactagcctc gactactagt ggagatcccc cgggctgcag agccagaagc accataaggg    3000
acatgataag ggagccagca gacctctgat ctcttcctga atgctaatct taaacatcct    3060
gaggaagaat gggacttcca tttggggtgg gcctatgata gggtaataag acagtagtga    3120
atatcaagct acaaaaagcc cccttttcaaa ttcttctcag tcctaacttt tcatactaag    3180
cccagtcctt ccaaagcaga ctgtgaaaga gtgatagttc cgggagacta gcactgcaga    3240
ttccgggtca ctgtgagtgg gggaggcagg aagaagggc tcacaggaca gtcaaaccat    3300 gcccctgtt tttccttctt caagtagacc tctataagac aacagagaca actaaggctg    3360
agtggccagg cgaggagaaa ccatctcgcc gtaaaacatg gaaggaacac ttcagggaaa    3420
aggtggtatc tctaagcaag agaactgagt ggagtcaagg ctgagagatg caggataagc    3480
aaatgggtag tgaaaagaca ttcatgagga cagctaaaac aataagtaat gtaaaataca    3540
gcatagcaaa actttaacct ccaaatcaag cctctacttg aatccttttc tgagggatga    3600
ataaggcata ggcatcaggg gctgttgcca atgtgcatta gctgtttgca gcctcacctt    3660
ctttcatgga gtttaagata tagtgtattt tcccaaggtt tgaactagct cttcatttct    3720
ttatgtttta aatgcactga cctcccacat tccctttta gtaaatatt cagaaataat    3780 ttaaatacat cattgcaatg aaaataaatg tttttatta ggcagaatcc agatgctcaa    3840
ggcccttcat aatatccccc agtttagtag ttggacttag ggaacaaagg aacctttaat    3900
agaaattgga cagcaagaaa gcgagcttag tgatacttgt gggccagggc attagccaca    3960
ccagccacca ctttctgata ggcagcctgc actggtgggg tgaattcttt gccaaagtga    4020
tgggccagca cacagaccag cacgttgccc aggagctgtg ggaggaagat aagaggtatg    4080
aacatgatta gcaaaagggc ctagcttgga ctcagaataa tccagcctta tcccaaccat    4140
aaaataaaag cagaatggta gctggattgt agctgctatt agcaatatga aacctcttac    4200
atcagttaca atttatatgc agaaatattt atatgcagaa atattgctat tgccttaacc    4260
cagaaattat cactgttatt ctttagaatg gtgcaaagag gcatgataca ttgtatcatt    4320
attgccctga agaaagaga ttagggaaag tattagaaat aagataaaca aaaaagtata    4380 ttaaagaag aaagcatttt ttaaaattac aaatgcaaaa ttaccctgat ttggtcaata    4440 tgtgtacct gttacttctc cccttcctat gacatgaact taaccataga aaagaagggg    4500
aaagaaaaca tcaagggtcc catagactca ccctgaagtt ctcaggatcc acgtgcagct    4560
tgtcacagtg cagctcactc agctgggcaa aggtgccctt gaggttgtcc aggtgagcca    4620
ggccatcact aaaggcaccg agcactttct tgccatgagc cttccctta gggttgccca    4680 taacagcatc aggagtggac agatcccaa aggactcaaa gaacctctgg gtccaagggt    4740
agaccaccag cagcctaagg gtgggaaaat agaccaatag gcagagagag tcagtgccta    4800
tcagaaaccc aagagtcttc tctgtctcca catgcccagt ttctattggt ctccttaaac    4860
ctgtcttgta accttgatac caacctgccc agggcctcac caccaacggc atccacgttc    4920
accttgtccc acagggcagt aacggcagac ttctcctcag gagtcaggtg caccatggtg    4980
tctgtttgag gttgctagtg aacacagttg tgtcagaagc aaatgtaagc aatagatggc    5040
tctgccctga cttttatgcc cagccctggc tcctgccctc cctgctcctg ggagtagatt    5100
```

-continued

```
ggccaaccct agggtgtggc tccacagggt gaggtctaag tgatgacagc cgtacctgtc    5160
cttggctctt ctggcactgg cttaggagtt ggacttcaaa ccctcagccc tccctctaag    5220
atatatctct tggccccata ccatcagtac aaattgctac taaaaacatc ctcctttgca    5280
agtgtattta cccgacgcgt cggcgataag cttgatccat cgatgacgtg cgggccaggc    5340
ccccgagggc cttaacggcc ccagaggcgc ttgctgtcgg gccgggcgct cccggcacgg    5400
gcgggcggag gggtggcgcc cgcctgggga ccgcagatta caagagcacc tcctccccca    5460
accccaggag gccccgctcc ccatacgtat atgtgtatat atatatatat attcaggaaa    5520
taatatattc tagaatatgt cacattctgt ctcaggcatc catttctttt atgatgccgt    5580
ttgaggtgga gttttagtca ggtggtcagc ttctcctttt ttttgccatc tgccctgtaa    5640
gcatcctgct ggggacccag ataggagtca tcactctagg ctgagaacat ctgggcacac    5700
accctaagcc tcagcatgac tcatcatgac tcagcattgc tgtgcttgag ccagaaggtt    5760
tgcttagaag gttacacaga accagaaggc gggggtgggg cactgacccc gacaggggcc    5820
tggccagaac tgctcatgct tggactatgg gaggtcacta atggagacac acagaaatgt    5880
aacaggaact aaggaaaaac tgaagctttg ggggtatagg ggagcagtcc catgtagtag    5940
tagaatgaaa aatgctgcta tgctgtgcct cccccacctt tcccatgtct gccctctact    6000
catggtctat ctctcctggc tcctgggagt catggactcc acccagcacc accaacctga    6060
cctaaccacc tatctgagcc tgccagccta aacccatct gggccctgat agctggtggc     6120
cagccctgac cccaccccac cctccctgga acctctgata gacacatctg gcacaccagc    6180
tcgcaaagtc accgtgaggg tcttgtgttt gctgagtcaa aattccttga aatccaagtc    6240
cttagagact cccaggcttg gattcaaagc tcctgacttt ctgtctagtg tatgtgcagt    6300
gagccccttt tcctctaact gaaagaagga aaaaaaatg gaacccaaaa tattctacat     6360
agtttccatg tcacagccag ggctgggcag tctcctgtta tttcttttaa aataaatata    6420
tcatttaaat gcataaataa gcaaaccctg ctcgggaatg ggaggagag tctctggagt     6480 ccaccccttc tcggccctgg ctctgcagat agtgctatca aagccctgac agagccctgc    6540
ccattgctgg gccttggagt gagtcagcct agtagagagg cagggcaagc catctcatag    6600
ctgctgagtg ggagagagaa aagggctcat tgtctataaa ctcaggtcat ggctattctt    6660
atggcctact cgaccacgag ggaattccga taatcaacct ctggattaca aaatttgtga    6720
aagattgact ggtattctta actatgttgc tccttttacg ctatgtggat acgctgcttt    6780
aatgcctttg tatcatgcta ttgcttcccg tatggctttc attttctcct ccttgtataa    6840
atcctggttg ctgtctcttt atgaggagtt gtggcccgtt gtcaggcaac gtggcgtggt    6900
gtgcactgtg tttgctgacg caaccccac tggttgggc attgccacca cctgtcagct     6960
cctttccggg actttcgctt tccccctccc tattgccacg gcggaactca tcgccgcctg    7020
ccttgcccgc tgctggacag gggctcggct gttgggcact gacaattccg tggtgttgtc    7080
ggggaaatca tcgtcctttc cttggctgct cgcctgtgtt gccacctgga ttctgcgcgg    7140
gacgtccttc tgctacgtcc cttcggccct caatccagcg gaccttcctt cccgcggcct    7200
gctgccggct ctgcggcctc ttccgcgtct tcgccttcgc cctcagacga gtcggatctc    7260
cctttgggcc gcctccccgc atcgataccg tcgacctcga gacctagaaa aacatggcca    7320
attcgagctc ggtacccttta agaccaatga cttacaaggc agctgtagat cttagccact    7380
ttttaaaaga aagggggga ctggaagggc taattcactc ccaacgaaga caagatccca    7440
gggatgtacg tccctaaccc gctagggggc agcacccagg cctgcactgc cgcctgccgg    7500
```

```
caggggtcca gtcctgcttt ttgcttgtac tgggtctctc tggttagacc agatctgagc    7560
ctgggagctc tctggctaac tagggaaccc actgcttaag cctcaataaa gcttgccttg    7620
agtgcttcaa gtagtgtgtg cccgtctgtt gtgtgactct ggtaactaga gatccctcag    7680
acccttttag tcagtgtgga aaatctctag cagtagtagt tcatgtcatc ttattattca    7740
gtatttataa cttgcaaaga aatgaatatc agagagtgag aggaacttgt ttattgcagc    7800
ttataatggt tacaaataaa gcaatagcat cacaaatttc acaaataaag cattttttc     7860 actgcattct agttgtggtt tgtccaaact catcaatgta tcttatcatg tctggctcta    7920
gctatcccgc ccctaactcc gcccatcccg ccccctaactc cgcccagttc cgcccattct   7980
ccgccccatg gctgactaat tttttttatt tatgcagagg ccgaggccgc ctcggcctct    8040
gagctattcc agaagtagtg aggaggcttt tttggaggcc taggcttttg cgtcgagacg    8100
tacccaattc gccctatagt gagtcgtatt acgcgcgctc actggccgtc gttttacaac    8160
gtcgtgactg ggaaaaccct ggcgttaccc aacttaatcg ccttgcagca catccccctt    8220
tcgccagctg gcgtaatagc gaagaggccc gcaccgatcg cccttcccaa cagttgcgca    8280
gcctgaatgg cgaatggcgc gacgcgccct gtagcggcgc attaagcgcg gcgggtgtgg    8340
tggttacgcg cagcgtgacc gctacacttg ccagcgccct agcgcccgct cctttcgctt    8400
tcttcccttc ctttctcgcc acgttcgccg gctttccccg tcaagctcta aatcgggggc    8460
tccctttagg gttccgattt agtgctttac ggcacctcga ccccaaaaaa cttgattagg    8520
gtgatggttc acgtagtggg ccatcgccct gatagacggt ttttcgccct ttgacgttgg    8580
agtccacgtt ctttaatagt ggactcttgt tccaaactgg aacaacactc aaccctatct    8640
cggtctattc ttttgattta agggatttt gccgatttc ggcctattgg ttaaaaaatg     8700
agctgattta acaaaaattt aacgcgaatt ttaacaaaat attaacgttt acaatttccc    8760
aggtggcact tttcggggaa atgtgcgcgg aaccccctatt tgtttatttt tctaaataca   8820
ttcaaatatg tatccgctca tgagacaata accctgataa atgcttcaat aatattgaaa    8880
aaggaagagt atgagtattc aacatttccg tgtcgccctt attcccttt ttgcggcatt     8940 ttgccttcct gtttttgctc acccagaaac gctggtgaaa gtaaaagatg ctgaagatca    9000
gttgggtgca cgagtgggtt acatcgaact ggatctcaac agcggtaaga tccttgagag    9060
ttttcgcccc gaagaacgtt ttccaatgat gagcactttt aaagttctgc tatgtggcgc    9120
ggtattatcc cgtattgacg ccgggcaaga gcaactcggt cgccgcatac actattctca    9180
gaatgacttg gttgagtact caccagtcac agaaaagcat cttacggatg gcatgacagt    9240
aagagaatta tgcagtgctg ccataaccat gagtgataac actgcggcca acttacttct    9300
gacaacgatc ggaggaccga aggagctaac cgcttttttg cacaacatgg gggatcatgt    9360
aactcgcctt gatcgttggg aaccggagct gaatgaagcc ataccaaacg acgagcgtga    9420
caccacgatg cctgtagcaa tggcaacaac gttgcgcaaa ctattaactg gcgaactact    9480
tactctagct tcccggcaac aattaataga ctggatggag gcggataaag ttgcaggacc    9540
acttctgcgc tcggcccttc cggctggctg gtttattgct gataaatctg gagccggtga    9600
gcgtgggtct cgcggtatca ttgcagcact ggggccagat ggtaagccct cccgtatcgt    9660
agttatctac acgacgggga gtcaggcaac tatggatgaa cgaaatagac agatcgctga    9720
gataggtgcc tcactgatta agcattggta actgtcagac caagtttact catatatact    9780
ttagattgat ttaaaacttc attttaatt taaaaggatc taggtgaaga tcctttttga    9840
```

| | |
|---|---|
| taatctcatg accaaaatcc cttaacgtga gttttcgttc cactgagcgt cagaccccgt | 9900 |
| agaaaagatc aaaggatctt cttgagatcc ttttttctg cgcgtaatct gctgcttgca | 9960 |
| aacaaaaaaa ccaccgctac cagcggtggt ttgtttgccg gatcaagagc taccaactct | 10020 |
| ttttccgaag gtaactggct tcagcagagc gcagatacca atactgtcc ttctagtgta | 10080 |
| gccgtagtta ggccaccact tcaagaactc tgtagcaccg cctacatacc tcgctctgct | 10140 |
| aatcctgtta ccagtggctg ctgccagtgg cgataagtcg tgtcttaccg ggttggactc | 10200 |
| aagacgatag ttaccggata aggcgcagcg gtcgggctga acggggggtt cgtgcacaca | 10260 |
| gcccagcttg gagcgaacga cctacaccga actgagatac ctacagcgtg agctatgaga | 10320 |
| aagcgccacg cttcccgaag ggagaaaggc ggacaggtat ccggtaagcg gcagggtcgg | 10380 |
| aacaggagag cgcacgaggg agcttccagg gggaaacgcc tggtatcttt atagtcctgt | 10440 |
| cgggtttcgc cacctctgac ttgagcgtcg attttttgtga tgctcgtcag ggggggcggag | 10500 |
| cctatggaaa aacgccagca acgcggcc | 10528 |

<210> SEQ ID NO 2
<211> LENGTH: 10483
<212> TYPE: DNA
<213> ORGANISM: Artificial
<220> FEATURE:
<223> OTHER INFORMATION: Optimized lentiviral vector

<400> SEQUENCE: 2

| | |
|---|---|
| attttttacgg ttcctggcct tttgctggcc ttttgctcac atgttctttc ctgcgttatc | 60 |
| ccctgattct gtggataacc gtattaccgc ctttgagtga gctgataccg ctcgccgcag | 120 |
| ccgaacgacc gagcgcagcg agtcagtgag cgaggaagcg gaagagcgcc caatacgcaa | 180 |
| accgcctctc cccgcgcgtt ggccgattca ttaatgcagc tggcacgaca ggtttcccga | 240 |
| ctggaaagcg ggcagtgagc gcaacgcaat taatgtgagt tagctcactc attaggcacc | 300 |
| ccaggcttta cactttatgc ttccggctcg tatgttgtgt ggaattgtga gcggataaca | 360 |
| atttcacaca ggaaacagct atgaccatga ttacgccaag cgcgcaatta accctcacta | 420 |
| aagggaacaa aagctgggagc tgcaagcttg gccattgcat acgttgtatc catatcataa | 480 |
| tatgtacatt tatattggct catgtccaac attaccgcca tgttgacatt gattattgac | 540 |
| tagttattaa tagtaatcaa ttacggggtc attagttcat agcccatata tggagttccg | 600 |
| cgttacataa cttacggtaa atggcccgcc tggctgaccg cccaacgacc cccgcccatt | 660 |
| gacgtcaata atgacgtatg ttcccatagt aacgccaata gggactttcc attgacgtca | 720 |
| atgggtggag tatttacggt aaactgccca cttggcagta catcaagtgt atcatatgcc | 780 |
| aagtacgccc cctattgacg tcaatgacgg taaatggccc gcctggcatt atgcccagta | 840 |
| catgacctta tgggactttc ctacttggca gtacatctac gtattagtca tcgctattac | 900 |
| catggtgatg cggttttggc agtacatcaa tgggcgtgga tagcggtttg actcacgggg | 960 |
| atttccaagt ctccacccca ttgacgtcaa tgggagtttg ttttggcacc aaaatcaacg | 1020 |
| ggactttcca aaatgtcgta acaactccgc cccattgacg caaatgggcg gtaggcgtgt | 1080 |
| acggtgggag gtctatataa gcagagctcg tttagtgaac cggggtctct ctggttagac | 1140 |
| cagatctgag cctgggagct ctctggctaa ctagggaacc cactgcttaa gcctcaataa | 1200 |
| agcttgcctt gagtgcttca agtagtgtgt gcccgtctgt tgtgtgactc tggtaactag | 1260 |
| agatccctca gacccttta gtcagtgtgg aaaatctcta gcagtggcgc ccgaacaggg | 1320 |
| acttgaaagc gaaagggaaa ccagaggagc tctctcgacg caggactcgg cttgctgaag | 1380 |

```
cgcgcacggc aagaggcgag gggcggcgac tggtgagtac gccaaaaatt ttgactagcg 1440
gaggctagaa ggagagagat gggtgcgaga gcgtcagtat taagcggggg agaattagat 1500
cgcgatggga aaaaattcgg ttaaggccag ggggaaagaa aaaatataaa ttaaaacata 1560
tagtatgggc aagcagggag ctagaacgat tcgcagttaa tcctggcctg ttagaaacat 1620
cagaaggctg tagacaaata ctgggacagc tacaaccatc ccttcagaca ggatcagaag 1680
aacttagatc attatataat acagtagcaa ccctctattg tgtgcatcaa aggatagaga 1740
taaaagacac caaggaagct ttagacaaga tagaggaaga gcaaaacaaa agtaagacca 1800
ccgcacagca agcggccgct gatcttcaga cctggaggag gagatatgag ggacaattgg 1860
agaagtgaat tatataaata taaagtagta aaaattgaac cattaggagt agcacccacc 1920
aaggcaaaga gaagagtggt gcagagagaa aaaagagcag tgggaatagg agctttgttc 1980
cttgggttct tgggagcagc aggaagcact atgggcgcag cgtcaatgac gctgacggta 2040
caggccagac aattattgtc tggtatagtg cagcagcaga acaatttgct gagggctatt 2100
gaggcgcaac agcatctgtt gcaactcaca gtctggggca tcaagcagct ccaggcaaga 2160
```
atcctggctg tggaaagata cctaaaggat caacagctcc tggggatttg gggttgctct 2220
ggaaaactca tttgcaccac tgctgtgcct tggaatgcta gttggagtaa taaatctctg 2280
gaacagattt ggaatcacac gacctggatg gagtgggaca gagaaattaa caattacaca 2340
agcttaatac actccttaat tgaagaatcg caaaaccagc aagaaaagaa tgaacaagaa 2400
ttattggaat tagataaatg ggcaagtttg tggaattggt ttaacataac aaattggctg 2460
tggtatataa aattattcat aatgatagta ggaggcttgg taggtttaag aatagttttt 2520
gctgtacttt ctatagtgaa tagagttagg cagggatatt caccattatc gtttcagacc 2580
cacctcccaa ccccgagggg acccgacagg cccgaaggaa tagaagaaga aggtggagag 2640
agagacagag acagatccat tcgattagtg aacggatctc gacggtatcg atctcgacac 2700
aaatggcagt attcatccac aattttaaaa gaaaaggggg gattgggggg tacagtgcag 2760
gggaaagaat agtagacata atagcaacag acatacaaac taaagaatta caaaaacaaa 2820
ttacaaaaat tcaaaatttt cgggtttatt acagggacag cagagatcca gtttgggtcg 2880
aggatatcgg atcggaattc tctagatgat caggatccct cgagccctta tcgatcacga 2940
gactagcctc gactactagt ggagatcccc cgggctgcag agccagaagc accataaggg 3000
acatgataag ggagccagca gacctctgat ctcttcctga atgctaatct taaacatcct 3060
gaggaagaat gggacttcca tttggggtgg gcctatgata gggtaataag acagtagtga 3120
atatcaagct acaaaaagcc ccctttcaaa ttcttctcag tcctaacttt tcatactaag 3180
cccagtcctt ccaaagcaga ctgtgaaaga gtgatagttc cgggagacta gcactgcaga 3240
ttccgggtca ctgtgagtgg gggaggcagg gaagaagggc tcacaggaca gtcaaaccat 3300
gccccctgtt tttccttctt caagtagacc tctataagac aacagagaca actaaggctg 3360
agtggccagg cgaggagaaa ccatctcgcc gtaaaacatg gaaggaacac ttcaggggaa 3420
aggtggtatc tctaagcaag agaactgagt ggagtcaagg ctgagagatg caggataagc 3480
aaatgggtag tgaaaagaca ttcatgagga cagctaaaac aataagtaat gtaaaataca 3540
gcatagcaaa actttaacct ccaaatcaag cctctacttg aatccttttc tgagggatga 3600
ataaggcata ggcatcaggg gctgttgcca atgtgcatta gctgtttgca gcctcacctt 3660
ctttcatgga gtttaagata tagtgtattt tcccaaggtt tgaactagct cttcatttct 3720

```
ttatgtttta aatgcactga cctcccacat tcccttttta gtaaatatt cagaaataat      3780 ttaaatacat cattgcaatg aaaataaatg ttttttatta ggcagaatcc agatgctcaa      3840
ggcccttcat aatatccccc agtttagtag ttggacttag ggaacaaagg aacctttaat      3900
agaaattgga cagcaagaaa gcgagcttag tgatacttgt gggccagggc attagccaca      3960
ccagccacca ctttctgata ggcagcctgc actggtgggg tgaattcttt gccaaagtga      4020
tgggccagca cacagaccag cacgttgccc aggagctgtg ggaggaagat aagaggtatg      4080
aacatgatta gcaaagggc ctagcttgga ctcagaataa tccagcctta tcccaaccat      4140
aaaataaaag cagaatggta gctggattgt agctgctatt agcaatatga aacctcttac      4200
atcagttaca atttatatgc agaaataccc tgttacttct ccccttccta tgacatgaac      4260
ttaaccatag aaaagaaggg gaaagaaaac atcaagggtc ccatagactc accctgaagt      4320
tctcaggatc cacgtgcagc ttgtcacagt gcagctcact cagctgggca aggtgccct      4380 tgaggttgtc caggtgagcc aggccatcac taaaggcacc gagcactttc ttgccatgag      4440
ccttcacctt agggttgccc ataacagcat caggagtgga cagatcccca aaggactcaa      4500
agaacctctg ggtccaaggg tagaccacca gcagcctaag ggtgggaaaa tagaccaata      4560
ggcagagaga gtcagtgcct atcagaaacc caagagtctt ctctgtctcc acatgcccag      4620
tttctattgg tctccttaaa cctgtcttgt aaccttgata ccaacctgcc cagggcctca      4680
ccaccaacgg catccacgtt caccttgtcc cacagggcag taacggcaga cttctcctca      4740
ggagtcaggt gcaccatggt gtctgtttga ggttgctagt gaacacagtt gtgtcagaag      4800
caaatgtaag caatagatgg ctctgccctg acttttatgc ccagccctgg ctcctgccct      4860
ccctgctcct gggagtagat tggccaaccc tagggtgtgg ctccacaggg tgaggtctaa      4920
gtgatgacag ccgtacctgt ccttggctct tctggcactg gcttaggagt tggacttcaa      4980
accctcagcc ctccctctaa gatatatctc ttggccccat accatcagta caaattgcta      5040
ctaaaaacat cctcctttgc aagtgtattt acccgatacg tatatgtgta tatatatata      5100
tatattcagg aaataatata ttctagaata tgtcacattc tgtctcaggc atccattttc      5160
tttatgatgc cgtttgaggt ggagttttag tcaggtggtc agcttctcct ttttttttgcc      5220 atctgccctg taagcatcct gctggggacc cagataggag tcatcactct aggctgagaa      5280
catctgggca cacccctaa gcctcagcat gactcatcat gactcagcat tgctgtgctt      5340
gagccagaag gtttgcttag aaggttacac agaaccagaa ggcgggggtg gggcactgac      5400
cccgacaggg gcctggccag aactgctcat gcttggacta tgggaggtca ctaatgagaa      5460
cacacagaaa tgtaacagga actaaggaaa aactgaagct ttgggggtat aggggagcag      5520
tcccatgtag tagtagaatg aaaaatgctg ctatgctgtg cctcccccac ctttcccatg      5580
tctgccctct actcatggtc tatctctcct ggctcctggg agtcatggac tccacccagc      5640
accaccaacc tgacctaacc acctatctga gcctgccagc ctataaccca tctgggccct      5700
gatagctggt ggccagccct gaccccaccc caccctccct ggaacctctg atagacacat      5760
ctggcacacc agctcgcaaa gtcaccgtga gggtcttgtg tttgctgagt caaaattcct      5820
tgaaatccaa gtccttagag actcccaggc ttggattcaa agctcctgac tttctgtcta      5880
gtgtatgtgc agtgagcccc ttttcctcta actgaaagaa ggaaaaaaaa atggaaccca      5940
aaatattcta catagtttcc atgtcacagc cagggctggg cagtctcctg ttatttcttt      6000
taaaataaat atatcattta aatgcataaa taagcaaacc ctgctcggga atgggaggga      6060
gagtctctgg agtccacccc ttctcggccc tggctctgca gatagtgcta tcaaagccct      6120
```

```
gacagagccc tgcccattgc tgggccttgg agtgagtcag cctagtagag aggcagggca    6180
agccatctca tagctgctga gtgggagaga gaaaagggct cattgtctat aaactcaggt    6240
catggctatt cttatcctgt ccctcctttt catgtaccat atttctcttc ctctttctgt    6300
gtctcctctt tccttcctcc tttactttcc ttctaacctt cctctttctc ctcctccggc    6360
aagcctttgc ttctctttct cccattcttc aaggcctcct ccatttcctc tttttattct    6420
ctcttcccct tcctttcttt ccttctgcag aggcagagac gtgcgggcca ggcccccgag    6480
ggccttaacg gccccagagg cgcttgctgt cgggccgggc gctcccggca cgggcgggcg    6540
gaggggtggc gcccgcctgg ggaccgcaga ttacaagagc acctcctccc ccaaccccag    6600
gaggccccgc tccccatggc ctactcgacc acgagggaat tccgataatc aacctctgga    6660
ttacaaaatt tgtgaaagat tgactggtat tcttaactat gttgctcctt ttacgctatg    6720
tggatacgct gctttaatgc ctttgtatca tgctattgct tcccgtatgg ctttcatttt    6780
ctcctccttg tataaatcct ggttgctgtc tctttatgag gagttgtggc ccgttgtcag    6840
gcaacgtggc gtggtgtgca ctgtgtttgc tgacgcaacc cccactggtt ggggcattgc    6900
caccacctgt cagctccttt ccgggacttt cgctttcccc ctccctattg ccacggcgga    6960
actcatcgcc gcctgccttg cccgctgctg gacaggggct cggctgttgg gcactgacaa    7020
ttccgtggtg ttgtcgggga aatcatcgtc cttttccttgg ctgctcgcct gtgttgccac    7080
ctggattctg cgcgggacgt ccttctgcta cgtcccttcg gccctcaatc cagcggacct    7140
tccttcccgc ggcctgctgc cggctctgcg gcctcttccg cgtcttcgcc ttcgccctca    7200
gacgagtcgg atctcccttt gggccgcctc cccgcatcga taccgtcgac ctcgagacct    7260
agaaaaacat ggccaattcg agctcggtac ctttaagacc aatgacttac aaggcagctg    7320
tagatcttag ccacttttta aagaaaagg ggggactgga agggctaatt cactcccaac    7380
gaagacaaga tcccagggat gtacgtccct aacccgctag ggggcagcac ccaggcctgc    7440
actgccgcct gccggcaggg gtccagtcct gcttttttgct tgtactgggt ctctctggtt    7500
agaccagatc tgagcctggg agctctctgg ctaactaggg aacccactgc ttaagcctca    7560
ataaagcttg ccttgagtgc ttcaagtagt gtgtgcccgt ctgttgtgtg actctggtaa    7620
ctagagatcc ctcagaccct tttagtcagt gtggaaaatc tctagcagta gtagttcatg    7680
tcatcttatt attcagtatt tataacttgc aaagaaatga atatcagaga gtgagaggaa    7740
cttgtttatt gcagcttata atggttacaa ataaagcaat agcatcacaa atttcacaaa    7800
taaagcattt ttttcactgc attctagttg tggtttgtcc aaactcatca atgtatctta    7860
tcatgtctgg ctctagctat cccgccccta actccgccca tcccgcccct aactccgccc    7920
agttccgccc attctccgcc ccatggctga ctaatttttt tatttatgc agaggccgag    7980
gccgcctcgg cctctgagct attccagaag tagtgaggag gcttttttgg aggcctaggc    8040
ttttgcgtcg agacgtaccc aattcgccct atagtgagtc gtattacgcg cgctcactgg    8100
ccgtcgtttt acaacgtcgt gactgggaaa accctggcgt tacccaactt aatcgccttg    8160
cagcacatcc cccttttcgcc agctggcgta atagcgaaga ggcccgcacc gatcgccctt    8220
cccaacagtt gcgcagcctg aatggcgaat ggcgcgacgc gccctgtagc ggcgcattaa    8280
gcgcggcggg tgtggtggtt acgcgcagcg tgaccgctac acttgccagc gccctagcgc    8340
ccgctccttt cgctttcttc ccttcctttc tcgccacgtt cgccggcttt ccccgtcaag    8400
ctctaaatcg ggggctccct ttagggttcc gatttagtgc tttacggcac ctcgacccca    8460
```

| | |
|---|---|
| aaaaacttga ttagggtgat ggttcacgta gtgggccatc gccctgatag acggttttc | 8520 |
| gccctttgac gttggagtcc acgttcttta atagtggact cttgttccaa actggaacaa | 8580 |
| cactcaaccc tatctcggtc tattcttttg atttataagg gattttgccg atttcggcct | 8640 |
| attggttaaa aaatgagctg atttaacaaa aatttaacgc gaattttaac aaaatattaa | 8700 |
| cgtttacaat ttcccaggtg cacttttcg gggaaatgtg cgcggaaccc ctatttgttt | 8760 |
| attttttctaa atacattcaa atatgtatcc gctcatgaga caataaccct gataaatgct | 8820 |
| tcaataatat tgaaaaagga gagtatgag tattcaacat ttccgtgtcg cccttattcc | 8880 |
| cttttttgcg cattttgcc ttcctgtttt tgctcaccca gaaacgctgg tgaaagtaaa | 8940 |
| agatgctgaa gatcagttgg gtgcacgagt gggttacatc gaactggatc tcaacagcgg | 9000 |
| taagatcctt gagagttttc gccccgaaga acgttttcca atgatgagca cttttaaagt | 9060 |
| tctgctatgt ggcgcggtat tatcccgtat tgacgccggg caagagcaac tcggtcgccg | 9120 |
| catacactat tctcagaatg acttggttga gtactcacca gtcacagaaa agcatcttac | 9180 |
| ggatggcatg acagtaagag aattatgcag tgctgccata accatgagtg ataacactgc | 9240 |
| ggccaactta cttctgacaa cgatcggagg accgaaggag ctaaccgctt ttttgcacaa | 9300 |
| catgggggat catgtaactc gccttgatcg ttgggaaccg gagctgaatg aagccatacc | 9360 |
| aaacgacgag cgtgacacca cgatgcctgt agcaatggca acaacgttgc gcaaactatt | 9420 |
| aactggcgaa ctacttactc tagcttcccg gcaacaatta atagactgga tggaggcgga | 9480 |
| taaagttgca ggaccacttc tgcgctcggc ccttccggct ggctggttta ttgctgataa | 9540 |
| atctggagcc ggtgagcgtg ggtctcgcgg tatcattgca gcactggggc cagatggtaa | 9600 |
| gccctcccgt atcgtagtta tctacacgac ggggagtcag gcaactatgg atgaacgaaa | 9660 |
| tagacagatc gctgagatag gtgcctcact gattaagcat tggtaactgt cagaccaagt | 9720 |
| ttactcatat atactttaga ttgatttaaa acttcatttt taatttaaaa ggatctaggt | 9780 |
| gaagatcctt tttgataatc tcatgaccaa aatcccttaa cgtgagtttt cgttccactg | 9840 |
| agcgtcagac cccgtagaaa agatcaaagg atcttcttga gatcctttt ttctgcgcgt | 9900 |
| aatctgctgc ttgcaaacaa aaaaaccacc gctaccagcg gtggtttgtt tgccggatca | 9960 |
| agagctacca actctttttc cgaaggtaac tggcttcagc agagcgcaga taccaaatac | 10020 |
| tgtccttcta gtgtagccgt agttaggcca ccacttcaag aactctgtag caccgcctac | 10080 |
| atacctcgct ctgctaatcc tgttaccagt ggctgctgcc agtggcgata agtcgtgtct | 10140 |
| taccgggttg gactcaagac gatagttacc ggataaggcg cagcggtcgg gctgaacggg | 10200 |
| gggttcgtgc acacagccca gcttggagcg aacgacctac accgaactga gatacctaca | 10260 |
| gcgtgagcta tgagaaagcg ccacgcttcc cgaagggaga aaggcggaca ggtatccggt | 10320 |
| aagcggcagg gtcggaacag gagagcgcac gagggagctt ccaggggaa acgcctggta | 10380 |
| tctttatagt cctgtcgggt ttcgccacct ctgacttgag cgtcgatttt tgtgatgctc | 10440 |
| gtcaggggg cggagcctat ggaaaaacgc cagcaacgcg gcc | 10483 |

<210> SEQ ID NO 3
<211> LENGTH: 10150
<212> TYPE: DNA
<213> ORGANISM: artificial
<220> FEATURE:
<223> OTHER INFORMATION: Optimized lentiviral vector

<400> SEQUENCE: 3

| | |
|---|---|
| gcgcaacgca attaatgtga gttagctcac tcattaggca ccccaggctt tacactttat | 60 |

```
gcttccggct cgtatgttgt gtggaattgt gagcggataa caatttcaca caggaaacag      120
ctatgaccat gattacgcca agcgcgcaat aaccctcac taaagggaac aaaagctgga       180
gctgcaagct tggccattgc atacgttgta tccatatcat aatatgtaca tttatattgg     240
ctcatgtcca acattaccgc catgttgaca ttgattattg actagttatt aatagtaatc    300
aattacgggg tcattagttc atagcccata tatggagttc cgcgttacat aacttacggt    360
aaatggcccg cctggctgac cgcccaacga cccccgccca ttgacgtcaa taatgacgta    420
tgttcccata gtaacgccaa tagggacttt ccattgacgt caatgggtgg agtatttacg   480
gtaaactgcc cacttggcag tacatcaagt gtatcatatg ccaagtacgc ccctattga    540 cgtcaatgac ggtaaatggc ccgcctggca ttatgcccag tacatgacct tatgggactt   600
tcctacttgg cagtacatct acgtattagt catcgctatt accatggtga tgcggttttg   660
gcagtacatc aatgggcgtg gatagcggtt tgactcacgg ggatttccaa gtctccaccc   720
cattgacgtc aatgggagtt tgttttggca ccaaaatcaa cgggactttc caaaatgtcg    780
taacaactcc gccccattga cgcaaatggg cggtaggcgt gtacggtggg aggtctatat   840
aagcagagct cgtttagtga accggggtct ctctggttag accagatctg agcctgggag   900
ctctctggct aactagggaa cccactgctt aagcctcaat aaagcttgcc ttgagtgctt   960
caagtagtgt gtgcccgtct gttgtgtgac tctggtaact agagatccct cagaccccttt  1020 tagtcagtgt ggaaaatctc tagcagtggc gcccgaacag ggacttgaaa gcgaaggga   1080 aaccagagga gctctctcga cgcaggactc ggcttgctga agcgcgcacg gcaagaggcg   1140
aggggcggcg actggtgagt acgccaaaaa ttttgactag cggaggctag aaggagagag   1200
atgggtgcga gagcgtcagt attaagcggg ggagaattag atcgcgatgg gaaaaaattc   1260
ggttaaggcc aggggggaaag aaaaaatata aattaaaaca tatagtatgg gcaagcaggg  1320
agctagaacg attcgcagtt aatcctggcc tgttagaaac atcagaaggc tgtagacaaa   1380
tactgggaca gctacaacca tcccttcaga caggatcaga agaacttaga tcattatata   1440
atacagtagc aaccctctat tgtgtgcatc aaaggataga gataaaagac accaaggaag   1500
ctttagacaa gatagaggaa gagcaaaaca aaagtaagac caccgcacag caagcggccg   1560
ctgatcttca gacctggagg aggagatatg agggacaatt ggagaagtga attatataaa   1620
tataaagtag taaaaattga accattagga gtagcaccca ccaaggcaaa gagaagagtg   1680
gtgcagagag aaaaaagagc agtgggaata ggagctttgt ccttgggtt cttgggagca   1740 gcaggaagca ctatgggcgc agcgtcaatg acgctgacgg tacaggccag acaattattg   1800
tctggtatag tgcagcagca gaacaatttg ctgagggcta ttgaggcgca acagcatctg   1860
ttgcaactca cagtctgggg catcaagcag ctccaggcaa gaatcctggc tgtggaaaga   1920
tacctaaagg atcaacagct cctggggatt tggggttgct ctggaaaact catttgcacc   1980
actgctgtgc cttggaatgc tagttggagt aataaatctc tggaacagat ttggaatcac   2040
acgacctgga tggagtggga cagagaaatt aacaattaca caagcttaat acactcctta   2100
attgaagaat cgcaaaacca gcaagaaaag aatgaacaag aattattgga attagataaa   2160
tgggcaagtt tgtggaattg gtttaacata acaaattggc tgtggtatat aaaattattc   2220
ataatgatag taggaggctt ggtaggttta agaatagttt ttgctgtact ttctatagtg   2280
aatagagtta ggcagggata ttcaccatta tcgtttcaga cccacctccc aaccccgagg   2340
ggacccgacg ggcccgaagg aatagaagaa gaaggtggag agagagacag agacagatcc   2400
```

```
attcgattag tgaacggatc tcgacggtat cgatctcgac acaaatggca gtattcatcc   2460
acaattttaa aagaaaaggg gggattgggg ggtacagtgc aggggaaaga atagtagaca   2520
taatagcaac agacatacaa actaaagaat tacaaaaaca aattacaaaa attcaaaatt   2580
ttcgggttta ttacagggac agcagagatc cagtttgggt cgaggatatc ggatcggaat   2640
tctctagatg atcaggatcc ctcgagccct tatcgatcac gagactagcc tcgactacta   2700
gtggagatcc cccgggctgc agagccagaa gcaccataag ggacatgata agggagccag   2760
cagacctctg atctcttcct gaatgctaat cttaaacatc ctgaggaaga atgggacttc   2820
catttggggt gggcctatga tagggtaata agacagtagt gaatatcaag ctacaaaaag   2880 cccccttttca aattcttctc agtcctaact tttcatacta agcccagtcc ttccaaagca   2940
gactgtgaaa gagtgatagt tccgggagac tagcactgca gattccgggt cactgtgagt   3000
gggggaggca gggaagaagg gctcacagga cagtcaaacc atgcccctg ttttccttc      3060 ttcaagtaga cctctataag acaacagaga caactaaggc tgagtggcca ggcgaggaga   3120
aaccatctcg ccgtaaaaca tggaaggaac acttcagggg aaaggtggta tctctaagca   3180
agagaactga gtggagtcaa ggctgagaga tgcaggataa gcaaatgggt agtgaaaaga   3240
cattcatgag gacagctaaa acaataagta atgtaaaata cagcatagca aaactttaac   3300
ctccaaatca agcctctact tgaatccttt tctgagggat gaataaggca taggcatcag   3360
gggctgttgc caatgtgcat tagctgtttg cagcctcacc ttctttcatg gagtttaaga   3420
tatagtgtat tttcccaagg tttgaactag ctcttcattt ctttatgttt taaatgcact   3480
gacctcccac attcccttttt tagtaaaata ttcagaaata atttaaatac atcattgcaa   3540
tgaaaataaa tgttttttat taggcagaat ccagatgctc aaggcccttc ataatatccc   3600
ccagtttagt agttggactt agggaacaaa ggaacctta atagaaattg gacagcaaga   3660
aagcgagctt agtgatactt gtgggccagg gcattagcca caccagccac cactttctga   3720
taggcagcct gcactggtgg ggtgaattct ttgccaaagt gatgggccag cacacagacc   3780
agcacgttgc ccaggagctg tgggaggaag ataagaggta tgaacatgat tagcaaaagg   3840
gcctagcttg gactcagaat aatccagcct tatcccaacc ataaaataaa agcagaatgg   3900
tagctggatt gtagctgcta ttagcaatat gaaacctctt acatcagtta caatttatat   3960
gcagaaatac cctgttactt ctccccttcc tatgacatga acttaaccat agaaaagaag   4020
gggaaagaaa acatcaaggg tcccatagac tcaccctgaa gttctcagga tccacgtgca   4080
gcttgtcaca gtgcagctca ctcagctggg caaaggtgcc cttgaggttg tccaggtgag   4140
ccaggccatc actaaaggca ccgagcactt tcttgccatg agccttcacc ttagggttgc   4200
ccataacagc atcaggagtg gacagatccc caaaggactc aaagaacctc tgggtccaag   4260
ggtagaccac cagcagccta agggtgggaa aatagaccaa taggcagaga gagtcagtgc   4320
ctatcagaaa cccaagagtc ttctctgtct ccacatgccc agtttctatt ggtctcctta   4380
aacctgtctt gtaaccttga taccaacctg cccagggcct caccaccaac ggcatccacg   4440
ttcaccttgt cccacagggc agtaacggca gacttctcct caggagtcag gtgcaccatg   4500
gtgtctgttt gaggttgcta gtgaacacag ttgtgtcaga agcaaatgta agcaatagat   4560
ggctctgccc tgacttttat gcccagccct ggctcctgcc ctccctgctc ctgggagtag   4620
attggccaac cctagggtgt ggctccacag ggtgaggtct aagtgatgac agccgtacct   4680
gtccttggct cttctggcac tggcttagga gttggacttc aaaccctcag ccctccctct   4740
aagatatatc tcttggcccc ataccatcag tacaaattgc tactaaaaac atcctccttt   4800
```

```
gcaagtgtat ttacccgacg cgtcggcgat aagcttgatc catcgattac gtatatgtgt    4860
atatatatat atatattcag gaaataatat attctagaat atgtcacatt ctgtctcagg    4920
catccatttt ctttatgatg ccgtttgagg tggagtttta gtcaggtggt cagcttctcc    4980 tttttttgc catctgccct gtaagcatcc tgctggggac ccagatagga gtcatcactc    5040
taggctgaga acatctgggc acacaccta agcctcagca tgactcatca tgactcagca    5100
ttgctgtgct tgagccagaa ggtttgctta gaaggttaca cagaaccaga aggcggggt    5160 ggggcactga ccccgacagg ggcctggcca gaactgctca tgcttggact atgggaggtc    5220
actaatggag acacacagaa atgtaacagg aactaaggaa aaactgaagc tttgggggta    5280
taggggagca gtcccatgta gtagtagaat gaaaaatgct gctatgctgt gcctccccca    5340
cctttcccat gtctgccctc tactcatggt ctatctctcc tggctcctgg gagtcatgga    5400
ctccacccag caccaccaac ctgacctaac cacctatctg agcctgccag cctataaccc    5460
atctgggccc tgatagctgg tggccagccc tgacccacc ccaccctccc tggaacctct    5520
gatagacaca tctggcacac cagctcgcaa agtcaccgtg agggtcttgt gtttgctgag    5580
tcaaaattcc ttgaaatcca agtccttaga actcccagg cttggattca aagctcctga    5640
ctttctgtct agtgtatgtg cagtgagccc cttttcctct aactgaaaga aggaaaaaaa    5700
aatggaaccc aaaatattct acatagtttc catgtcacag ccagggctgg gcagtctcct    5760
gttatttctt ttaaaataaa tatatcattt aaatgcataa ataagcaaac cctgctcggg    5820
aatgggaggg agagtctctg gagtccaccc cttctcggcc ctggctctgc agatagtgct    5880
atcaaagccc tgacagagcc ctgcccattg ctgggccttg gagtgagtca gcctagtaga    5940
gaggcagggc aagccatctc atagctgctg agtgggagag agaaaaggc tcattgtcta    6000 taaactcagg tcatggctat tcttatggcc tactcgacca cgagggaatt ccgataatca    6060
acctctggat tacaaaattt gtgaaagatt gactggtatt cttaactatg ttgctccttt    6120
tacgctatgt ggatacgctg cttaatgcc tttgtatcat gctattgctt cccgtatggc    6180
tttcattttc tcctccttgt ataaatcctg gttgctgtct ctttatgagg agttgtggcc    6240
cgttgtcagg caacgtggcg tggtgtgcac tgtgtttgct gacgcaaccc ccactggttg    6300
gggcattgcc accacctgtc agctcctttc cgggactttc gctttcccc tcctattgc    6360 cacggcggaa ctcatcgccg cctgccttgc ccgctgctgg acaggggctc ggctgttggg    6420
cactgacaat tccgtggtgt tgtcggggaa atcatcgtcc tttccttggc tgctcgcctg    6480
tgttgccacc tggattctgc gcgggacgtc cttctgctac gtcccttcgg ccctcaatcc    6540
agcggacctt ccttcccgcg gcctgctgcc ggctctgcgg cctcttccgc gtcttcgcct    6600
tcgccctcag acgagtcgga tctcccttg gccgcctcc ccgcatcgat accgtcgacc    6660
tcgagaccta gaaaacatg gccaattcga gctcggtacc tttaagacca atgacttaca    6720
aggcagctgt agatcttagc cacttttaa aagaaaggg gggactggaa gggctaattc    6780
actcccaacg aagacaagat cccagggatg tacgtccta acccgctagg gggcagcacc    6840
caggcctgca ctgccgcctg ccggcagggg tccagtcctg cttttgctt gtactgggtc    6900 tctctggtta gaccagatct gagcctggga gctctctggc taactaggga acccactgct    6960
taagcctcaa taaagcttgc cttgagtgct tcaagtagtg tgtgcccgtc tgttgtgtga    7020
ctctggtaac tagagatccc tcagaccctt ttagtcagtg tggaaaatct ctagcagtag    7080
tagttcatgt catcttatta ttcagtattt ataacttgca aagaaatgaa tatcagagag    7140
```

-continued

```
tgagaggaac ttgtttattg cagcttataa tggttacaaa taaagcaata gcatcacaaa    7200
tttcacaaat aaagcatttt tttcactgca ttctagttgt ggtttgtcca aactcatcaa    7260
tgtatcttat catgtctggc tctagctatc ccgcccctaa ctccgcccat cccgcccta     7320
actccgccca gttccgccca ttctccgccc catggctgac taattttttt tatttatgca    7380
gaggccgagg ccgcctcggc ctctgagcta ttccagaagt agtgaggagg cttttttgga    7440
ggcctaggct tttgcgtcga dacgtaccca attcgcccta tagtgagtcg tattacgcgc    7500
gctcactggc cgtcgtttta caacgtcgtg actgggaaaa ccctggcgtt acccaactta    7560
atcgccttgc agcacatccc cctttcgcca gctggcgtaa tagcgaagag gcccgcaccg    7620
atcgccttc ccaacagttg cgcagcctga atggcgaatg gcgcgacgcg ccctgtagcg    7680
gcgcattaag cgcggcgggt gtggtggtta cgcgcagcgt gaccgctaca cttgccagcg    7740
ccctagcgcc cgctcctttc gctttcttcc cttcctttct cgccacgttc gccggctttc    7800
cccgtcaagc tctaaatcgg gggctcccctt tagggttccg atttagtgct ttacggcacc    7860
tcgaccccaa aaaacttgat tagggtgatg gttcacgtag tgggccatcg ccctgataga    7920
cggttttttcg ccctttgacg ttggagtcca cgttctttaa tagtggactc ttgttccaaa    7980
ctggaacaac actcaaccct atctcggtct attcttttga ttttataaggg attttgccga    8040
tttcggccta ttggttaaaa aatgagctga tttaacaaaa atttaacgcg aattttaaca    8100
aaatattaac gtttacaatt tcccagtggg cacttttcgg ggaaatgtgc gcggaacccc    8160
tatttgtttta tttttctaaa tacattcaaa tatgtatccg ctcatgagac aataaccctg    8220
ataaatgctt caataatatt gaaaaaggaa gagtatgagt attcaacatt tccgtgtcgc    8280
ccttattccc ttttttgcgg cattttgcct tcctgttttt gctcacccag aaacgctggt    8340
gaaagtaaaa gatgctgaag atcagttggg tgcacgagtg ggttacatcg aactggatct    8400
caacagcggt aagatccttg agagttttcg ccccgaagaa cgttttccaa tgatgagcac    8460
ttttaaagtt ctgctatgtg gcgcggtatt atcccgtatt gacgccgggc aagagcaact    8520
cggtcgccgc atacactatt ctcagaatga cttggttgag tactcaccag tcacagaaaa    8580
gcatcttacg gatggcatga cagtaagaga attatgcagt gctgccataa ccatgagtga    8640
taacactgcg gccaacttac ttctgacaac gatcggagga ccgaaggagc taaccgcttt    8700
tttgcacaac atgggggatc atgtaactcg ccttgatcgt tgggaaccgg agctgaatga    8760
agccatacca aacgacgagc gtgacaccac gatgcctgta gcaatggcaa caacgttgcg    8820
caaactatta actggcgaac tacttactct agcttcccgg caacaattaa tagactggat    8880
ggaggcggat aaagttgcag gaccacttct gcgctcggcc cttccggctg gctggtttat    8940
tgctgataaa tctggagccg gtgagcgtgg gtctcgcggt atcattgcag cactggggcc    9000
agatggtaag ccctcccgta tcgtagttat ctacacgacg gggagtcagg caactatgga    9060
tgaacgaaat agacagatcg ctgagatagg tgcctcactg attaagcatt ggtaactgtc    9120
agaccaagtt tactcatata tactttagat tgatttaaaa cttcattttt aatttaaaag    9180
gatctaggtg aagatccttt ttgataatct catgaccaaa atcccttaac gtgagttttc    9240
gttccactga gcgtcagacc ccgtagaaaa gatcaaagga tcttcttgag atccttttt    9300
tctgcgcgta atctgctgct tgcaaacaaa aaaaccaccg ctaccagcgg tggtttgttt    9360
gccggatcaa gagctaccaa ctctttttcc gaaggtaact ggcttcagca gagcgcagat    9420
accaaatact gtccttctag tgtagccgta gttaggccac cacttcaaga actctgtagc    9480
accgcctaca tacctcgctc tgctaatcct gttaccagtg gctgctgcca gtggcgataa    9540
```

```
gtcgtgtctt accgggttgg actcaagacg atagttaccg gataaggcgc agcggtcggg    9600
ctgaacgggg ggttcgtgca cacagcccag cttggagcga acgacctaca ccgaactgag    9660
atacctacag cgtgagctat gagaaagcgc cacgcttccc gaagggagaa aggcggacag    9720
gtatccggta agcggcaggg tcggaacagg agagcgcacg agggagcttc caggggggaaa    9780 cgcctggtat ctttatagtc ctgtcgggtt tcgccacctc tgacttgagc gtcgattttt    9840
gtgatgctcg tcagggggc ggagcctatg gaaaaacgcc agcaacgcgg ccatttttac    9900
ggttcctggc cttttgctgg cctttttgctc acatgttctt tcctgcgtta tcccctgatt    9960
ctgtggataa ccgtattacc gcctttgagt gagctgatac cgctcgccgc agccgaacga   10020
ccgagcgcag cgagtcagtg agcgaggaag cggaagagcg cccaatacgc aaaccgcctc   10080
tccccgcgcg ttggccgatt cattaatgca gctggcacga caggtttccc gactggaaag   10140
cgggcagtga                                                          10150
```

OPTIMIZED LENTIVIRAL VECTOR FOR STEM CELL GENE THERAPY OF HEMOGLOBINOPATHIES

CROSS-REFERENCE TO RELATED APPLICATIONS

This application is a U.S. 371 National Phase of PCT/US2017/064766, filed on Dec. 5, 2017, which claims benefit of and priority to U.S. Ser. No. 62/430,157, filed on Dec. 5, 2016, which is incorporated herein by reference in its entirety for all purposes.

STATEMENT OF GOVERNMENTAL SUPPORT

[Not Applicable]

INCORPORATION BY REFERENCE OF SEQUENCE LISTING PROVIDED AS A TEXT FILE

A Sequence Listing is provided herewith as a text file, "UCLA-P180US_ST25" created on Oct. 1, 2019 and having a size of 40.4 kb. The contents of the text file are incorporated by reference herein in their entirety.

BACKGROUND

Sickle cell disease (SCD) is one of the most common monogenic disorders worldwide and is a major cause of morbidity and early mortality (Hoffman et al. (2009) Hematology: Basic Principles and Practice. 5th ed. London, United Kingdom, Churchill Livingstone). SCD affects approximately 80,000 Americans, and causes significant neurologic, pulmonary, and renal injury, as well as severe acute and chronic pain that adversely impacts quality of life. It is estimated that approximately 240,000 children are born annually in Africa with SCD and 80% die by their second birthday. The average lifespan of subjects with SCD in the United States is approximately 40 years and this has remained unchanged over the last 3-4 decades.

SCD is caused by a single amino acid change in β-globin (Glu 6 to Val 6) which leads to hemoglobin polymerization and red blood cell (rbc) sickling. SCD typically results in continual low-grade ischemia and episodic exacerbations or "crises" resulting in tissue ischemia, organ damage, and premature death.

Although SCD is well characterized, there is still no ideal long-term treatment. Current therapies are based on induction of fetal hemoglobin (HbF) to inhibit polymerization of sickle hemoglobin (HbS) (Voskaridou et al. (2010) Blood, 115(12): 2354-2363) and cell dehydration (Eaton and Hofrichter (1987) Blood, 70(5): 1245-1266) or reduction of the percentage of HbS by transfusions (Stamatoyannopoulos et al., eds. (2001) Molecular Basis of Blood Diseases. 3rd ed. Philadelphia, Pennsylvania, USA: WB Saunders). Allogeneic human stem cell transplantation (HSCT) from bone marrow (BM) or umbilical cord blood (UCB) or mobilized peripheral blood stem cells (mPBSC) is a potentially curative therapy, although only a small percentage of patients have undergone this procedure, mostly children with severe symptoms who had HLA-matched sibling donors (Bolaños-Meade and Brodsky (2009) Curr. Opin. Oncol. 21(2): 158-161; Rees et al. (2010) Lancet, 376(9757): 2018-2031; Shenoy (2011) Hematology Am Soc Hematol Educ Program. 2011: 273-279).

Transplantation of allogeneic cells carries the risk of graft-versus host disease (GvHD), which can be a cause of extensive morbidity. HSCT using UCB from matched unrelated donors holds reduced risk of acute or chronic GvHD compared with using BM; however, there is a higher probability of engraftment failure using UCB as a result of its lower cell dose and immunologic immaturity (Kamani et al. (2012) Biol. Blood Marrow Transplant. 18(8): 1265-1272; Locatelli and Pagliara (2012) Pediatr. Blood Cancer. 59(2): 372-376).

Gene therapy with autologous human stem cells (HSCs) is an alternative to allogeneic HSCT, since it avoids the limitations of finding a matched donor and the risks of GvHD and graft rejection. For gene therapy application in SCD patients, the safest source for autologous HSC would be BM, due to the complications previously described when G-CSF was used to collect autologous peripheral blood stem cells (PBSCs) in SCD patients (Abboud et al. (1998) Lancet351(9107): 959; Adler et al. (2001) Blood, 97(10): 3313-3314; Fitzhugh et al. (2009) Cytotherapy, 11(4): 464-471). Although general anesthesia imposes a risk for SCD patients as well, current best medical practices can minimize these (Neumayr et al. (1998) Am. J. Hematol. 57(2): 101-108).

The development of integrating vectors for β-globin gene transfer has been challenging due to the complex regulatory elements needed for high-level, erythroid-specific expression (Lisowski and Sadelain (2008) Br. J. Haematol. 141(3): 335-345). γ-Retroviral vectors were unable to transfer these β-globin expression cassettes intact (Gelinas et al. (1989) Adv. Exp. Med. Biol. 271: 135-148; Gelinas et al. (1989) Prog. Clin. Biol. Res. 316B: 235-249). In contrast, lentiviral vectors (LV) can transfer β-globin cassettes intact with relatively high efficiency, although the titers of these vectors are reduced compared with those of vectors bearing simpler cassettes (May et al. (2000) Nature 406(6791): 82-86; Pawliuk et al. (2001) Science, 294(5550): 2368-2371). In the last decade, many groups have developed different β-globin LV for targeting β-hemoglobinopathies, with successful therapeutic results following transplantation of ex vivo-modified HSC in mouse models (May et al. (2000) Nature 406(6791): 82-86; Pawliuk et al. (2001) Science, 294(5550): 2368-2371; Levasseur et al. (2003) Blood, 102(13):4312-4319; Hanawa et al. (2004) Blood, 104(8): 2281-2290; Puthenveetil et al. (2004) Blood, 104(12): 3445-3453; Miccio et al. (2008) Proc. Natl. Acad. Sci. USA, 105(30):10547-10552; Pestina et al. (2008) Mol. Ther. 17(2): 245-252).

Sickle patients with hereditary persistence of fetal hemoglobin (HbF) (HPFH) have improved survival and amelioration of clinical symptoms, with maximal clinical benefits observed when the HbF is elevated above threshold values (e.g., 8%-15% of the total cellular Hb) (Voskaridou et al. (2010) Blood, 115(12): 2354-2363; Platt et al. (1994) N. Engl. J. Med. 330(23): 1639-1644). Therefore, some gene therapy strategies have employed viral vectors carrying the human γ-globin gene (HBG1/2). However, these constructs expressed HbF poorly in adult erythroid cells, since fetal-specific transcription factors are required for high-level expression of the γ-globin gene (Chakalova et al. (2005) Blood 105(5): 2154-2160; Russell (2007) Eur. J. Haematol. 79(6): 516-525). These limitations have been overcome by embedding the exons encoding human γ-globin within the human β-globin gene 5' promoter and 3' enhancer elements (Hanawa et al. (2004) Blood, 104(8): 2281-2290; Persons et al. (2002) Blood, 101(6): 2175-2183; Perumbeti et al. (2009) Blood, 114(6): 1174-1185). Breda et al. (2012) PLoS One, 7(3): e32345 used an LV vector encoding the human hemoglobin (HBB) gene to increase the expression of normal HbA in CD34⁺-derived erythroid cells from SCD patients, however, the expression level needed when the HBB gene is used would be higher than would be required for HBG1/2 gene expression to achieve therapeutic benefits in SCD patients.

Another approach is to modify β-globin genes to confer antisickling activity by substituting key amino acids from γ-globin. The modified β-globin cassette should yield the necessary high-level, erythroid-specific expression in adult erythroid cells. Pawliuk et al. (2001) *Science*, 294(5550): 2368-2371 designed an LV carrying a human β-globin gene with the amino acid modification T87Q. The glutamine at position 87 of γ-globin has been implicated in the anti-sickling activity of HbF (Nagel et al. (1979) *Proc. Natl. Acad. Sci., USA*, 76(2): 670-672). This anti-sickling construct corrected SCD in 2 murine models of the disease, and a similar LV has been used in a clinical trial for β-thalassemia and SCD in France (Cavazzana-Calvo et al. (2010) *Nature*, 467(7313): 318-322).

Townes and colleagues have taken a similar approach, developing a recombinant human anti-sickling β-globin gene (HBBAS3) encoding a β-globin protein (HbAS3) that has 3 amino substitutions compared with the original (HbA): T87Q for blocking the lateral contact with the canonical Val 6 of HbS, E22A to disrupt axial contacts (McCune et al. (1994) *Proc. Natl. Acad. Sci. USA*, 91(21): 9852-9856) and G16D, which confers a competitive advantage over sickle-β-globin chains for interaction with the α-globin polypeptide. Functional analysis of the purified HbAS3 protein demonstrated that this recombinant protein had potent activity to inhibit HbS tetramer polymerization (Levasseur et al. (2004) *J. Biol. Chem.* 279(26): 27518-27524.). Levasseur et al. (2003) *Blood*, 102(13): 4312-4319, showed efficient transduction of BM stem cells from a murine model of SCD with a self-inactivating (SIN) LV carrying the HBBAS3 transgene that resulted in normalized rbc physiology and prevented the pathological manifestations of SCD.

Unfortunately, current β-globin expression vectors, suffer from low vector titer and sub-optimal gene transfer to hematopoietic stem cells, representing a major barrier toward the effective implementation of this gene therapy strategy to the clinic.

SUMMARY

Various embodiments contemplated herein may include, but need not be limited to, one or more of the following:

Embodiment 1

A recombinant lentiviral vector (LV) comprising:

an expression cassette comprising a nucleic acid construct comprising:
- a human β-globin locus control region comprising at least one hypersensitive site (HS) core sequence from the group consisting of HS2 (e.g., an HS2 consisting of an HS2 core sequence, ~420 bp), HS3 (e.g., an HS3 consisting of an HS3 core sequence, ~340 bp), and HS4 (e.g., an HS4 consisting of an HS4 core sequence, ~410 bp); and
- a recombinant human beta globin gene encoding a beta globin polypeptide; and where said LV is a TAT-independent and self-inactivating (SIN) lentiviral vector.

Embodiment 2

The vector of embodiment 1, wherein said β-globin locus control region comprises hypersensitive site (HS) core sequence HS2 (e.g., an HS2 consisting of an HS2 core sequence).

Embodiment 3

The vector of embodiment 1, wherein said β-globin locus control region comprises hypersensitive site (HS) core sequence HS3 (e.g., an HS3 consisting of an HS3 core sequence).

Embodiment 4

The vector of embodiment 1, wherein said β-globin locus control region comprises hypersensitive site (HS) core sequence HS4 (e.g., an HS4 consisting of an HS4 core sequence).

Embodiment 5

The vector of embodiment 1, wherein said β-globin locus control region comprises hypersensitive site (HS) core sequences HS2 and HS3 (e.g., an HS2 consisting of an HS2 core sequence and an HS3 consisting of an HS3 core sequence).

Embodiment 6

The vector of embodiment 1, wherein said β-globin locus control region comprises hypersensitive site (HS) core sequences HS2 and HS4 (e.g., an HS2 consisting of an HS2 core sequence and an HS4 consisting of an HS4 core sequence).

Embodiment 7

The vector of embodiment 1, wherein said β-globin locus control region comprises hypersensitive site (HS) core sequences HS3 and HS4 (e.g., an HS3 consisting of an HS3 core sequence and an HS4 consisting of an HS4 core sequence).

Embodiment 8

The vector of embodiment 1, wherein said β-globin locus control region comprises hypersensitive site (HS) core sequences HS2, HS3, and HS4 (e.g., an HS2 consisting of an HS2 core sequence, an HS3 consisting of an HS3 core sequence, and an HS4 consisting of an HS4 core sequence).

Embodiment 9

The vector according to any one of embodiments 1-8, wherein said HS2 core sequence consists of a nucleic acid sequence having at least 90%, or at least 95%, or at least 98% sequence identity with the sequence ranging from 5484 to 5908 of SEQ ID NO:1, or from 5077 to 5501 of SEQ ID NO:2.

Embodiment 10

The vector of embodiment 9, wherein said HS2 core sequence consists of a nucleic acid sequence ranging from 5484 to 5908 of SEQ ID NO:1, or from 5077 to 5501 of SEQ ID NO:2.

Embodiment 11

The vector according to any one of embodiments 1-10, wherein said HS3 core sequence consists of a nucleic acid sequence having at least 90%, or at least 95%, or at least 98% sequence identity with the sequence ranging from 5909 to 6252 of SEQ ID NO:1, or from 5502 to 5845 of SEQ ID NO:2.

Embodiment 12

The vector of embodiment 11, wherein said HS3 core sequence consists of a nucleic acid sequence ranging from 5909 to 6252 of SEQ ID NO:1, or from 5502 to 5845 of SEQ ID NO:2.

Embodiment 13

The vector according to any one of embodiments 1-12, wherein said HS4 core sequence consists of a nucleic acid sequence having at least 90%, or at least 95%, or at least 98% sequence identity with the sequence ranging from 6253 to 6662 of SEQ ID NO:1, or from 5846 to 6255 of SEQ ID NO:2.

Embodiment 14

The vector of embodiment 13, wherein said HS4 core sequence consists of a nucleic acid sequence ranging from 6253 to 6662 of SEQ ID NO:1, or from 5846 to 6255 of SEQ ID NO:2.

Embodiment 15

The vector according to any one of embodiments 1-8, wherein said human β-globin locus control region comprises the nucleic acid sequence ranging from 5484 to 6662 of SEQ ID NO:1, or from 5077 to 6255 of SEQ ID NO:2.

Embodiment 16

The vector of embodiment 15, wherein said human β-globin locus control region consists of the nucleic acid sequence ranging from 5484 to 6662 of SEQ ID NO:1, or from 5077 to 6255 of SEQ ID NO:2.

Embodiment 17

The vector according to any one of embodiments 1-16, wherein said human beta globin gene comprises a wild-type beta globin gene and/or a wild-type gamma globin gene.

Embodiment 18

The vector according to any one of embodiments 1-16, wherein said human beta globin gene comprises an anti-sickling human beta globin gene encoding an anti-sickling beta globin polypeptide.

Embodiment 19

The vector of embodiment 18, wherein said anti-sickling human beta globin gene encoding an anti-sickling-beta globin polypeptide comprise one or more mutations selected from the group consisting of Gly16Asp, Glu22Ala and Thr87Gln.

Embodiment 20

The vector of embodiment 19, wherein said beta globin gene comprises the mutation Gly16Asp.

Embodiment 21

The vector according to any one of embodiments 19-20, wherein said beta globin gene comprises the mutation Glu22Ala.

Embodiment 22

The vector according to any one of embodiments 19-21, wherein said beta globin gene comprises the mutation Thr87Gln.

Embodiment 23

The vector of embodiment 19, wherein said anti-sickling human β-globin gene comprises about 2.3 kb of recombinant human β-globin gene including exons and introns under the control of the human β-globin gene 5' promoter and the human β-globin 3' enhancer.

Embodiment 24

The vector according to any one of embodiments 1-23, wherein said β-globin gene comprises β-globin intron 2 with a 375 bp RsaI deletion from IVS2.

Embodiment 25

The vector according to any one of embodiments 1-24, wherein said β-globin gene comprises an SspI (S) to RsaI (R) deletion (~220 bp).

Embodiment 26

The vector according to any one of embodiments 1-25, wherein said vector comprises a human Ankyrin insulator element.

Embodiment 27

The vector of embodiment 26, wherein said human Ankyrin insulator element comprises a nucleic acid sequence having at least 90%, or at least 95%, or at least 98% sequence identity with the sequence ranging from 5325 to 5483 of SEQ ID NO:1, or from 6458 to 6616 of SEQ ID NO:2.

Embodiment 28

The vector of embodiment 27, wherein said human Ankyrin insulator element consists of a nucleic acid sequence ranging from 5325 to 5483 of SEQ ID NO:1, or from 6458 to 6616 of SEQ ID NO:2.

Embodiment 29

The vector according to any one of embodiments 26-28, wherein said human ankyrin insulator is adjacent to HS4.

Embodiment 30

The vector according to any one of embodiments 26-28, wherein said human ankyrin insulator is adjacent to HS2.

Embodiment 31

The vector according to any one of embodiments 1-30, wherein said vector comprises a murine GATA1-H52.

Embodiment 32

The vector of embodiment 31, wherein said murine GATA1-H52 comprises a nucleic acid sequence having at least 90%, or at least 95%, or at least 98% sequence identity with the sequence ranging from 6256 to 6457 SEQ ID NO:2.

Embodiment 33

The vector of embodiment 32, wherein said murine GATA1-H52 consists of the nucleic acid sequence ranging from 6256 to 6457 SEQ ID NO:2.

Embodiment 34

The vector according to any one of embodiments 31-33, wherein said GATA1-H52 is adjacent to HS2.

Embodiment 35

The vector according to any one of embodiments 31-33, wherein said GATA1-HS2 is adjacent to HS4.

Embodiment 36

The vector according to any one of embodiments 1-35, further comprising an insulator in the 3' LTR.

Embodiment 37

The vector of embodiment 36, wherein said insulator comprises FB (FII/BEAD-A), a 77 bp insulator element, which contains the minimal CTCF binding site enhancer-blocking components of the chicken β-globin 5' DnaseI-hypersensitive site 4 (5' HS4).

Embodiment 38

The vector according to any one of embodiments 1-37, wherein said vector comprises a w region vector genome packaging signal.

Embodiment 39

The vector according to any one of embodiments 1-38, wherein the 5' LTR comprises a CMV enhancer/promoter.

Embodiment 40

The vector according to any one of embodiments 1-39, wherein said vector comprises a Rev Responsive Element (RRE).

Embodiment 41

The vector according to any one of embodiments 1-40, wherein said vector comprises a central polypurine tract.

Embodiment 42

The vector according to any one of embodiments 1-41, wherein said vector comprises a post-translational regulatory element.

Embodiment 43

The vector of embodiment 42, wherein the posttranscriptional regulatory element is modified Woodchuck Posttranscriptional Regulatory Element (WPRE).

Embodiment 44

The vector of embodiment 1, wherein said vector comprises the nucleic acid sequence of SEQ ID NO:1.

Embodiment 45

The vector of embodiment 1, wherein said vector comprises the nucleic acid sequence of SEQ ID NO:2.

Embodiment 46

The vector according to any one of embodiments 1-45, wherein said vector is incapable of reconstituting a wild-type lentivirus through recombination.

Embodiment 47

A recombinant lentiviral vector (LV) comprising: an expression cassette comprising a nucleic acid construct comprising:
- a human β-globin locus control region, wherein at least one hypersensitive site (HS) sequence is absent; and
- a recombinant human beta globin gene encoding a beta globin polypeptide; and where said LV is a TAT-independent and self-inactivating (SIN) lentiviral vector.

Embodiment 48

The vector of embodiment 47, wherein said β-globin locus control region omits hypersensitive site (HS) sequence HS4.

Embodiment 49

The vector according to any one of embodiments 47-48, wherein said β-globin locus control region comprises wild-type hypersensitive site (HS) sequence HS2.

Embodiment 50

The vector according to any one of embodiments 47-48, wherein said β-globin locus control region comprises wild-type hypersensitive site (HS) sequence HS3.

Embodiment 51

The vector according to any one of embodiments 47-48, wherein said β-globin locus control region comprises hypersensitive site (HS) core sequence HS2.

Embodiment 52

The vector according to any one of embodiments 47-48, wherein said β-globin locus control region comprises hypersensitive site (HS) core sequences HS3.

Embodiment 53

The vector according to any one of embodiments 47-48, wherein said β-globin locus control region comprises wild-type hypersensitive site (HS) sequences HS2 and HS3.

Embodiment 54

T The vector according to any one of embodiments 47-48, wherein said β-globin locus control region comprises hypersensitive site (HS) core sequences HS2 and HS3.

Embodiment 55

The vector according to any one of embodiments 47-54, wherein said HS2 core sequence consists of a nucleic acid sequence having at least 90%, or at least 95%, or at least 98% sequence identity with the sequence ranging from 5484 to 5908 of SEQ ID NO:1, or from 5077 to 5501 of SEQ ID NO:2.

Embodiment 56

The vector of embodiment 55, wherein said HS2 core sequence consists of a nucleic acid sequence ranging from 5484 to 5908 of SEQ ID NO:1, or from 5077 to 5501 of SEQ ID NO:2.

Embodiment 57

The vector according to any one of embodiments 47-56, wherein said HS3 core sequence consists of a nucleic acid sequence having at least 90%, or at least 95%, or at least 98% sequence identity with the sequence ranging from 5909 to 6252 of SEQ ID NO:1, or from 5502 to 5845 of SEQ ID NO:2.

Embodiment 58

The vector of embodiment 57, wherein said HS3 core sequence consists of a nucleic acid sequence ranging from 5909 to 6252 of SEQ ID NO:1, or from 5502 to 5845 of SEQ ID NO:2.

Embodiment 59

The vector according to any one of embodiments 47-58, wherein said human beta globin gene comprises a wild-type beta globin gene.

Embodiment 60

The vector according to any one of embodiments 47-58, wherein said human beta globin gene comprises an anti-sickling human beta globin gene encoding an anti-sickling beta globin polypeptide.

Embodiment 61

The vector of embodiment 60, wherein said anti-sickling human beta globin gene encoding an anti-sickling-beta globin polypeptide comprise one or more mutations selected from the group consisting of Gly16Asp, Glu22Ala and Thr87Gln.

Embodiment 62

The vector of embodiment 61, wherein said beta globin gene comprises the mutation Gly16Asp.

Embodiment 63

The vector according to any one of embodiments 61-62, wherein said beta globin gene comprises the mutation Glu22Ala.

Embodiment 64

The vector according to any one of embodiments 61-63, wherein said beta globin gene comprises the mutation Thr87Gln.

Embodiment 65

The vector of embodiment 61, wherein said anti-sickling human β-globin gene comprises about 2.3 kb of recombinant human β-globin gene including exons and introns under the control of the human β-globin gene 5' promoter and the human β-globin 3' enhancer.

Embodiment 66

The vector according to any one of embodiments 47-65, wherein said β-globin gene comprises β-globin intron 2 with a 375 bp RsaI deletion from IVS2.

Embodiment 67

The vector according to any one of embodiments 47-66, wherein said vector comprises a human Ankyrin insulator element.

Embodiment 68

The vector of embodiment 67, wherein said human Ankyrin insulator element comprises a nucleic acid sequence having at least 90%, or at least 95%, or at least 98% sequence identity with the sequence ranging from 5325 to 5483 of SEQ ID NO:1, or from 6458 to 6616 of SEQ ID NO:2.

Embodiment 69

The vector of embodiment 68, wherein said human Ankyrin insulator element consists of a nucleic acid sequence ranging from 5325 to 5483 of SEQ ID NO:1, or from 6458 to 6616 of SEQ ID NO:2.

Embodiment 70

The vector according to any one of embodiments 67-69, wherein said human ankyrin insulator is adjacent to HS3.

Embodiment 71

The vector according to any one of embodiments 67-69, wherein said human ankyrin insulator is adjacent to HS2.

Embodiment 72

The vector according to any one of embodiments 47-71, wherein said vector comprises a murine GATA1-H52.

Embodiment 73

The vector of embodiment 72, wherein said murine GATA1-HS2 comprises a nucleic acid sequence having at least 90%, or at least 95%, or at least 98% sequence identity with the sequence ranging from 6256 to 6457 SEQ ID NO:2.

Embodiment 74

The vector of embodiment 73, wherein said murine GATA1-H52 consists of the nucleic acid sequence ranging from 6256 to 6457 SEQ ID NO:2.

Embodiment 75

The vector according to any one of embodiments 72-74, wherein said GATA1-H52 is adjacent to HS2.

Embodiment 76

The vector according to any one of embodiments 72-74, wherein said GATA1-H52 is adjacent to HS4.

Embodiment 77

The vector according to any one of embodiments 47-76, further comprising an insulator in the 3' LTR.

Embodiment 78

The vector of embodiment 77, wherein said insulator comprises FB (FII/BEAD-A), a 77 bp insulator element, which contains the minimal CTCF binding site enhancer-blocking components of the chicken β-globin 5' DnaseI-hypersensitive site 4 (5' HS4).

Embodiment 79

The vector according to any one of embodiments 47-78, wherein said vector comprises a w region vector genome packaging signal.

Embodiment 80

The vector according to any one of embodiments 47-79, wherein the 5' LTR comprises a CMV enhancer/promoter.

Embodiment 81

The vector according to any one of embodiments 47-80, wherein said vector comprises a Rev Responsive Element (RRE).

Embodiment 82

The vector according to any one of embodiments 47-81, wherein said vector comprises a central polypurine tract.

Embodiment 83

The vector according to any one of embodiments 47-82, wherein said vector comprises a post-translational regulatory element.

Embodiment 84

The vector of embodiment 83, wherein the posttranscriptional regulatory element is modified Woodchuck Post-transcriptional Regulatory Element (WPRE).

Embodiment 85

The vector according to any one of embodiments 47-84, wherein said vector is incapable of reconstituting a wild-type lentivirus through recombination.

Embodiment 86

A host cell transduced with a vector according to any one of embodiments 1-85.

Embodiment 87

The host cell of embodiment 86, wherein the cell is a stem cell.

Embodiment 88

The host cell of embodiment 87, wherein said cell is a stem cell derived from bone marrow, or from monilized peripheral blood, or from umbilical blood. In certain embodiments the stem cell is not an embryonic stem cell.

Embodiment 89

The host cell of embodiment 86, wherein the cell is a 293T cell.

Embodiment 90

The host cell of embodiment 86, wherein, wherein the cell is a human hematopoietic progenitor cell.

Embodiment 91

The host cell of embodiment 90, wherein the human hematopoietic progenitor cell is a CD34+ cell.

Embodiment 92

A method of treating a hemoglobinopathy, in a subject, said method comprising:
- transducing a stem cell and/or progenitor cell from said subject with a vector according to any one of embodiments 1-85; and
- transplanting said transduced cell or cells derived therefrom into said subject where said cells or derivatives therefrom express said anti-sickling human beta globin gene.

Embodiment 93

The method of embodiment 92, wherein the cell is a stem cell.

Embodiment 94

The host cell of embodiment 92, wherein said cell is a stem cell derived from bone marrow.

Embodiment 95

The method of embodiment 92, wherein, wherein the cell is a human hematopoietic progenitor cell.

Embodiment 96

The method of embodiment 95, wherein the human hematopoietic progenitor cell is a CD34+ cell.

Embodiment 97

The method according to any one of embodiments 92-96, wherein said hemoglobinopathy is sickle cell disease.

Embodiment 98

The method according to any one of embodiments 92-96, wherein said hemoglobinopathy is β-thalassemia.

Definitions

An "HS core sequence" as used herein refers to a reduced β-globin locous control region (LCR) hypersensitivity site (HS) sequence as defined herein (e.g., (HS2 (~420 bp), HS3 (~340 bp), and/or HS4 (~410 bp)). Full-length HS sequences refers to LCR HS2, HS3, and HS4 as previously defined (e.g., HS2 (~1.20 kb), HS3 (~1.28 kb), and HS4 (~1.1 kb)) (see, e.g., Forrester et al. (1986) Proc. Natl. Acad. Sci. USA, 83: 1359-1363).

"Recombinant" is used consistently with its usage in the art to refer to a nucleic acid sequence that comprises portions that do not naturally occur together as part of a single sequence or that have been rearranged relative to a naturally occurring sequence. A recombinant nucleic acid is created by a process that involves the hand of man and/or is generated from a nucleic acid that was created by hand of man (e.g., by one or more cycles of replication, amplification, transcription, etc.). A recombinant virus is one that comprises a recombinant nucleic acid. A recombinant cell is one that comprises a recombinant nucleic acid.

As used herein, the term "recombinant lentiviral vector" or "recombinant LV) refers to an artificially created polynucleotide vector assembled from an LV and a plurality of additional segments as a result of human intervention and manipulation.

By "globin nucleic acid molecule" is meant a nucleic acid molecule that encodes a globin polypeptide. In various embodiments the globin nucleic acid molecule may include regulatory sequences upstream and/or downstream of the coding sequence.

By "globin polypeptide" is meant a protein having at least 85%, or at least 90%, or at least 95%, or at least 98% amino acid sequence identity to a human alpha, beta or gamma globin.

The term "therapeutic functional globin gene" refers to a nucleotide sequence the expression of which leads to a globin that does not produce a hemoglobinopathy phenotype, and which is effective to provide therapeutic benefits to an individual with a defective globin gene. The functional globin gene may encode a wild-type globin appropriate for a mammalian individual to be treated, or it may be a mutant form of globin, preferably one which provides for superior properties, for example superior oxygen transport properties or anti-sickling properties. The functional globin gene includes both exons and introns, as well as globin promoters and splice donors/acceptors.

By "an effective amount" is meant the amount of a required agent or composition comprising the agent to ameliorate or eliminate symptoms of a disease relative to an untreated patient. The effective amount of composition(s) used to practice the methods described herein for therapeutic treatment of a disease varies depending upon the manner of administration, the age, body weight, and general health of the subject. Ultimately, the attending physician or veterinarian will decide the appropriate amount and dosage regimen. Such amount is referred to as an "effective" amount.

The term "sequence identity" refers to the extent to which two optimally aligned polynucleotide or polypeptide sequences are invariant throughout a window of alignment of components, e.g., nucleotides or amino acids. "Identity" can be readily calculated by known methods including, but not limited to, those described in: Computational Molecular Biology (Lesk, A. M., ed.) Oxford University Press, New York (1988); Biocomputing: Informatics and Genome Projects (Smith, D. W., ed.) Academic Press, New York (1993); Computer Analysis of Sequence Data, Part I (Griffin, A. M., and Griffin, H. G., eds.) Humana Press, New Jersey (1994); Sequence Analysis in Molecular Biology (von Heinje, G., ed.) Academic Press (1987); and Sequence Analysis Primer (Gribskov, M. and Devereux, J., eds.) Stockton Press, New York (1991); and the like.

An "identity fraction" for aligned segments of a test sequence and a reference sequence is the number of identical components which are shared by the two aligned sequences divided by the total number of components in the reference sequence segment, i.e., the entire reference sequence or a smaller defined part of the reference sequence. Percent sequence identity is typically represented as the identity fraction multiplied by 100. As used herein, the term "percent sequence identity" or "percent identity" refers to the percentage of identical nucleotides in a linear polynucleotide sequence of a reference ("query") polynucleotide molecule (or its complementary strand) as compared to a test ("subject") polynucleotide molecule (or its complementary strand) when the two sequences are optimally aligned (with appropriate nucleotide insertions, deletions, or gaps totaling less than 20 percent of the reference sequence over the window of comparison).

Optimal alignment of sequences for aligning a comparison window is well known to those skilled in the art and may be conducted by tools such as the local homology algorithm of Smith and Waterman, the homology alignment algorithm of Needleman and Wunsch, the search for similarity method of Pearson and Lipman, and optionally by computerized implementations of these algorithms such as GAP, BESTFIT, FASTA, and TFASTA available as part of the GCG® Wisconsin Package® (Accelrys Inc., Burlington, Mass.). The comparison of one or more polynucleotide sequences may be to a full-length polynucleotide sequence or a portion thereof, or to a longer polynucleotide sequence. In various embodiments "percent identity" may also be determined using BLASTX version 2.0 for translated nucleotide sequences and BLASTN version 2.0 for polynucleotide sequences.

The percent of sequence identity can be determined using the "Best Fit" or "Gap" program of the Sequence Analysis Software Package™ (Version 10; Genetics Computer Group, Inc., Madison, Wis.). "Gap" utilizes the algorithm of Needleman and Wunsch (1970) J. Mol. Biol. 48: 443-453, to find the alignment of two sequences that maximizes the number of matches and minimizes the number of gaps. "BestFit" performs an optimal alignment of the best segment of similarity between two sequences and inserts gaps to maximize the number of matches using the local homology algorithm of Smith and Waterman (1981) *Adv. Appl. Math.,* 2: 482-489, Smith et al. (1983) *Nucleic Acids Res.* 11: 2205-2220. Useful methods for determining sequence identity are also disclosed in Guide to Huge Computers (Martin J. Bishop, ed., Academic Press, San Diego (1994)), and Carillo et al. (1988) *Appl. Math,* 48: 1073). Certain illustrative computer programs for determining sequence identity include, but are not limited to, the Basic Local Alignment Search Tool (BLAST) programs, that are publicly available from National Center Biotechnology Information (NCBI) at the National Library of Medicine, National Institute of Health, Bethesda, Md. 20894; see BLAST Manual, Altschul et al., NCBI, NLM, NIH; (Altschul et al., J. Mol. Biol. 215:403-410 (1990)); version 2.0 or higher of BLAST programs allows the introduction of gaps (deletions and insertions) into alignments; for peptide sequence, BLASTX can be used to determine sequence identity; and for polynucleotide sequence, BLASTN can be used to determine sequence identity.

BRIEF DESCRIPTION OF THE DRAWINGS

FIG. 3A shows the average fold difference in titers for various ΔHS4 constructs (CCLc-βAS3-FB, CCLc-βAS3-FB-(HS4), and CCLc-βAS3–FB-(-HS4)(+HPRT)), while

FIG. 12 (bottom panel) shows average % mRNA/VCN produced using CCLc-βAS3-FB and CCLc-βAS3-(+Ank)-CoreLCR(Opti)-FB constructs.

FIG. 15B illustrates the nucleic acid sequence of the vector (SEQ ID NO:1).

FIG. 16B illustrates the nucleic acid sequence of the vector (SEQ ID NO:2).

FIG. 18A) CCLc-βAS3-FB-mGATA/ANK-CoreLCR Opti-ΔHS234/ΔIVS2. Note ΔIVS2 references an SspI (S) to RsaI (R) deletion (~220 bp), e.g., as described by Antoniou et al. (1998) *Nucl. Acids Res.,* 26(3): 721-729. FIG. 18B) CClC-βAS3-FB-CorLCR Opti-ANK. FIG. 18C) mGATA1-HS2 and the human ankyrin insulator elements in alternative configurations in combination with the "optimized mini-LCR (e.g., CCLc-βAS3-FB-CoreLCR Opti-mGATA/ANK).

DETAILED DESCRIPTION

Figure 1A:
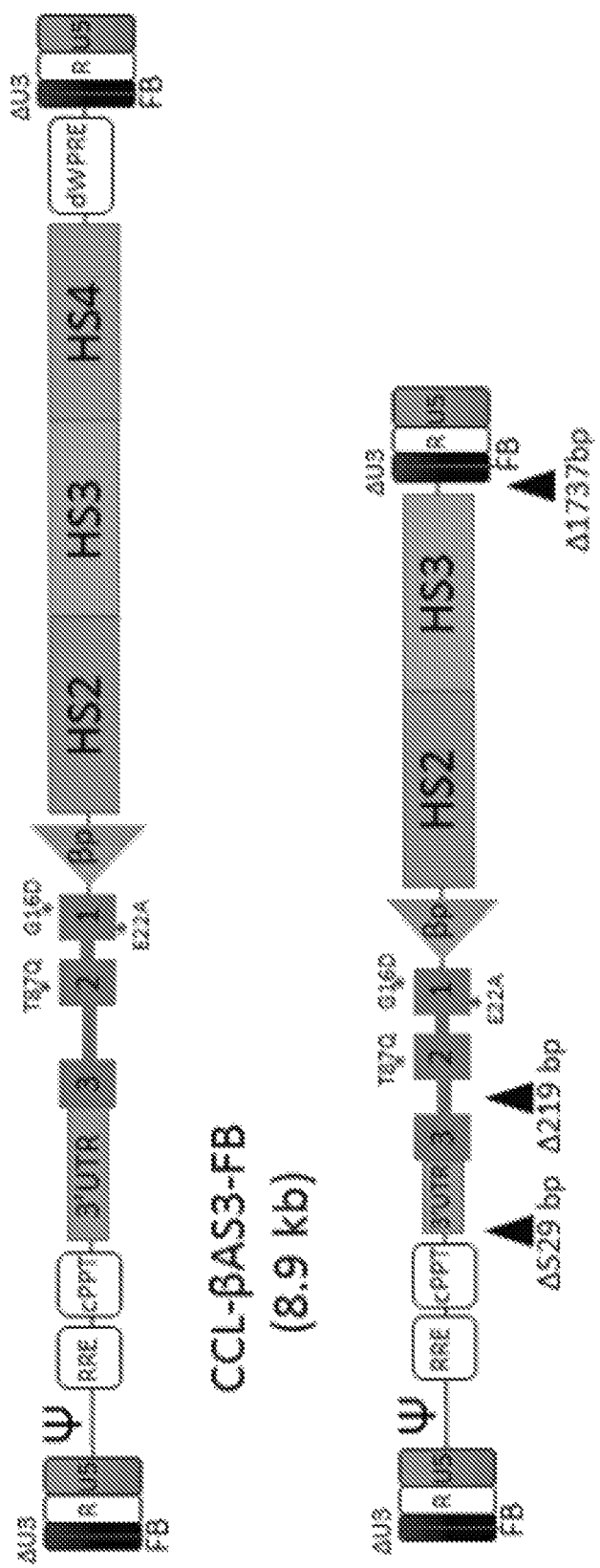
FIG. 1A schematically illustrates a comparison of the structures of CCL-βAS3-FB with CCL-GLOBE1-A53.

Sickle cell disease (SCD) is a multisystem disease, associated with severe episodes of acute illness and progressive organ damage, and is one of the most common monogenic disorders worldwide. Because SCD results from abnormalities in rbc, which in turn are produced from adult HSC, HSCT from a healthy (allogeneic) donor can benefit patients with SCD, by providing a source for life-long production of normal red blood cells. However, allogeneic HSCT is limited by the availability of well-matched donors and by immunological complications of graft rejection and graft-versus-host disease.

It is believed that autologous stem cell gene therapy for SCD has the potential to treat this illness without the need for immune suppression of current allogeneic HSCT approaches. In particular, it is believed that autologous stem cell gene therapy that introduces anti-sickling human beta globin into hematopoietic cells (or progenitors thereof) can provide effective therapy for SCD (including, for example, normalized rbc physiology and prevention of the manifestations of SCD).

Current B-globin expression vectors, however, suffer from low vector titer and sub-optimal gene transfer to hematopoietic stem cells, representing a major barrier toward the effective implementation of this gene therapy strategy to the clinic. In view of the data presented herein, it is believed that the predominant factor most likely affecting vector performance is overall vector length. We found that reduction of the "mini-LCR" by ~66% through redefining the LCR HS core sequences and, in certain embodiments, inclusion of the GATA1-H52 and/or Ankyrin insulator elements allowed for approximately 3-fold higher titer, superior gene transfer to hematopoietic stem cells and comparable expression of BAS3 when compared to the antecedent vector.

Accordingly, in various embodiments, an improved LV is provided for the introduction of a normal wild-type or an anti-sickling beta globin into stem and progenitor cells (e.g., hematopoietic stem and progenitor cells) that can then be transplanted into a subject in need thereof (e.g., a subject that has the sickle cell mutation).

We have engineered an optimized derivative of CCLc-βAS3-FB termed (CCLc-mGata/ANK-CoreLCR-βAS3-FB), that is capable of driving lineage-restricted expression of an anti-sickling B-globin like gene (βAS3). β-globin expression vectors generally contain fragments of the human β-globin Locus Control Region (LCR). The native LCR is a ~20 kilo base (kb) element that regulates the temporal and erythroid-specific expression of the globin gene cluster located nearly 30-60 kb upstream from the B-globin gene promoter sequences. Investigations conducted in the 1990's elucidated the function of the native LCR through examining the effect of sequence deletion on developmental erythropoiesis in murine mouse models. These mouse knockout studies utilized a limited repertoire of restriction enzymes to define and delete those sequences found to be essential for LCR function. It was later discovered that inclusion of these roughly defined LCR sequences, specifically hypersensitive sites (HS) HS2, HS3 and/or HS4, were essential to sustained, high-level and erythroid-specific expression of β-globin in the lentiviral vector system. Grouping the LCR's roughly defined HS2 (1.20 kb), HS3 (1.28 kb), and HS4 (1.1 kb) sequences together to form a "mini-LCR", faithfully conferred lineage-restricted expression of BAS3 to CCLc-βAS3-FB when placed upstream of a minimal promoter. However, the large size of the "mini-LCR" has a detrimental effect on packaging efficiency and gene transfer to human hematopoietic stem cells (HSC), limiting the effective deployment of this lentiviral vector to the clinic for gene therapy of hemoglobinopathies.

Optimization of the "mini-LCR" (with the primary goal of reducing length) was accomplished through redefining the putative boundaries of the LCR's HS core sequences using published genomic data available through ENCODE (Accessible via the UCSC Genome Browser). For example, the "Open Chromatin" track sets, which combine DNaseI hypersensitivity, Formaldehyde-Assisted Isolation of Regulatory Elements, and chromatin immunoprecipitation data to identify accessible chromatin regions, was combined with the "transcription Factor ChIP-seq" and "histone modification" track sets to generate new boundaries for the LCR's HS core sequences. These novel defined LCR HS core sequences (HS2(~420 bp), HS3(~340 bp), HS4(~410 bp)) were then used to replace the putative LCR HS sequences present within the "mini-LCR" (~3.6 kb reduced to ~1.1 kb) to produce an "optimized mini-LCR". In addition, we added elements to the "optimized mini-LCR" known to facilitate position independent expression of β-globin such as the murine GATA1-HS2 (~220 bp) and/or the human Ankyrin insulator (~150 bp) elements. These vectors, rationally-designed for reduced sizes of the LCR fragments and added transcriptional enhancing elements are believed to be produced at higher titers than the original β-globin lentiviral vector and have improved gene transfer to human HSC while retaining strong erythroid-specific gene expression. Such improved lentiviral vectors can be effective for gene therapy of hemoglobinopathies such as sickle cell disease and β-thalassemia.

In certain embodiments the lentiviral vectors (LVs) comprise an expression cassette comprising a nucleic acid construct comprising a human β-globin locus control region comprising at least one hypersensitive site (HS) core sequence selected from the group consisting of HS2 (~420 bp), HS3 (~340 bp), and HS4 (~410 bp), and a recombinant human beta globin gene encoding a beta globin polypeptide. Typically, the lentiviral vector is a TAT-independent and self-inactivating (SIN) lentiviral vector.

In certain embodiments the β-globin locus control region comprises hypersensitive site (HS) core sequence HS2. In certain embodiments the β-globin locus control region comprises hypersensitive site (HS) core sequence HS3. In certain embodiments the β-globin locus control region comprises hypersensitive site (HS) core sequence HS4. In certain embodiments the β-globin locus control region comprises hypersensitive site (HS) core sequences HS2 and HS3. In certain embodiments the β-globin locus control region comprises hypersensitive site (HS) core sequences HS2 and HS4. In certain embodiments the β-globin locus control region comprises hypersensitive site (HS) core sequences HS3 and HS4. In certain embodiments the β-globin locus control region comprises hypersensitive site (HS) core sequences HS2, HS3 and HS4.

In certain embodiments the HS2 core sequence consists of a nucleic acid sequence having having at least about 80%, or at least about 85%, or at least about 90%, or at least about 95%, or at least about 98% sequence identity with the sequence ranging from 5484 to 5908 of SEQ ID NO:1, or from 5077 to 5501 of SEQ ID NO: 2. In certain embodiments the HS2 core sequence consists of a nucleic acid sequence ranging from 5484 to 5908 of SEQ ID NO: 1, or from 5077 to 5501 of SEQ ID NO: 2.

In certain embodiments the HS3 core sequence consists of a nucleic acid sequence having at least about 80%, or at least about 85%, or at least about 90%, or at least about 95%, or at least about 98% sequence identity with the sequence ranging from 5909 to 6252 of SEQ ID NO: 1, or from 5502 to 5845 of SEQ ID NO:2. In certain embodiments the HS3 core sequence consists of a nucleic acid sequence ranging from 5909 to 6252 of SEQ ID NO: 1, or from 5502 to 5845 of SEQ ID NO: 2.

In certain embodiments the HS4 core sequence consists of a nucleic acid sequence having at least about 80%, or at least about 85%, or at least about 90%, or at least about 95%, or at least about 98% sequence identity with the sequence ranging from 6253 to 6662 of SEQ ID NO: 1, or from 5846 to 6255 of SEQ ID NO:2. In certain embodiments the HS4 core sequence consists of a nucleic acid sequence ranging from 6253 to 6662 of SEQ ID NO:1, or from 5846 to 6255 of SEQ ID NO: 2.

In certain embodiments the β-globin locus control region comprises the nucleic acid sequence ranging from 5484 to 6662 of SEQ ID NO:1, or from 5077 to 6255 of SEQ ID NO: 2. In certain embodiments the human β-globin locus control region consists of the nucleic acid sequence ranging from 5484 to 6662 of SEQ ID NO: 1, or from 5077 to 6255 of SEQ ID NO:2.

In certain embodiments, one or more of the HS core sequences can be used in combination with a full-length (e.g., wildtype) HS sequence. Thus, for example, in certain embodiments, a core HS2 may be used in combination with a core HS3, or with a wildtype HS3, or with a core HS4 or a wildtype HS4, or with a core HS3 and a wildtype HS4, or with a wildtype HS3 and a core HS4. In certain embodiments, a core HS3 may be used in combination with a core HS2, or with a wildtype HS2, or with a core HS4 or a wildtype HS4, or with a core HS2 and a wildtype HS4, or with a wildtype HS2 and a core HS4. Thus, for example, in certain embodiments, a core HS4 may be used in combination with a core HS2, or with a wildtype HS2, or with a core HS3 or a wildtype HS3, or with a core HS2 and a wildtype HS3, or with a wildtype HS2 and a core HS3. In certain embodiments an HS4 is absent. Accordingly, the present hypersensitive sites can be a core HS2, and a core HS3, or a wildtype HS2 and a core HS3, or a core HS2 and a wildtype HS3. In certain embodiments, particularly where a mGATA1q-HS2 and/or human ankyrin insulator element is present, the hypersensitive sites can comprise or consist of a wildtype HS3 and a wildtype HS2.

In certain embodiments the human beta globin gene in the vectors contemplated herein comprises an anti-sickling human beta globin gene encoding an anti-sickling beta globin polypeptide. In certain embodiments the anti-sickling version of a human beta globin gene used in the vector comprises one, two, or three mutations selected from the group consisting of Gly16Asp, Glu22Ala and Thr87Gln (see, e.g., Levasseur (2004) *J. Biol. Chem.* 279(26): 27518-27524). Without being bound to a particular theory, it is believed the Glu22Ala mutation increases affinity to α-chain, the Thr87Gln mutation blocks lateral contact with Val6 of βS protein, and the Gly16Asp mutation decreases axial contact between globin chains.

In certain embodiments the vectors described herein comprise a human Ankyrin insulator element. In certain embodiments the Ankyrin insulator element comprises a nucleic acid sequence having at least 90%, or at least 95%, or at least 98% sequence identity with the sequence ranging from 5325 to 5483 of SEQ ID NO:1, or from 6458 to 6616 of SEQ ID NO:2. In certain embodiments the human Ankyrin insulator element consists of a nucleic acid sequence ranging from 5325 to 5483 of SEQ ID NO:1, or from 6458 to 6616 of SEQ ID NO:2.

In certain embodiments the vectors described herein comprise a murine GATA1-HS2. In certain embodiments the murine GATA1-HS2 (mGATA-HS2) comprises a nucleic acid sequence having at least 90%, or at least 95%, or at least 98% sequence identity with the sequence ranging from 6256 to 6457 SEQ ID NO:2. In certain embodiments the murine GATA1-HS2 consists of the nucleic acid sequence ranging from 6256 to 6457 SEQ ID NO: 2.

In various embodiments, the LVs described herein can have additional safety features not included in previous β-globin encoding lentiviral constructs. In certain embodiments, these features include the presence of an insulator (e.g., an FB insulator in the 3'LTR). Additionally, or alternatively, in certain embodiments, the HIV LTR has been substituted with an alternative promoter (e.g., a CMV) to yield a higher titer vector without the inclusion of the HIV TAT protein during packaging. Other strong promoters (e.g., RSV, and the like can also be used).

Figure 15A:
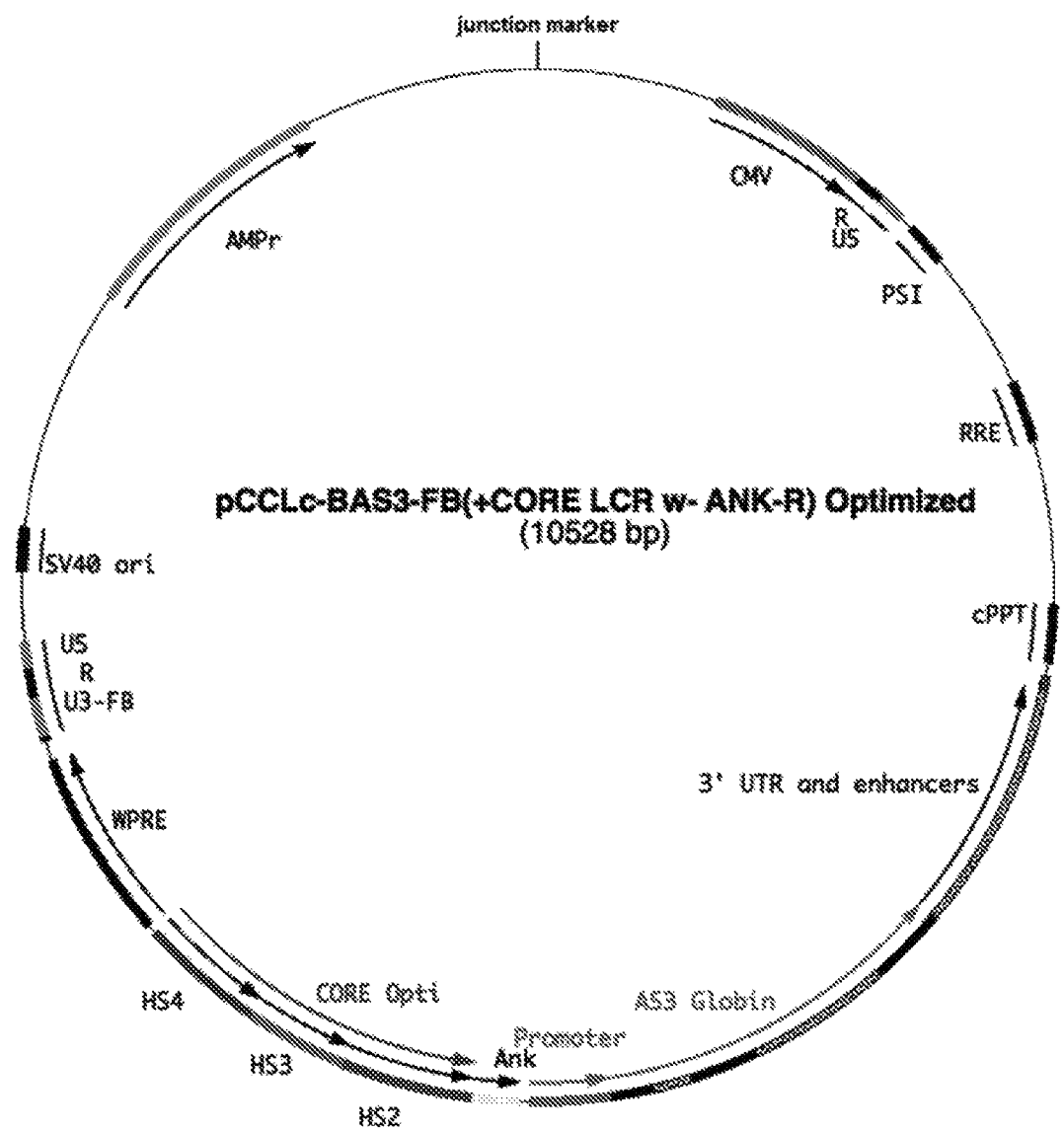
FIG. 15A schematically illustrates the pCCLC-βAS3-FB (+CoreLCR w-Ank-R) optimized vector ((10528 bp).

In certain embodiments the vectors contemplated herein include the various elements shown in the vector illustrated in FIG. 15A. In certain embodiments the vectors contemplated herein comprise the nucleic acid shown in FIG. 15B (SEQ ID NO:1).

Figure 16A:
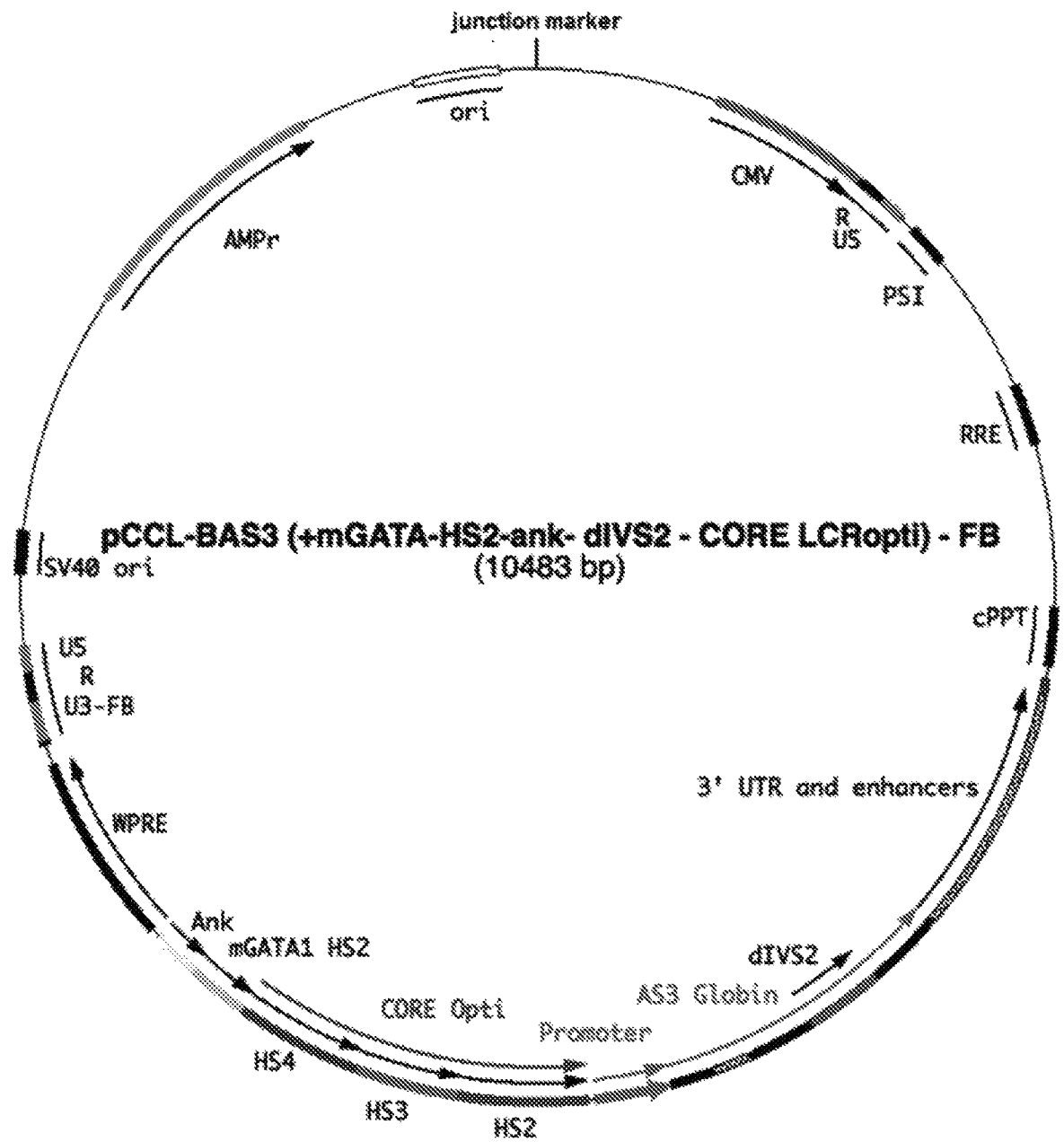
FIG. 16A illustrates the pCCL-βAS3-(+mGATA-HS2-Ank-dIVS2-CoreLCRopti)-FB optimized vector (10483 bp).

In certain embodiments the vectors contemplated herein include the various elements shown in the vector illustrated in FIG. 16A. In certain embodiments the vectors contemplated herein comprise the nucleic acid shown in FIG. 16B (SEQ ID NO:2). include the various elements shown in the vector illustrated in FIG. 15A.

As shown in the Examples provided herein the vectors described herein are effective to transduce cells at high titer and to also provide high levels of expression.

In view of these results, it is believed that LVs described herein, e.g., recombinant TAT-independent, SIN LVs that express a human beta-globin gene can be used to effectively treat hemoglobinopathies in subjects (e.g., human and non-human mammals). Such hemoglobinopathies include, but are not limited to sickle cell disease (SCD) and β-thalassemia. It is believed these vectors can be used for the modification of stem cells (e.g., hematopoietic stem and progenitor cells) that can be introduced into a subject in need thereof for the treatment of, e.g., SCD or β-thalassemia. Moreover, it appears that the resulting cells will produce enough of the transgenic β-globin protein to demonstrate significant improvement in subject health. It is also believed the vectors can be directly administered to a subject to achieve in vivo transduction of the target (e.g., hematopoietic stem or progenitor cells) and thereby also effect a treatment of subjects in need thereof.

As noted above, in various embodiments the LVs described herein can comprise various safety features. For example, the HIV LTR has been substituted with a CMV promoter to yield higher titer vector without the inclusion of the HIV TAT protein during packaging. In certain embodiments an insulator (e.g., the FB insulator) is introduced into the 3'LTR for safety. The LVs are also constructed to provide efficient transduction and high titer.

It will be appreciated that the foregoing elements are illustrative and need not be limiting. In view of the teachings provided herein, suitable substitutions for these elements will be recognized by one of skill in the art and are contemplated within the scope of the teachings provided herein.

Anti-Sickling Beta Globin Gene and Expression Cassette.

As indicated above, in various embodiments the LV described herein comprise an expression cassette encoding a wild-type β-globin gene, or an anti-sickling human β-globin gene. On illustrative, but non-limiting cassette is βAS3 which comprises an ~2.3 kb recombinant human β-globin gene (exons and introns) with three amino acid substitutions (Thr87Gln; Gly16Asp; and Glu22A1a) under the control of transcriptional control elements (e.g., the human β-globin gene 5' promoter (e.g., ~266 bp), the human β-globin 3' enhancer (e.g., ~260 bp), β-globin intron 2 with a ~375 bp RsaI deletion from IVS2, and a ~3.4 kb composite human β-globin locus control region (e.g., HS2~1203 bp; HS3~1213 bp; HS4-954 bp). One embodiment of a βAS3 cassette is described by Levasseur (2003) *Blood* 102: 4312-4319.

In certain embodiments the β-globin gene comprises an an SspI (S) to RsaI (R) deletion (~220 bp), e.g., as described by Antoniou et al. 1998) *Nucl. Acids Res.*, 26(3): 721-729 (see, e.g., pCCL-BAS3-FB(+CORE ΔIVS2) optimized, SEQ ID NO:3).

The βAS3 cassette, however, is illustrative and need not be limiting. Using the known cassette described herein (see, e.g., Example 1), numerous variations will be available to one of skill in the art. Such variations include, for example, use of a gene encoding a wild-type β-globin, use of a gene comprising one or two mutations selected from the group consisting of Thr87Gln, Gly16Asp, and Glu22Ala, and/or further or alternative mutations to the β-globin to further enhance non-sickling properties, alterations in the transcriptional control elements (e.g., promoter and/or enhancer), variations on the intron size/structure, and the like.

TAT-Independent and Self Inactivating Lentiviral Vectors.

To further improve safety, in various embodiments, the LVs described herein comprise a TAT-independent, self-inactivating (SIN) configuration. Thus, in various embodiments it is desirable to employ in the LVs described herein an LTR region that has reduced promoter activity relative to wild-type LTR. Such constructs can be provided that are effectively "self-inactivating" (SIN) which provides a biosafety feature. SIN vectors are ones in which the production of full-length vector RNA in transduced cells is greatly reduced or abolished altogether. This feature minimizes the risk that replication-competent recombinants (RCRs) will emerge. Furthermore, it reduces the risk that that cellular coding sequences located adjacent to the vector integration site will be aberrantly expressed.

Furthermore, a SIN design reduces the possibility of interference between the LTR and the promoter that is driving the expression of the transgene. SIN LVs can often permit full activity of the internal promoter.

The SIN design increases the biosafety of the LVs. The majority of the HIV LTR is comprised of the U3 sequences. The U3 region contains the enhancer and promoter elements that modulate basal and induced expression of the HIV genome in infected cells and in response to cell activation. Several of these promoter elements are essential for viral replication. Some of the enhancer elements are highly conserved among viral isolates and have been implicated as critical virulence factors in viral pathogenesis. The enhancer elements may act to influence replication rates in the different cellular target of the virus As viral transcription starts at the 3' end of the U3 region of the 5' LTR, those sequences are not part of the viral mRNA and a copy thereof from the 3' LTR acts as template for the generation of both LTR's in the integrated provirus. If the 3' copy of the U3 region is altered in a retroviral vector construct, the vector RNA is still produced from the intact 5' LTR in producer cells, but cannot be regenerated in target cells. Transduction of such a vector results in the inactivation of both LTR's in the progeny virus. Thus, the retrovirus is self-inactivating (SIN) and those vectors are known as SIN transfer vectors.

In certain embodiments self-inactivation is achieved through the introduction of a deletion in the U3 region of the 3' LTR of the vector DNA, i.e., the DNA used to produce the vector RNA. During RT, this deletion is transferred to the 5' LTR of the proviral DNA. Typically, it is desirable to eliminate enough of the U3 sequence to greatly diminish or abolish altogether the transcriptional activity of the LTR, thereby greatly diminishing or abolishing the production of full-length vector RNA in transduced cells. However, it is generally desirable to retain those elements of the LTR that are involved in polyadenylation of the viral RNA, a function typically spread out over U3, R and U5. Accordingly, in certain embodiments, it is desirable to eliminate as many of the transcriptionally important motifs from the LTR as possible while sparing the polyadenylation determinants.

The SIN design is described in detail in Zufferey et al. (1998) *J Virol.* 72(12): 9873-9880, and in U.S. Pat. No. 5,994,136. As described therein, there are, however, limits to the extent of the deletion at the 3' LTR. First, the 5' end of the U3 region serves another essential function in vector transfer, being required for integration (terminal dinucleotide+att sequence). Thus, the terminal dinucleotide and the att sequence may represent the 5' boundary of the U3 sequences which can be deleted. In addition, some loosely defined regions may influence the activity of the downstream polyadenylation site in the R region. Excessive deletion of U3 sequence from the 3'LTR may decrease polyadenylation of vector transcripts with adverse consequences both on the titer of the vector in producer cells and the transgene expression in target cells.

Additional SIN designs are described in U.S. Patent Publication No: 2003/0039636. As described therein, in certain embodiments, the lentiviral sequences removed from the LTRs are replaced with comparable sequences from a non-lentiviral retrovirus, thereby forming hybrid LTRs. In particular, the lentiviral R region within the LTR can be replaced in whole or in part by the R region from a non-lentiviral retrovirus. In certain embodiments, the lentiviral TAR sequence, a sequence which interacts with TAT protein to enhance viral replication, is removed, preferably in whole, from the R region. The TAR sequence is then replaced with a comparable portion of the R region from a non-lentiviral retrovirus, thereby forming a hybrid R region. The LTRs can be further modified to remove and/or replace with non-lentiviral sequences all or a portion of the lentiviral U3 and U5 regions.

Accordingly, in certain embodiments, the SIN configuration provides a retroviral LTR comprising a hybrid lentiviral R region that lacks all or a portion of its TAR sequence, thereby eliminating any possible activation by TAT, wherein the TAR sequence or portion thereof is replaced by a comparable portion of the R region from a non-lentiviral retrovirus, thereby forming a hybrid R region. In a particular embodiment, the retroviral LTR comprises a hybrid R region, wherein the hybrid R region comprises a portion of the HIV R region (e.g., a portion comprising or consisting of the nucleotide sequence shown in SEQ ID NO: 10 in US 2003/0039636) lacking the TAR sequence, and a portion of the MoMSV R region (e.g., a portion comprising or consisting of the nucleotide sequence shown in SEQ ID NO: 9 in 2003/0039636) comparable to the TAR sequence lacking from the HIV R region. In another particular embodiment, the entire hybrid R region comprises or consists of the nucleotide sequence shown in SEQ ID NO: 11 in 2003/0039636.

Suitable lentiviruses from which the R region can be derived include, for example, HIV (HIV-1 and HIV-2), EIV, SIV and FIV. Suitable retroviruses from which non-lentiviral sequences can be derived include, for example, MoMSV, MoMLV, Friend, MSCV, RSV and Spumaviruses. In one illustrative embodiment, the lentivirus is HIV and the non-lentiviral retrovirus is MoMSV.

In another embodiment described in US 2003/0039636, the LTR comprising a hybrid R region is a left (5') LTR and further comprises a promoter sequence upstream from the hybrid R region. Preferred promoters are non-lentiviral in origin and include, for example, the U3 region from a non-lentiviral retrovirus (e.g., the MoMSV U3 region). In one particular embodiment, the U3 region comprises the nucleotide sequence shown in SEQ ID NO: 12 in US 2003/0039636. In another embodiment, the left (5') LTR further comprises a lentiviral U5 region downstream from the hybrid R region. In one embodiment, the U5 region is the HIV U5 region including the HIV att site necessary for genomic integration. In another embodiment, the U5 region comprises the nucleotide sequence shown in SEQ ID NO: 13 in US 2003/0039636. In yet another embodiment, the entire left (5') hybrid LTR comprises the nucleotide sequence shown in SEQ ID NO: 1 in US 2003/0039636.

In another illustrative embodiment, the LTR comprising a hybrid R region is a right (3') LTR and further comprises a modified (e.g., truncated) lentiviral U3 region upstream from the hybrid R region. The modified lentiviral U3 region can include the att sequence, but lack any sequences having promoter activity, thereby causing the vector to be SIN in that viral transcription cannot go beyond the first round of replication following chromosomal integration. In a particular embodiment, the modified lentiviral U3 region upstream from the hybrid R region consists of the 3' end of a lentiviral (e.g., HIV) U3 region up to and including the lentiviral U3 att site. In one embodiment, the U3 region comprises the nucleotide sequence shown in SEQ ID NO: 15 in US 2003/0039636. In another embodiment, the right (3') LTR further comprises a polyadenylation sequence downstream from the hybrid R region. In another embodiment, the polyadenylation sequence comprises the nucleotide sequence shown in SEQ ID NO: 16 in US 2003/0039636. In yet another embodiment, the entire right (5') LTR comprises the nucleotide sequence shown in SEQ ID NO: 2 or 17 of US 2003/0039636.

Thus, in the case of HIV based LV, it has been discovered that such vectors tolerate significant U3 deletions, including the removal of the LTR TATA box (e.g., deletions from −418 to −18), without significant reductions in vector titers. These deletions render the LTR region substantially transcriptionally inactive in that the transcriptional ability of the LTR in reduced to about 90% or lower.

It has also been demonstrated that the trans-acting function of Tat becomes dispensable if part of the upstream LTR in the transfer vector construct is replaced by constitutively active promoter sequences (see, e.g., Dull et al. (1998) *J Virol.* 72(11): 8463-8471. Furthermore, we show that the expression of rev in trans allows the production of high-titer HIV-derived vector stocks from a packaging construct which contains only gag and pol. This design makes the expression of the packaging functions conditional on complementation available only in producer cells. The resulting gene delivery system, conserves only three of the nine genes of HIV-1 and relies on four separate transcriptional units for the production of transducing particles.

In one embodiments illustrated in Example 1, the cassette expressing an anti-sickling β-globin (e.g., βAS3) is placed in the pCCL LV backbone, which is a SIN vector with the CMV enhancer/promoter substituted in the 5' LTR.

It will be recognized that the CMV promoter typically provides a high level of non-tissue specific expression. Other promoters with similar constitutive activity include, but are not limited to the RSV promoter, and the SV40 promoter. Mammalian promoters such as the beta-actin promoter, ubiquitin C promoter, elongation factor lapromoter, tubulin promoter, etc., may also be used.

The foregoing SIN configurations are illustrative and non-limiting. Numerous SIN configurations are known to those of skill in the art. As indicated above, in certain embodiments, the LTR transcription is reduced by about 95% to about 99%. In certain embodiments LTR may be rendered at least about 90%, at least about 91%, at least about 92%, at least about 93%, at least about 94%, at least about 95% at least about 96%, at least about 97%, at least about 98%, or at least about 99% transcriptionally inactive.

Insulator Element

In certain embodiments, to further enhance biosafety, insulators are inserted into the LV described herein. Insulators are DNA sequence elements present throughout the genome. They bind proteins that modify chromatin and alter regional gene expression. The placement of insulators in the vectors described herein offer various potential benefits including, inter alia: 1) Shielding of the vector from positional effect variegation of expression by flanking chromosomes (i.e., barrier activity); and 2) Shielding flanking chromosomes from insertional trans-activation of gene expression by the vector (enhancer blocking). Thus, insulators can help to preserve the independent function of genes or transcription units embedded in a genome or genetic context in which their expression may otherwise be influenced by regulatory signals within the genome or genetic context (see, e.g., Burgess-Beusse et al. (2002) *Proc. Natl. Acad. Sci. USA,* 99: 16433; and Zhan et al. (2001) *Hum. Genet.,* 109: 471). In the present context insulators may contribute to protecting lentivirus-expressed sequences from integration site effects, which may be mediated by cis-acting elements present in genomic DNA and lead to deregulated expression of transferred sequences. In various embodiments LVs are provided in which an insulator sequence is inserted into one or both LTRs or elsewhere in the region of the vector that integrates into the cellular genome.

The first and best characterized vertebrate chromatin insulator is located within the chicken β-globin locus control region. This element, which contains a DNase-I hypersensitive site-4 (cHS4), appears to constitute the 5' boundary of the chicken β-globin locus (Prioleau et al. (1999) *EMBO J.* 18: 4035-4048). A 1.2-kb fragment containing the cHS4 element displays classic insulator activities, including the ability to block the interaction of globin gene promoters and enhancers in cell lines (Chung et al. (1993) *Cell,* 74: 505-514), and the ability to protect expression cassettes in *Drosophila* (Id.), transformed cell lines (Pikaart et al. (1998) *Genes Dev.* 12: 2852-2862), and transgenic mammals (Wang et al. (1997) *Nat. Biotechnol.,* 15: 239-243; Taboit-Dameron et al. (1999) *Transgenic Res.,* 8: 223-235) from position effects. Much of this activity is contained in a 250-bp fragment. Within this stretch is a 49-bp cHS4 core (Chung et al. (1997) *Proc. Natl. Acad. Sci., USA,* 94: 575-580) that interacts with the zinc finger DNA binding protein CTCF implicated in enhancer-blocking assays (Bell et al. (1999) *Cell,* 98: 387-396).

One illustrative and suitable insulator is FB (FII/BEAD-A), a 77 bp insulator element, that contains the minimal CTCF binding site enhancer-blocking components of the chicken β-globin 5' HS4 insulators and a homologous region from the human T-cell receptor alpha/delta blocking element alpha/delta I (BEAD-I) insulator described by Ramezani et al. (2008) *Stem Cell* 26: 3257-3266. The FB "synthetic" insulator has full enhancer blocking activity. This insulator is illustrative and non-limiting. Other suitable insulators may be used including, for example, the full length chicken beta-globin HS4 or insulator sub-fragments thereof, the ankyrin gene insulator, and other synthetic insulator elements.

Packaging Signal.

In various embodiments the vectors described herein further comprise a packaging signal. A "packaging signal," "packaging sequence," or "psi sequence" is any nucleic acid sequence sufficient to direct packaging of a nucleic acid whose sequence comprises the packaging signal into a retroviral particle. The term includes naturally occurring packaging sequences and also engineered variants thereof. Packaging signals of a number of different retroviruses, including lentiviruses, are known in the art.

Rev Responsive Element (RRE).

In certain embodiments the LVs described herein comprise a Rev response element (RRE) to enhance nuclear export of unspliced RNA. RREs are well known to those of skill in the art. Illustrative RREs include, but are not limited to RREs such as that located at positions 7622-8459 in the HIV NL4-3 genome (Genbank accession number AF003887) as well as RREs from other strains of HIV or other retroviruses. Such sequences are readily available from Genbank or from the database with URL hiv-web.lanl.gov/content/index.

Central PolyPurine Tract (cPPT).

In various embodiments the vectors described herein further include a central polypurine tract. Insertion of a fragment containing the central polypurine tract (cPPT) in lentiviral (e.g., HIV-1) vector constructs is known to enhance transduction efficiency drastically, reportedly by facilitating the nuclear import of viral cDNA through a central DNA flap.

Expression-Stimulating Posttranscriptional Regulatory Element (PRE)

In certain embodiments the LVs described herein may comprise any of a variety of posttranscriptional regulatory elements (PREs) whose presence within a transcript increases expression of the heterologous nucleic acid (e.g., βAS3) at the protein level. PREs may be particularly useful in certain embodiments, especially those that involve lentiviral constructs with modest promoters.

One type of PRE is an intron positioned within the expression cassette, which can stimulate gene expression. However, introns can be spliced out during the life cycle events of a lentivirus. Hence, if introns are used as PRE's they are typically placed in an opposite orientation to the vector genomic transcript.

Posttranscriptional regulatory elements that do not rely on splicing events offer the advantage of not being removed during the viral life cycle. Some examples are the posttranscriptional processing element of herpes simplex virus, the posttranscriptional regulatory element of the hepatitis B virus (HPRE) and the woodchuck hepatitis virus (WPRE). Of these the WPRE is typically preferred as it contains an additional cis-acting element not found in the HPRE. This regulatory element is typically positioned within the vector so as to be included in the RNA transcript of the transgene, but outside of stop codon of the transgene translational unit.

The WPRE is characterized and described in U.S. Pat. No. 6,136,597. As described therein, the WPRE is an RNA export element that mediates efficient transport of RNA from the nucleus to the cytoplasm. It enhances the expression of transgenes by insertion of a cis-acting nucleic acid sequence, such that the element and the transgene are contained within a single transcript. Presence of the WPRE in the sense orientation was shown to increase transgene expression by up to 7- to 10-fold. Retroviral vectors transfer sequences in the form of cDNAs instead of complete intron-containing genes as introns are generally spliced out during the sequence of events leading to the formation of the retroviral particle. Introns mediate the interaction of primary transcripts with the splicing machinery. Because the processing of RNAs by the splicing machinery facilitates their cytoplasmic export, due to a coupling between the splicing and transport machineries, cDNAs are often inefficiently expressed. Thus, the inclusion of the WPRE in a vector results in enhanced expression of transgenes.

Transduced Host Cells and Methods of Cell Transduction.

The recombinant LV and resulting virus described herein are capable of transferring a nucleic acid (e.g., a nucleic acid encoding an anti-sickling β-globin) sequence into a mammalian cell. For delivery to cells, vectors of the present invention are preferably used in conjunction with a suitable packaging cell line or co-transfected into cells in vitro along with other vector plasmids containing the necessary retroviral genes (e.g., gag and pol) to form replication incompetent virions capable of packaging the vectors of the present invention and infecting cells.

The recombinant LVs and resulting virus described herein are capable of transferring a nucleic acid (e.g., a nucleic acid encoding an anti-sickling β-globin) sequence into a mammalian cell. For delivery to cells, vectors of the present invention are preferably used in conjunction with a suitable packaging cell line or co-transfected into cells in vitro along with other vector plasmids containing the necessary retroviral genes (e.g., gag and pol) to form replication incompetent virions capable of packaging the vectors of the present invention and infecting cells.

Typically, the vectors are introduced via transfection into the packaging cell line. The packaging cell line produces viral particles that contain the vector genome. Methods for transfection are well known by those of skill in the art. After cotransfection of the packaging vectors and the transfer vector to the packaging cell line, the recombinant virus is recovered from the culture media and tittered by standard methods used by those of skill in the art. Thus, the packaging constructs can be introduced into human cell lines by calcium phosphate transfection, lipofection or electroporation, generally together with a dominant selectable marker, such as neomycin, DHFR, Glutamine synthetase, followed by selection in the presence of the appropriate drug and isolation of clones. In certain embodiments the selectable marker gene can be linked physically to the packaging genes in the construct.

Stable cell lines wherein the packaging functions are configured to be expressed by a suitable packaging cell are known (see, e.g., U.S. Pat. No. 5,686,279, which describes packaging cells). In general, for the production of virus particles, one may employ any cell that is compatible with the expression of lentiviral Gag and Pol genes, or any cell that can be engineered to support such expression. For example, producer cells such as 293T cells and HT1080 cells may be used.

The packaging cells with a lentiviral vector incorporated in them form producer cells. Producer cells are thus cells or cell-lines that can produce or release packaged infectious viral particles carrying the therapeutic gene of interest (e.g., modified β-globin). These cells can further be anchorage dependent which means that these cells will grow, survive, or maintain function optimally when attached to a surface such as glass or plastic. Some examples of anchorage dependent cell lines used as lentiviral vector packaging cell lines when the vector is replication competent are HeLa or 293 cells and PERC.6 cells.

Accordingly, in certain embodiments, methods are provided of delivering a gene to a cell which is then integrated into the genome of the cell, comprising contacting the cell with a virion containing a lentiviral vector described herein. The cell (e.g., in the form of tissue or an organ) can be contacted (e.g., infected) with the virion ex vivo and then delivered to a subject (e.g., a mammal, animal or human) in which the gene (e.g., anti-sickling β-globin) will be expressed. In various embodiments the cell can be autologous to the subject (i.e., from the subject) or it can be non-autologous (i.e., allogeneic or xenogenic) to the subject. Moreover, because the vectors described herein are capable of being delivered to both dividing and non-dividing cells, the cells can be from a wide variety including, for example, bone marrow cells, mesenchymal stem cells (e.g., obtained from adipose tissue), and other primary cells derived from human and animal sources. Alternatively, the virion can be directly administered in vivo to a subject or a localized area of a subject (e.g., bone marrow).

Of course, as noted above, the lentivectors described herein will be particularly useful in the transduction of human hematopoietic progenitor cells or a hematopoietic stem cells, obtained either from the bone marrow, the peripheral blood or the umbilical cord blood, as well as in the transduction of a $CD4^+$ T cell, a peripheral blood B or T lymphocyte cell, and the like. In certain embodiments particularly preferred targets are $CD34^+$ cells.

Gene Therapy.

In still other embodiments, the present invention is directed to a method for transducing a human hematopoietic stem cell comprising contacting a population of human cells that include hematopoietic stem cells with one of the foregoing lentivectors under conditions to effect the transduction of a human hematopoietic progenitor cell in said population by the vector. The stem cells may be transduced in vivo or in vitro, depending on the ultimate application. Even in the context of human gene therapy, such as gene therapy of human stem cells, one may transduce the stem cell in vivo or, alternatively, transduce in vitro followed by infusion of the transduced stem cell into a human subject. In one aspect of this embodiment, the human stem cell can be removed from a human, e.g., a human patient, using methods well known to those of skill in the art and transduced as noted above. The transduced stem cells are then reintroduced into the same or a different human.

Stem Cell/Progenitor Cell Gene Therapy.

In various embodiments the lentivectors described herein are particularly useful for the transduction of human hematopoietic progenitor cells or haematopoietic stem cells (HSCs), obtained either from the bone marrow, the peripheral blood or the umbilical cord blood, as well as in the transduction of a $CD4^+$ T cell, a peripheral blood B or T lymphocyte cell, and the like. In certain embodiments particularly preferred targets are $CD34^+$ cells.

When cells, for instance $CD34^+$ cells, dendritic cells, peripheral blood cells or tumor cells are transduced ex vivo, the vector particles are incubated with the cells using a dose generally in the order of between 1 to 50 multiplicities of infection (MOI) which also corresponds to $1 \times 10^5$ to $50 \times 10^5$ transducing units of the viral vector per $10^5$ cells. This can include amounts of vector corresponding to 1, 2, 3, 4, 5, 6, 7, 8, 9, 10, 15, 20, 25, 30, 35, 40, 45, and 50 MOI. Typically, the amount of vector may be expressed in terms of HeLa transducing units (TU).

In certain embodiments cell-based therapies involve providing stem cells and/or hematopoietic precursors, transduce the cells with the lentivirus encoding, e.g., an anti-sickling human β-globin, and then introduce the transformed cells into a subject in need thereof (e.g., a subject with the sickle cell mutation).

In certain embodiments the methods involve isolating population of cells, e.g., stem cells from a subject, optionally expand the cells in tissue culture, and administer the lentiviral vector whose presence within a cell results in production of an anti-sickling β-globin in the cells in vitro. The cells are then returned to the subject, where, for example, they may provide a population of red blood cells that produce the anti-sickling β globin.

In some embodiments of the invention, a population of cells, which may be cells from a cell line or from an individual other than the subject, can be used. Methods of isolating stem cells, immune system cells, etc., from a subject and returning them to the subject are well known in the art. Such methods are used, e.g., for bone marrow transplant, peripheral blood stem cell transplant, etc., in patients undergoing chemotherapy.

Where stem cells are to be used, it will be recognized that such cells can be derived from a number of sources including bone marrow (BM), cord blood (CB) CB, mobilized peripheral blood stem cells (mPBSC), and the like. In certain embodiments the use of induced pluripotent stem cells (IPSCs) is contemplated. Methods of isolating hematopoietic stem cells (HSCs), transducing such cells and introducing them into a mammalian subject are well known to those of skill in the art.

In certain embodiments a lentiviral vector described herein (see, e.g., FIGS. 15A, and 16A) is used in stem cell gene therapy for SCD by introducing the βAS3 anti-sickling beta-globin gene into the bone marrow stem cells of patients with sickle cell disease followed by autologous transplantation.

Direct Introduction of Vector.

In certain embodiments direct treatment of a subject by direct introduction of the vector(s) described herein is contemplated. The lentiviral compositions may be formulated for delivery by any available route including, but not limited to parenteral (e.g., intravenous), intradermal, subcutaneous, oral (e.g., inhalation), transdermal (topical), transmucosal, rectal, and vaginal. Commonly used routes of delivery include inhalation, parenteral, and transmucosal.

In various embodiments pharmaceutical compositions can include an LV in combination with a pharmaceutically acceptable carrier. As used herein the language "pharmaceutically acceptable carrier" includes solvents, dispersion media, coatings, antibacterial and antifungal agents, isotonic and absorption delaying agents, and the like, compatible with pharmaceutical administration. Supplementary active compounds can also be incorporated into the compositions.

In some embodiments, active agents, i.e., a lentiviral described herein and/or other agents to be administered together the vector, are prepared with carriers that will protect the compound against rapid elimination from the body, such as a controlled release formulation, including implants and microencapsulated delivery systems. Biodegradable, biocompatible polymers can be used, such as ethylene vinyl acetate, polyanhydrides, polyglycolic acid, collagen, polyorthoesters, and polylactic acid. Methods for preparation of such compositions will be apparent to those skilled in the art. Suitable materials can also be obtained commercially from Alza Corporation and Nova Pharmaceuticals, Inc. Liposomes can also be used as pharmaceutically acceptable carriers. These can be prepared according to methods known to those skilled in the art, for example, as described in U.S. Pat. No. 4,522,811. In some embodiments the composition is targeted to particular cell types or to cells that are infected by a virus. For example, compositions can be targeted using monoclonal antibodies to cell surface markers, e.g., endogenous markers or viral antigens expressed on the surface of infected cells.

It is advantageous to formulate compositions in dosage unit form for ease of administration and uniformity of dosage. Dosage unit form as used herein refers to physically discrete units suited as unitary dosages for the subject to be treated; each unit comprising a predetermined quantity of a LV calculated to produce the desired therapeutic effect in association with a pharmaceutical carrier.

A unit dose need not be administered as a single injection but may comprise continuous infusion over a set period of time. Unit dose of the LV described herein may conveniently be described in terms of transducing units (T.U.) of lentivector, as defined by titering the vector on a cell line such as HeLa or 293. In certain embodiments unit doses can range from $10^3$, $10^4$, $10^5$, $10^6$, $10^7$, $10^8$, $10^9$, $10^{10}$, $10^{11}$, $10^{12}$, $10^{13}$ T.U. and higher.

Pharmaceutical compositions can be administered at various intervals and over different periods of time as required, e.g., one time per week for between about 1 to about 10 weeks; between about 2 to about 8 weeks; between about 3 to about 7 weeks; about 4 weeks; about 5 weeks; about 6 weeks, etc. It may be necessary to administer the therapeutic composition on an indefinite basis. The skilled artisan will appreciate that certain factors can influence the dosage and timing required to effectively treat a subject, including but not limited to the severity of the disease or disorder, previous treatments, the general health and/or age of the subject, and other diseases present. Treatment of a subject with a LV can include a single treatment or, in many cases, can include a series of treatments.

Exemplary doses for administration of gene therapy vectors and methods for determining suitable doses are known in the art. It is furthermore understood that appropriate doses of a LV may depend upon the particular recipient and the mode of administration. The appropriate dose level for any particular subject may depend upon a variety of factors including the age, body weight, general health, gender, and diet of the subject, the time of administration, the route of administration, the rate: of excretion, other administered therapeutic agents, and the like.

In certain embodiments lentiviral gene therapy vectors can be delivered to a subject by, for example, intravenous injection, local administration, or by stereotactic injection (see, e.g., Chen et al. (1994) *Proc. Natl. Acad. Sci. USA*, 91: 3054). In certain embodiments vectors may be delivered orally or inhalationally and may be encapsulated or otherwise manipulated to protect them from degradation, enhance uptake into tissues or cells, etc. Pharmaceutical preparations can include a LV in an acceptable diluent, or can comprise a slow release matrix in which a LV is imbedded. Alternatively or additionally, where a vector can be produced intact from recombinant cells, as is the case for retroviral or lentiviral vectors as described herein, a pharmaceutical preparation can include one or more cells which produce vectors. Pharmaceutical compositions comprising a LV described herein can be included in a container, pack, or dispenser, optionally together with instructions for administration.

The foregoing compositions, methods and uses are intended to be illustrative and not limiting. Using the teachings provided herein other variations on the compositions, methods and uses will be readily available to one of skill in the art.

EXAMPLES

The following examples are offered to illustrate, but not to limit the claimed invention.

Example 1

Development of Next Generation Vectors for Gene Therapy of Sickle Cell Disease

Autologous hematopoietic stem cell gene therapy is an approach to treating sickle cell disease (SCD) patients that may result in lower morbidity than allogeneic transplantation. We previously examined the potential of a LV (CCL-βAS3-FB) encoding a human beta-globin (HBB) gene engineered to impede sickle hemoglobin polymerization (HBBAS3) to transduce human BM CD34$^+$ cells from SCD donors and prevent sickling of rbc produced by in vitro differentiation (see, e.g., U.S. Patent Pub. No: 2015/0224209; PCT Pub. No: WO 2014/043131; Romero et al. (2013) *J. Clin. Invest.*, 128(8): 3317-3330)). The CCL-βAS3-FB LV transduced BM CD34$^+$ cells from either healthy or SCD donors at similar levels, based on quantitative PCR and colony-forming unit progenitor analysis. Consistent expression of HBBAS3 mRNA and HbAS3 protein compromised a fourth of the total β-globin-like transcripts and Hb tetramers. Upon deoxygenation, a lower percentage of HBBAS3-transduced rbc exhibited sickling compared with mock-transduced cells from sickle donors. Transduced BM CD34$^+$ cells were transplanted into immunodeficient mice, and the human cells recovered after 2-3 months were cultured for erythroid differentiation, which showed levels of HBBAS3 mRNA similar to those seen in the CD34$^+$ cells that were directly differentiated in vitro. These results demonstrated that the CCL-βAS3-FB LV is capable of efficient transfer and consistent expression of an effective antisickling β-globin gene in human SCD BM CD34$^+$ progenitor cells, improving physiologic parameters of the resulting rbc.

Figure 1B:
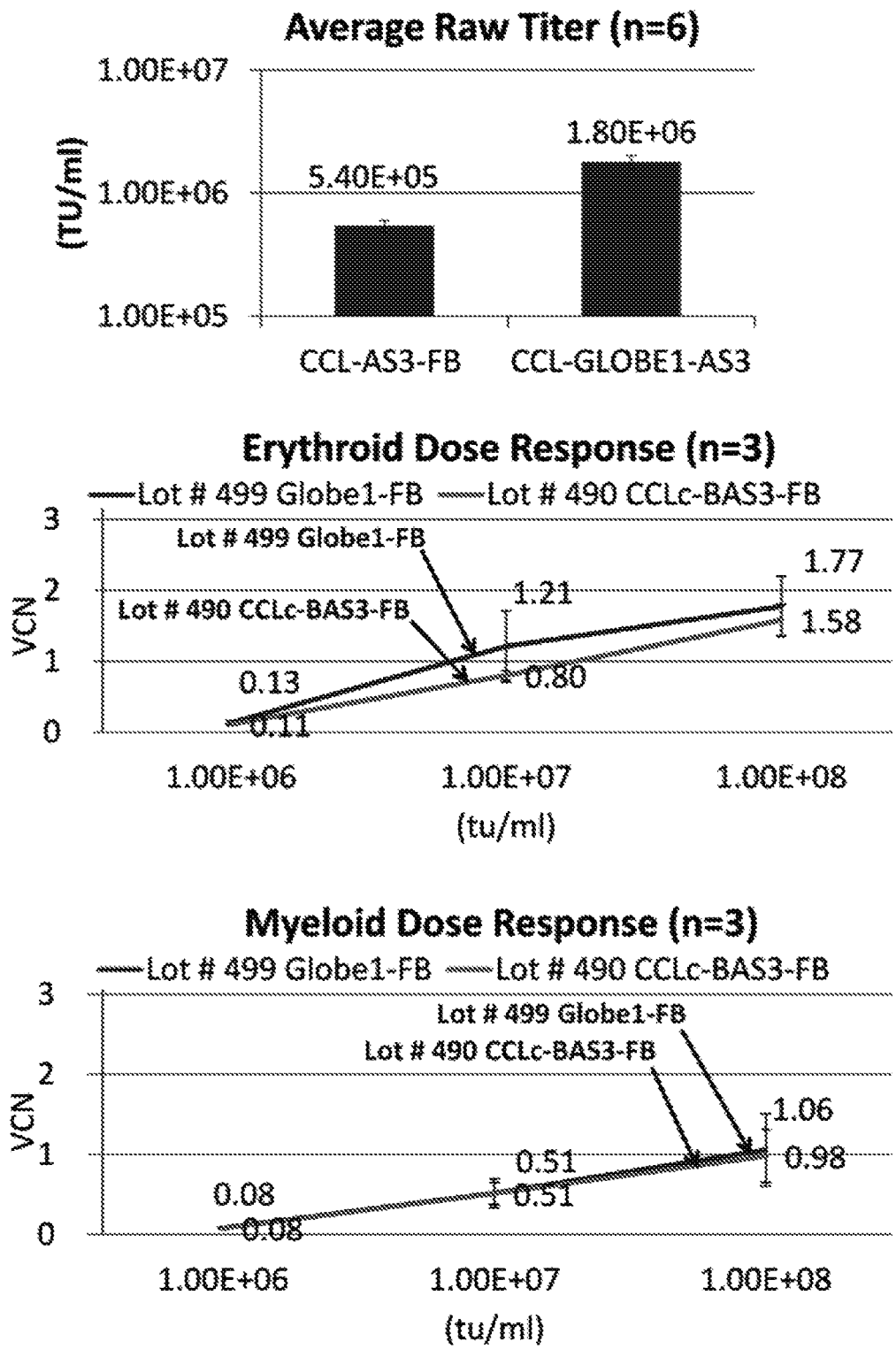
FIG. 1B shows a comparison of the two vectors with respect to raw titer (top) and transduction in erythroid (middle) and myeloid (bottom) cell lines. VCN=vector copy number FIG. 2 schematically illustrates various strategies investigated in designing a series of CCLc-βAS3-FB derivatives.

In an effort to further improve vector performance, we initially evaluated the CCL-βAS3-FB construct (see, FIG. 1A) and compared it to the smaller CCL-GLOBE1-βAS3 construct (see, FIG. 1B; Miccio et al. (2008) *Proc. Natl. Acad. Sci. USA*, 10547-10552). In particular, raw titers were evaluated as well as the erythroid dose response and myeloid dose response (see, FIG. 1B). CCL-βAS3-FB showed a significantly lower average raw titer (FIG. 1B, top panel), however, erythroid dose response (FIG. 1B, middle panel) was marginally higher for GLOBE1-βAS3 and the myeloid dose response was essentially the same for both constructs (FIG. 1B, bottom panel).

Figure 2:
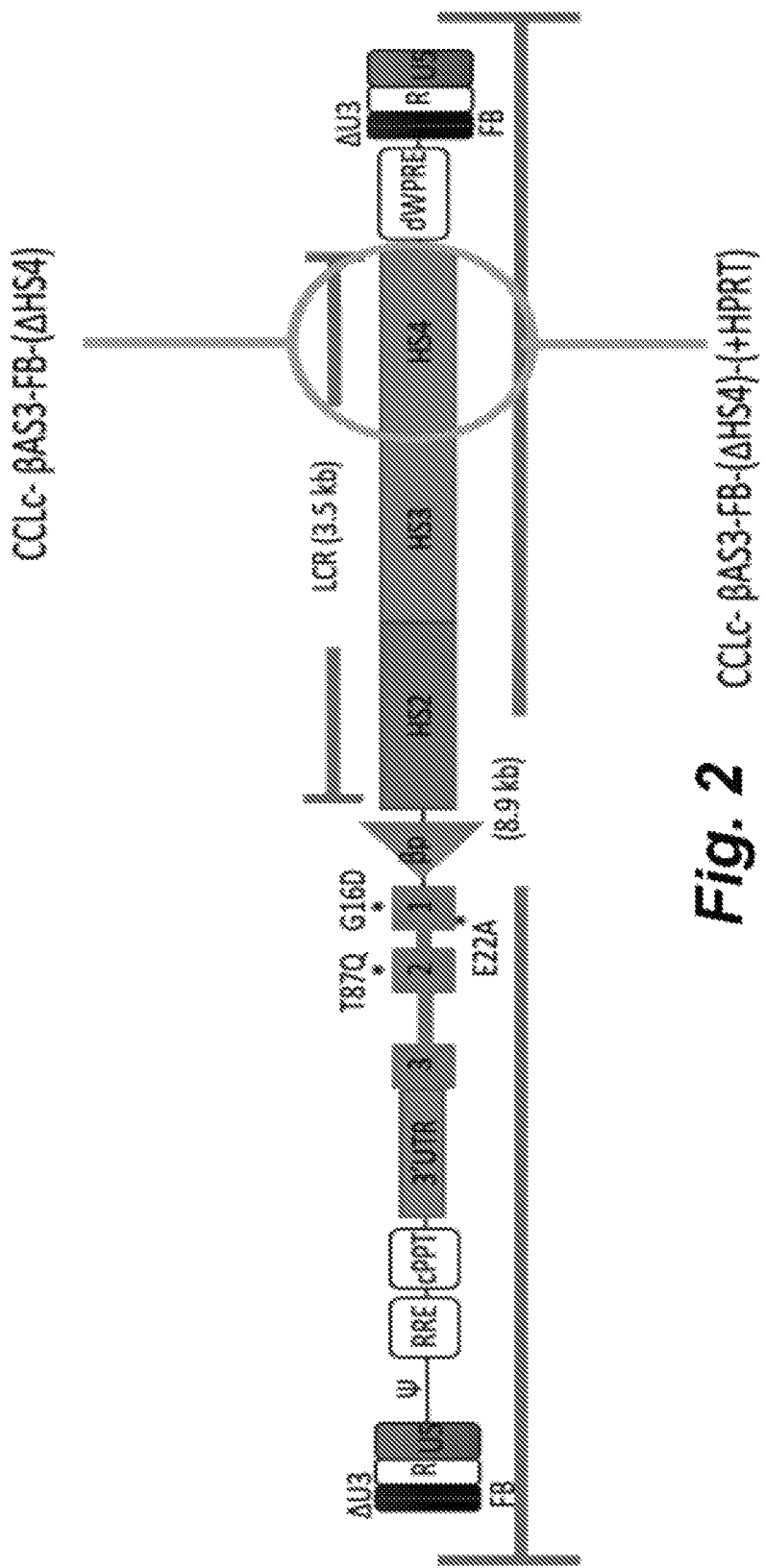

To investigate whether overall vector size impacts titer or gene transfer more than the presence of discrete sequences, a series of CCLc-βAS3-FB derivative were designed as illustrated in FIG. 2. These included, but were not limited to deletions of HS4 (e.g., CCLc-βAS3-FB(ΔHS4), elimination of WPRE (e.g., CCLc-βAS3-FB-(ΔWPRE), deletions of both HS4 and WPRE (e.g., CCLc-βAS3-FB-(ΔHS4/ΔWPRE), deletion of HS4 and insertion of a spacer element therefor (e.g., CCLc-βAS3-FB-(ΔHS4)-(+HPRT), elimination of IVS2 (e.g., CCLc-βAS3-FB-(ΔIVS2), and the like.

Figure 3A:
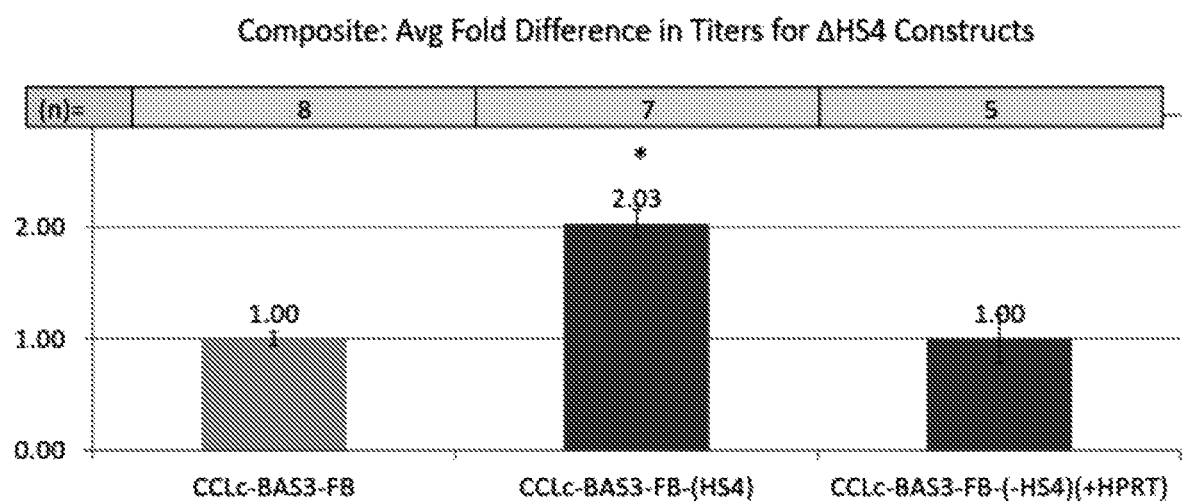
Figure 3B:
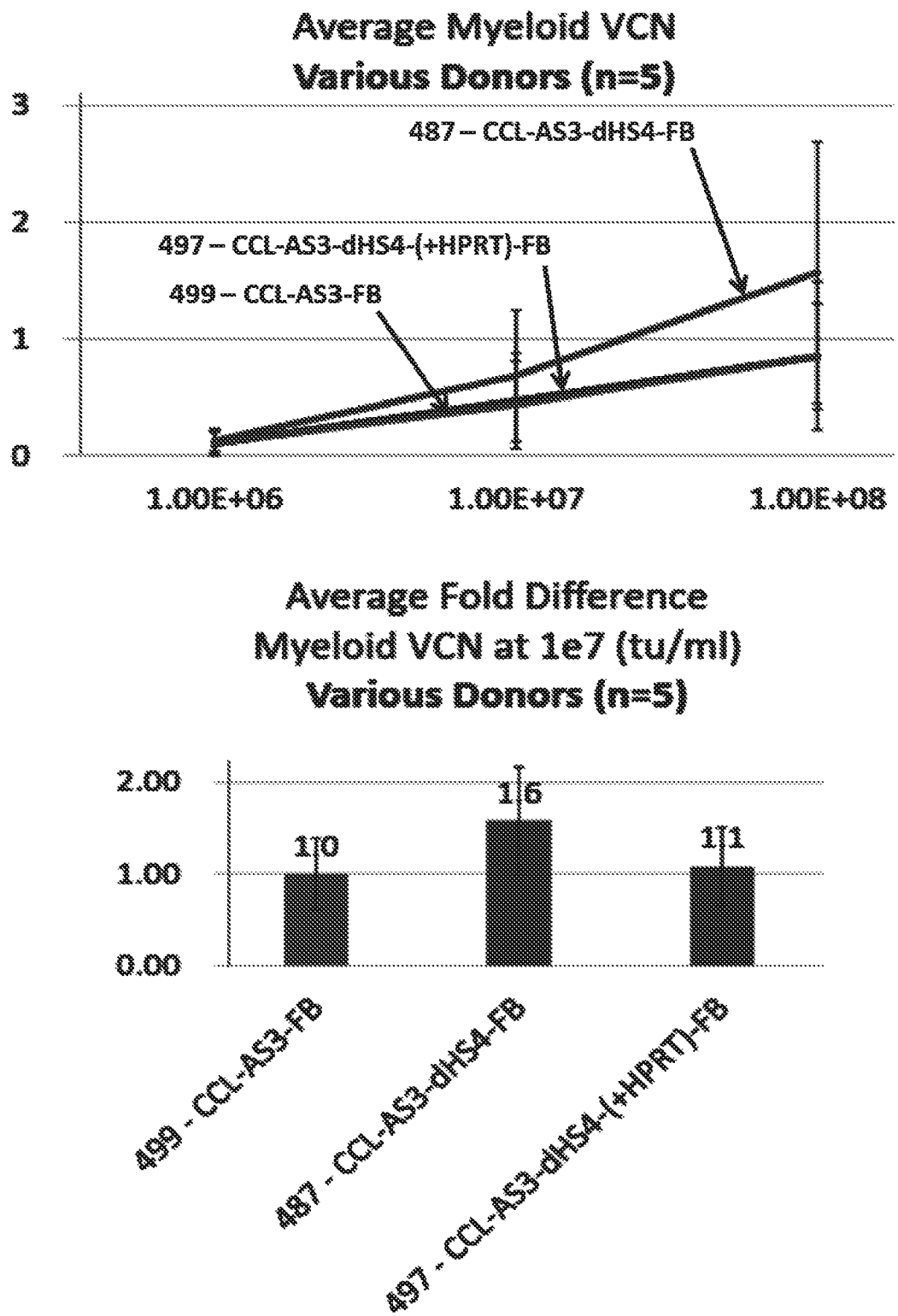
FIG. 3B shows the effect of vector length on gene transfer and FIG. 3C shows the expression levels of the various constructs.
Figure 3C:
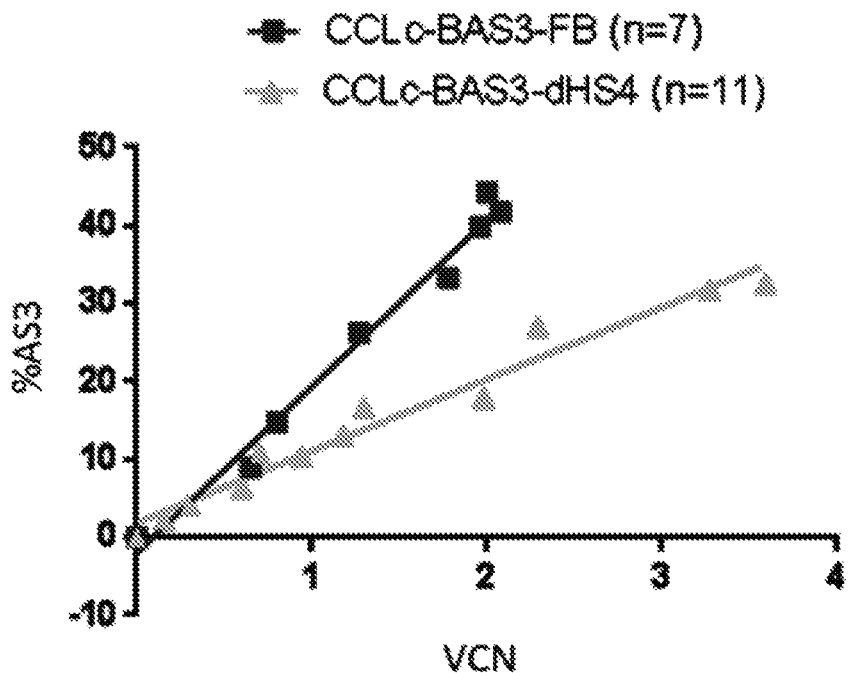
Figure 3C:
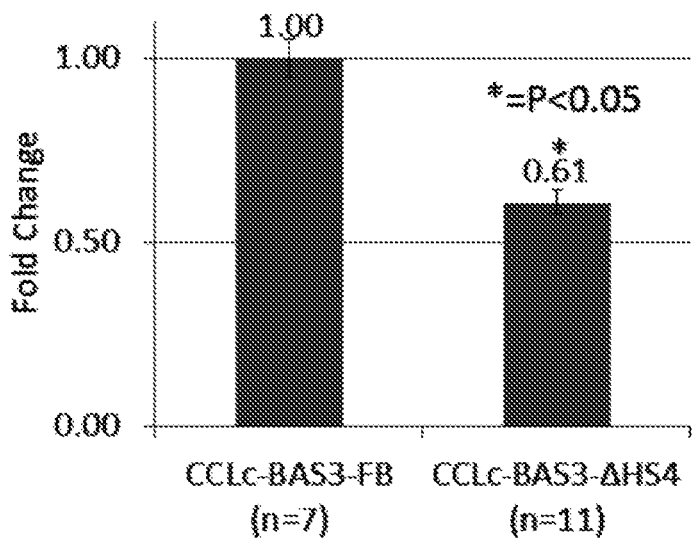

FIG. 3A shows the average fold difference in titers for various ΔHS4 constructs. As shown, reduction of length via removal of HS4 improves titer. FIG. 3B shows the effect of vector length on gene transfer to HSC. As shown, a reduction in vector length improves gene transfer as well. FIG. 3C shows the effect of vector length (CCLc-βAS3-FB versus CCLc-βAS3-(ΔHS4) on expression level. As shown while a reduction in vector length improves titer and gene transfer, removal of HS4 impaired expression.

In conclusion it appears that reduction of vector length through deletion of HS4 improved tier and gene transfer, but impaired expression. Moreover, replacing HS4 with HPRT stuffer (1.1 kb) did not improve titer or gene transfer suggesting that size is the predominant factor influencing titer and perhaps gene transfer.

Figure 4:
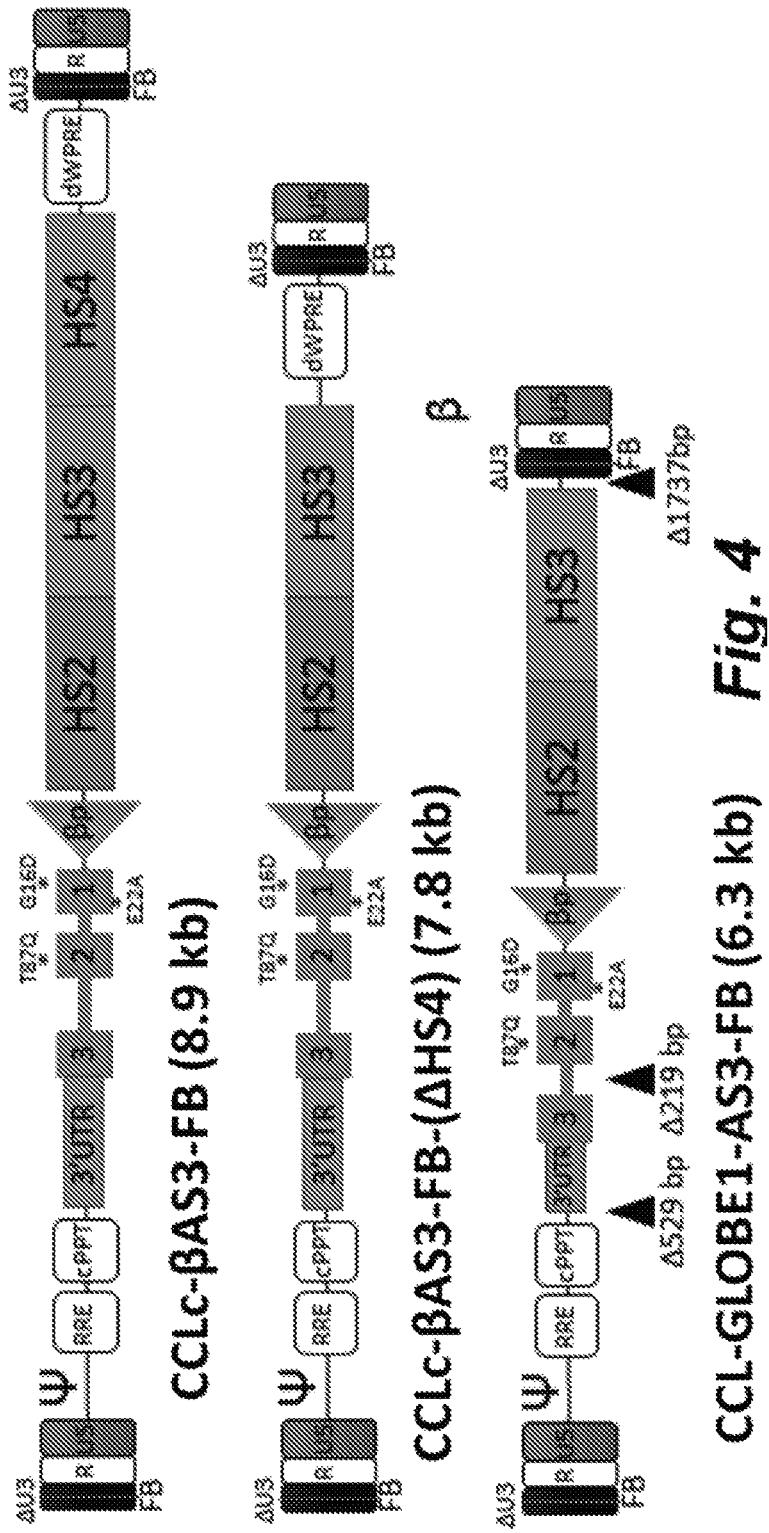
FIG. 4 schematically illustrates the structure of CCLc-βAS3-FB (8.9 kb) (top), CCLc-βAS3-FB-(ΔHS4) (6.3 kb) (middle), and CCL-GLOBE1-AS3 (6.3 kb) (bottom).

To further explore this, we compared the performance of three constructs of different length: 1) CCLc-βAS3-FB (8.9 kb), 2) CCLc-βAS3-FB-(ΔHS4) (6.3 kb), and 3) CCL-GLOBE1-AS3 (6.3 kb). The structures of these three constructs are illustrated in FIG. 4.

Figure 5A:
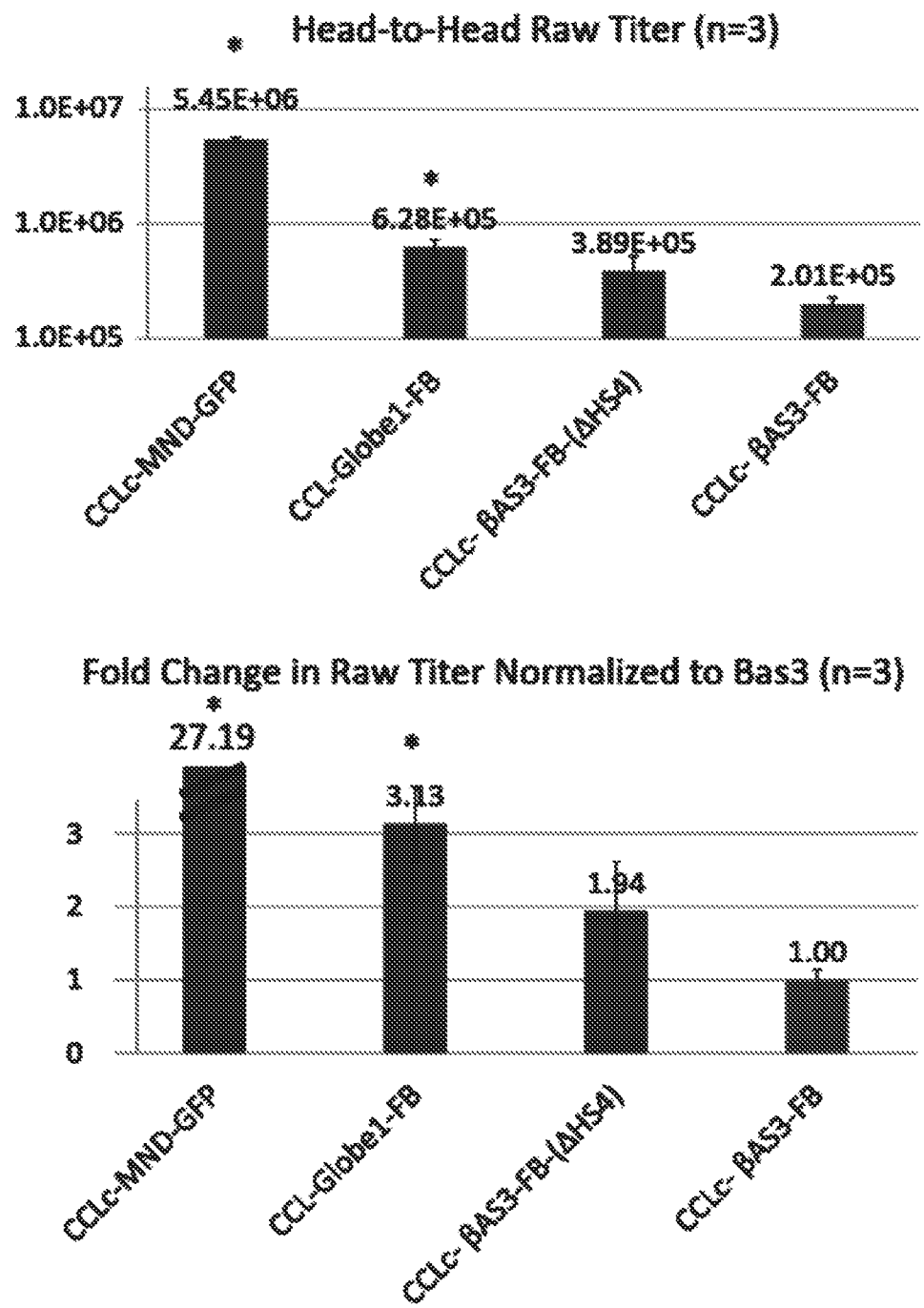
FIG. 5A-5C illustrate the titers of CCLc-Globe1-FB, CCLc-βAS3-FB-(ΔHS4), and CCLC-βAS3-FB (FIG. 5A), the transduction levels of these vectors (FIG. 5B), and expression levels (FIG. 5C).
Figure 5B:
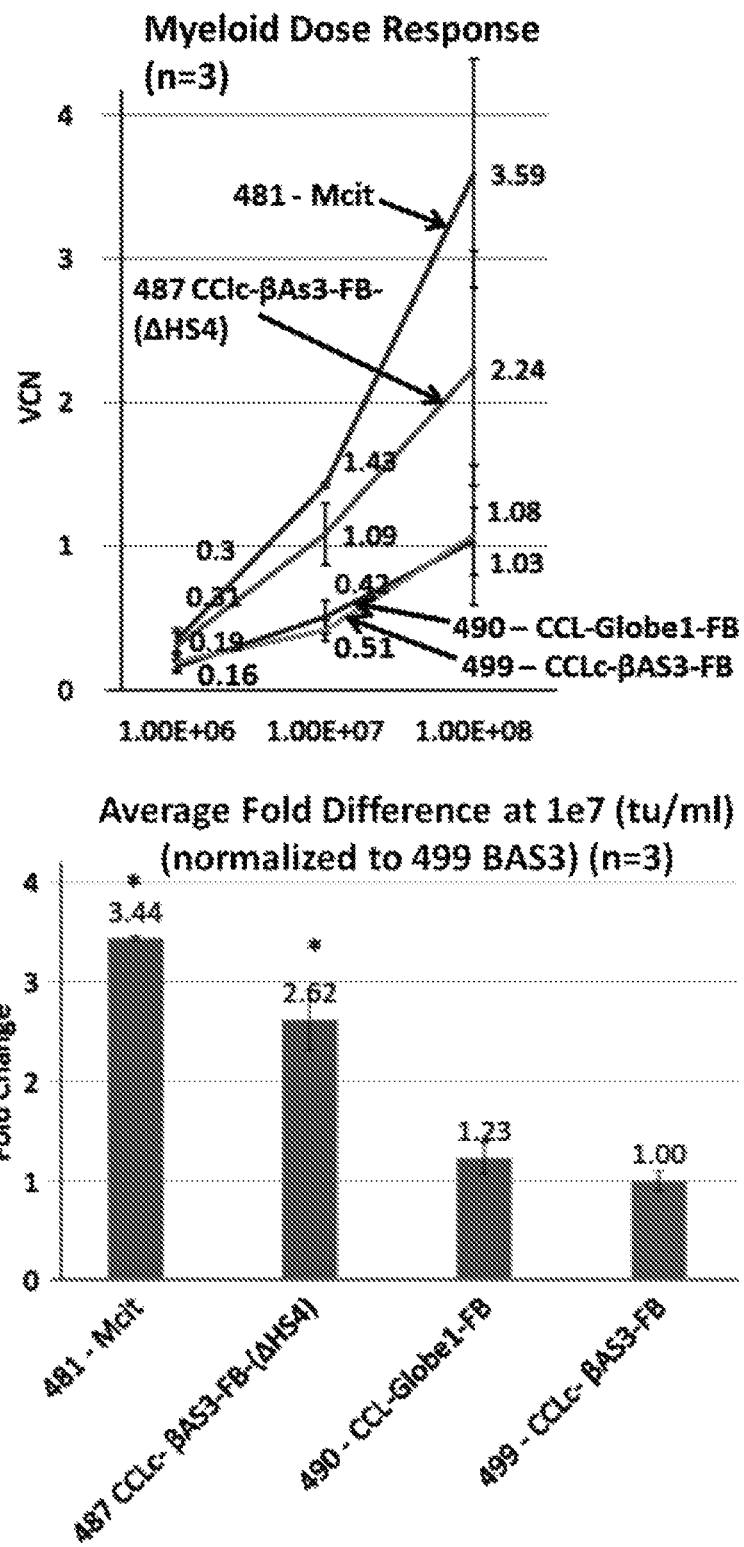
Figure 5C:
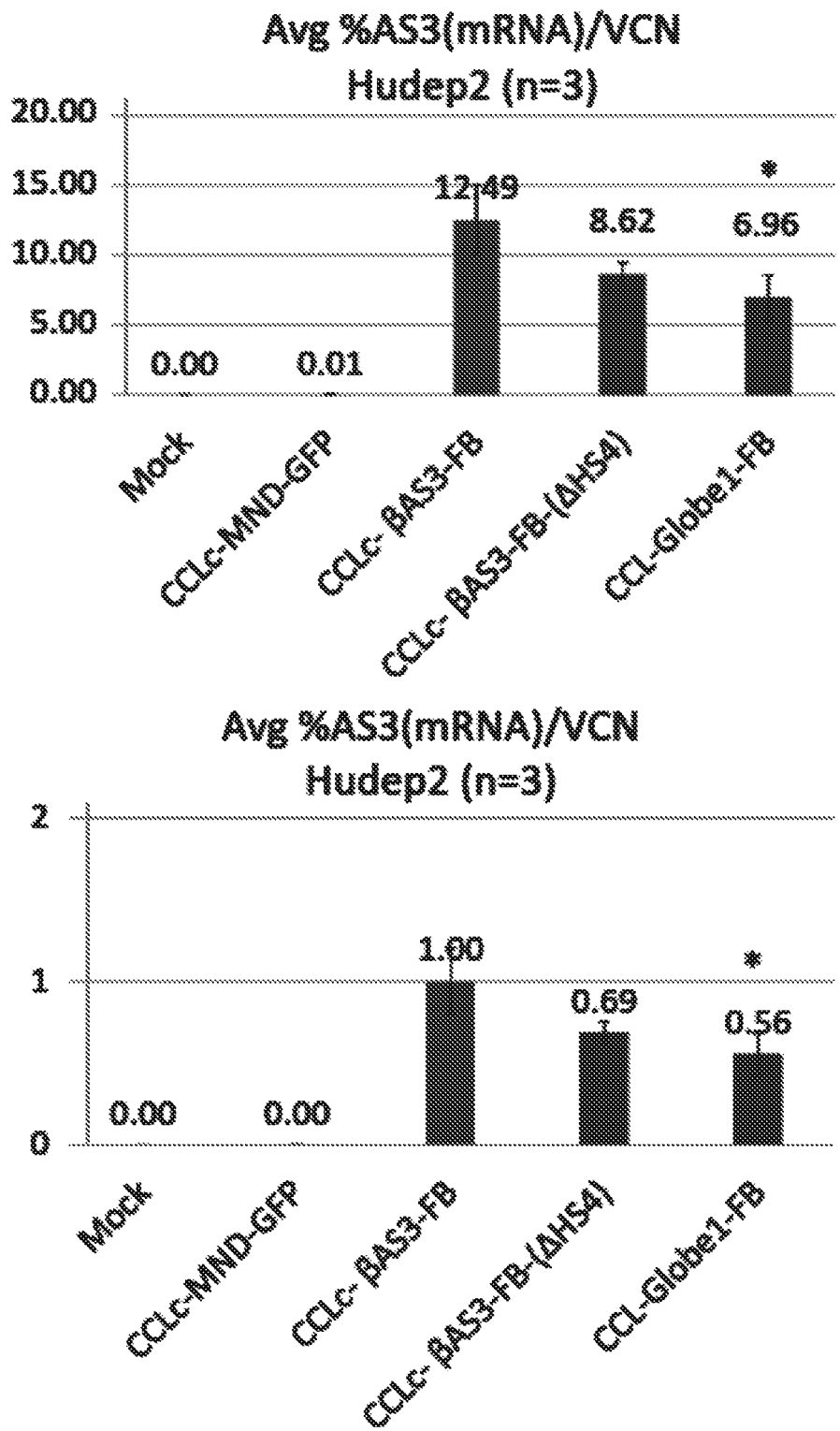

The titer of each of these vectors is shown in FIG. 5A, while transduction levels are shown in FIG. 5B, and expression levels in FIG. 5C. Expression levels are also summarized below in Table 1.

TABLE 1

Expression levels of CCLc-βAS3-FB (8.9 kb), CCLc-βAS3-FB-(ΔHS4) (6.3 kb), and CCL-GLOBE1-AS3 (6.3 kb).

|  | 481-GFP | 499-CCLc-βAS3-FB | 487 CCLc-βAS3-FB-(ΔHS4) | 490-CCL-Globe1-FB |
|---|---|---|---|---|
| % BAS3(mRNA)/VCN | 0.0 | 12.5 | 8.6 | 7 |
| Std. Dev. | 0.0 | 2.5 | 0.8 | 1.6 |

Figure 6A:
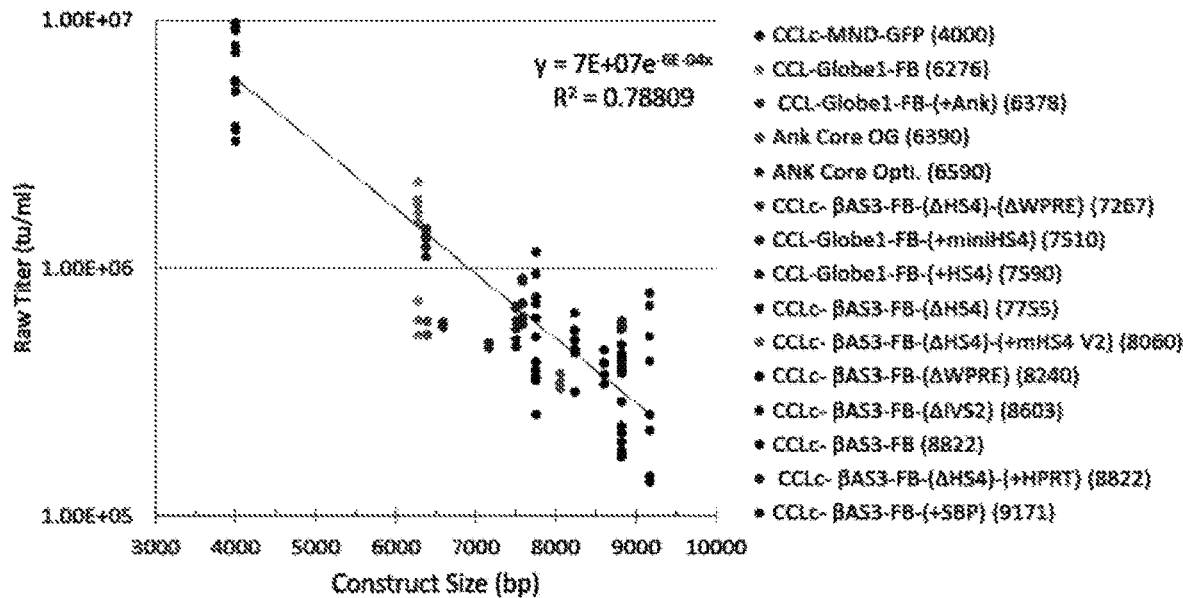
FIG. 6A shows the raw titers plotted as a function of construct size for 15 different lentiviral constructs.
Figure 6B:
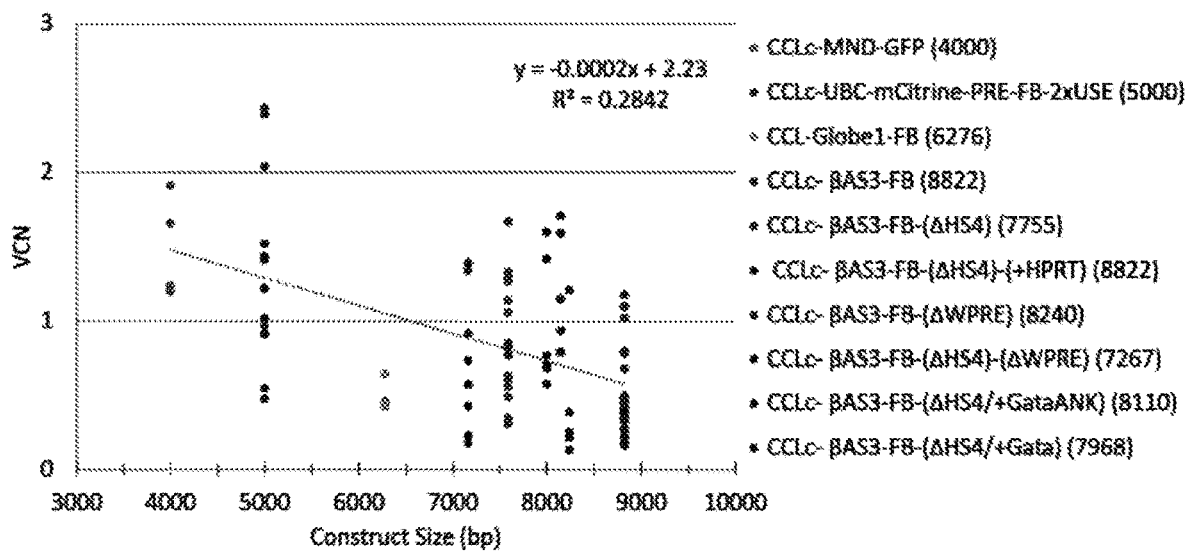
FIG. 6B shows the expression levels (vector copy number (VCN) plotted as a functions of construct size for these different lentiviral constructs FIG. 7 illustrates "open chromatin" track sets, that combine DNaseI hypersensitivity, formaldehyde-assisted isolation of regulatory elements, and chromatin immunoprecipitation data to identify accessible chromatin regions, that was combined with the "transcription Factor ChIP-seq" and "histone modification" track sets used to generate correct boundaries for the LCR's HS core sequences.

FIG. 6A shows the raw titers plotted as a function of construct size for 15 different lentiviral constructs. FIG. 6B shows the expression levels (vector copy number (VCN)) plotted as a function of construct size for these different lentiviral constructs.

As can be seen, reduction of vector length through removal of discrete sequences improves titer and gene transfer. However certain elements must be preserved to maintain erythroid specific expression. The challenge was to identify the best combination of elements that offer high-level and erythroid specific expression within the smallest footprint.

Figure 7:
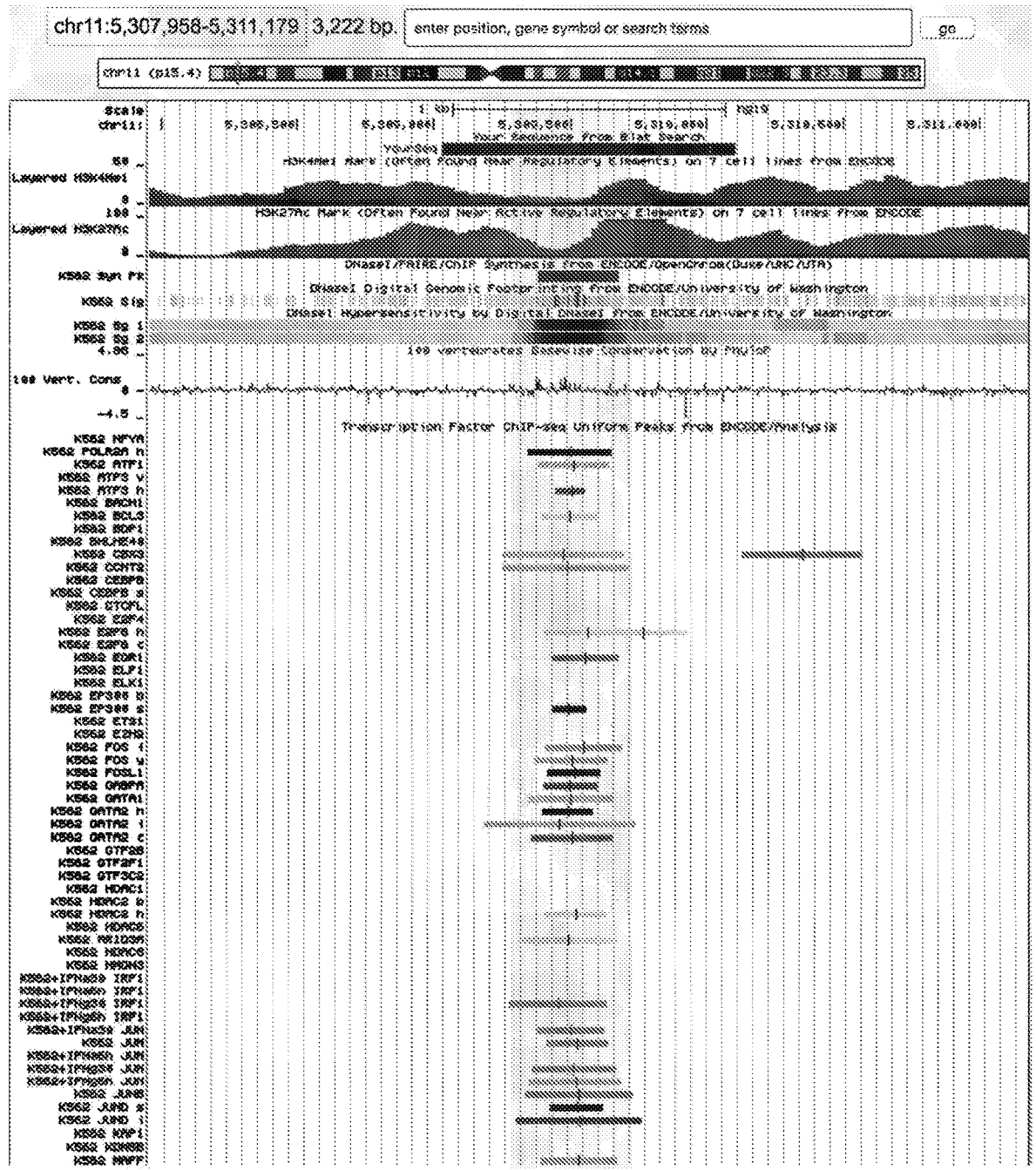
Figure 8A:
FIGS. 8A and 8B schematically illustrates novel defined LCR HS core sequences (HS2(~420 bp), HS3(~340 bp), HS4(~410 bp)) that were then used to replace the putative LCR HS sequences present within the "mini-LCR" (~3.6 kb reduced to ~1.2 kb) to produce an "optimized mini-LCR" (CoreLCR-Opti).
Figure 8B:
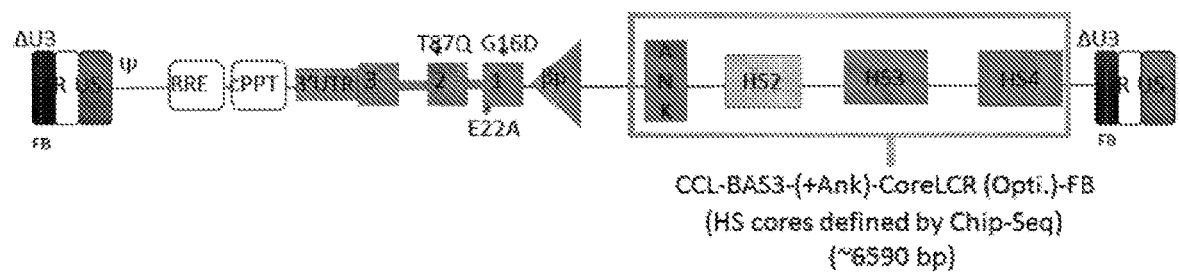

We engineered optimized derivatives of CCLc-βAS3-FB, that are capable of driving lineage-restricted expression of an anti-sickling β-globin like gene (βAS3) (see, e.g., FIGS. 8B, 15A, 16A). Creation of the "optimized mini-LCR", present within the derivative constructs, occurred through redefining the putative boundaries of the LCR's HS core sequences using published genomic data available through ENCODE (Accessible via the UCSC Genome Browser). Specifically, the "Open Chromatin" track sets, which combine DNaseI hypersensitivity, Formaldehyde-Assisted Isolation of Regulatory Elements, and chromatin immunoprecipitation data to identify accessible chromatin regions, was combined with the "transcription Factor ChIP-seq" and "histone modification" track sets to generate correct boundaries for the LCR's HS core sequences (see, e.g., FIG. 7).

These novel defined LCR HS core sequences (HS2(~420 bp), HS3(~340 bp), HS4(~410 bp)) were then used to replace the putative LCR HS sequences present within the "mini-LCR" (~3.6 kb reduced to ~1.2 kb) to produce an "optimized mini-LCR" (see, e.g., FIG. 8A).

Figure 10:
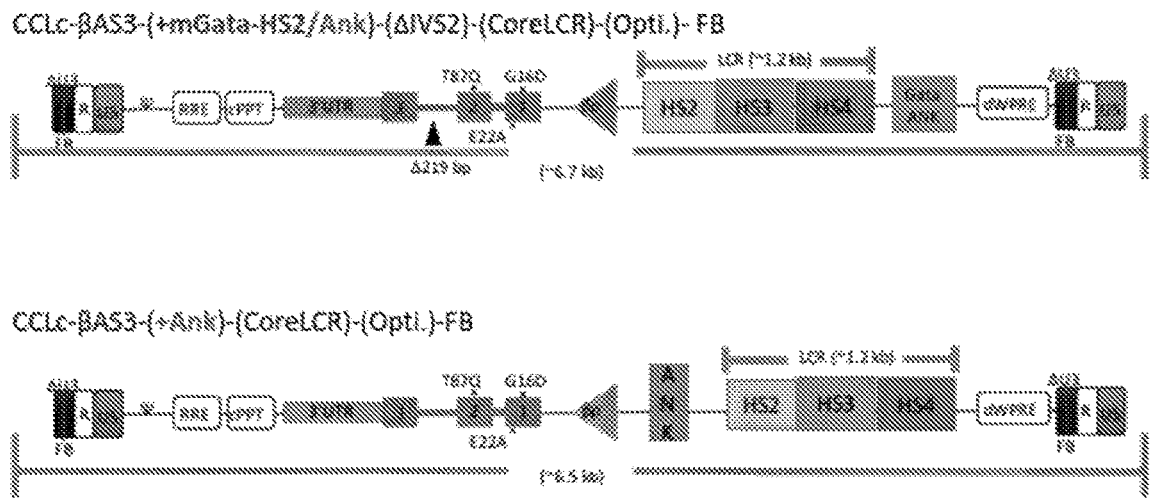
FIG. 10 schematically illustrates CCLc-βAS3-(mGATA-HS2/ANK)-(ΔIVS2)-(CoreLCR)-(Opti.)-FB and CCLc-βAS3-(+Ank)-(CoreLCR)-(Opti.)-FB vectors.

In addition, we added elements to the "optimized mini-LCR" known to facilitate position independent expression of β-globin such as the murine GATA1-H52 (~220 bp) and/or the human Ankyrin insulator (~150 bp) elements (see, e.g., FIGS. 8B, and 10).

Figure 9:
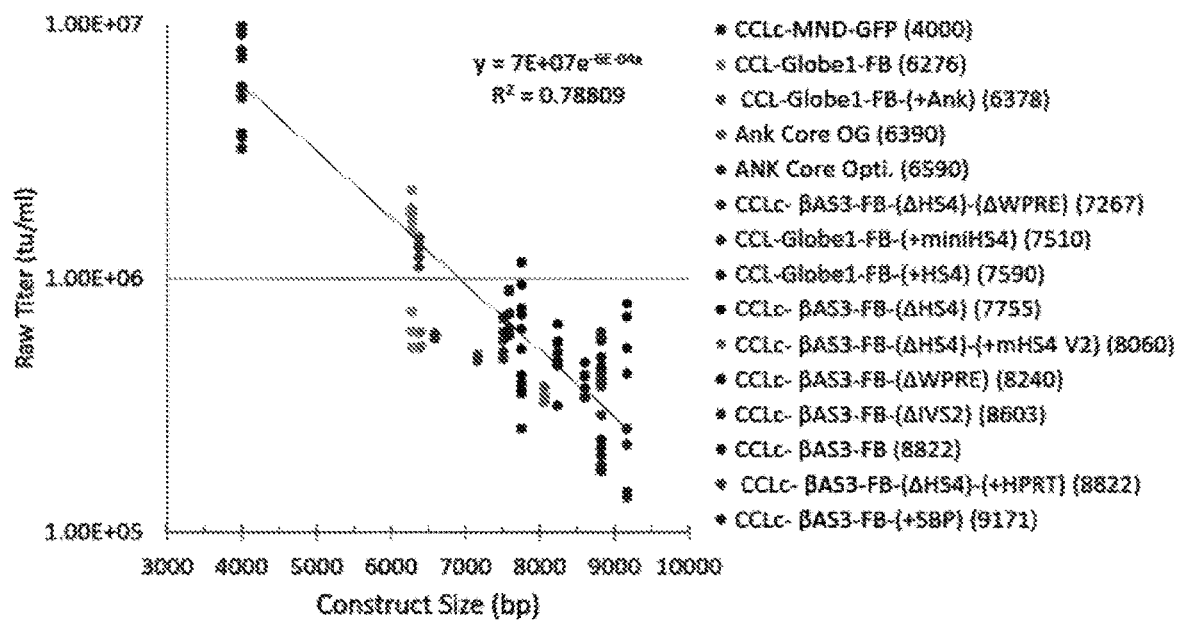
FIG. 9 illustrates the relationship between raw titer and construct size.

Based on the vector length-titer relationship shown in FIG. 9, it was predicted that a reduction in vector length of about 2-3 kb should increase titer about 3-fold.

These vectors, rationally-designed for reduced sizes of the LCR fragments and added transcriptional enhancing elements may be produced at higher titers than the original β-globin lentiviral vector and have improved gene transfer to human HSC while retaining strong erythroid-specific gene expression.

FIG. 15A illustrates the pCCLC-βAS3-FB(+CoreLCR w-Ank-R) optimized vector ((10528 bp), while FIG. 15B illustrates the nucleic acid sequence of the vector. Regions of interest in this vector are shown below in Table 2.

TABLE 2

Locations of various regions of interest in the pCCLC-βAS3-FB(+CoreLCR w-Ank-R) optimized vector ((10528 bp).

| Name | Location (Range) (SEQ ID NO: 1, and FIG. 15B) |
|---|---|
| CMV | 594 to 1122 |
| R | 1123 to 1218 |
| U5 | 1219 to 1302 |
| PSI | 1355 to 1492 |
| cPPT | 2694 to 2883 |
| RRE | 1957 to 2156 |
| 3' UTR and enhancers | 2975 to 3794 |
| R | 7532 to 7627 |
| U3-FB | 7402 to 7531 |
| SV40 ori | 7945 to 8084 |
| U5 | 7628 to 7711 |
| AMPr | 8891 to 9748 |
| HS2 | 5484 to 5908 |
| HS3 | 5909 to 6252 |
| HS4 | 6253 to 6662 |
| Ank | 5325 to 5483 |
| CORE Opti | 5484 to 6662 |
| Promoter | 5027 to 5291 |
| AS3 Globin | 3795 to 5026 |
| WPRE | 6691 to 7316 |

FIG. 16A illustrates the pCCL-3AS3-(+mGATA-HS2-Ank-dIVS2-CoreLCRopti)-FB optimized vector (10483 bp), while FIG. 16B illustrates the nucleic acid sequence of the vector. Regions of interest in this vector are shown below in Table 2.

TABLE 3

Locations of various regions of interest in the pCCL-βAS3-(+mGATA-HS2-Ank-dIVS2-CoreLCRopti)-FB optimized vector.

| Name | Location (Range) (SEQ ID NO: 2, and FIG. 16B) |
|---|---|
| CMV | 594 to 1122 |
| R | 1123 to 1218 |
| U5 | 1219 to 1302 |
| PSI | 1355 to 1492 |
| R | 7487 to 7582 |
| U3-FB | 7357 to 7486 |
| U5 | 7583 to 7666 |
| SV40 ori | 7900 to 8039 |
| AMPr | 8846 to 9703 |
| ori | 10080 to 10361 |
| cPPT | 2694 to 2883 |
| RRE | 1957 to 2156 |
| 3' UTR and enhancers | 2975 to 3794 |
| mGATA1 HS2 | 6256 to 6457 |
| Ank | 6458 to 6616 |

TABLE 3-continued

Locations of various regions of interest in the pCCL-βAS3-(+mGATA-HS2-Ank-dIVS2-CoreLCRopti)-FB optimized vector.

| Name | Location (Range) (SEQ ID NO: 2, and FIG. 16B) |
|---|---|
| HS2 | 5077 to 5501 |
| HS3 | 5502 to 5845 |
| HS4 | 5846 to 6255 |
| AS3 Globin | 3795 to 4807 |
| dIVS2 | 4057 to 4312 |
| Promoter | 4808 to 5055 |
| WPRE | 6646 to 7271 |
| CORE Opti | 5077 to 6255 |

Figure 11:
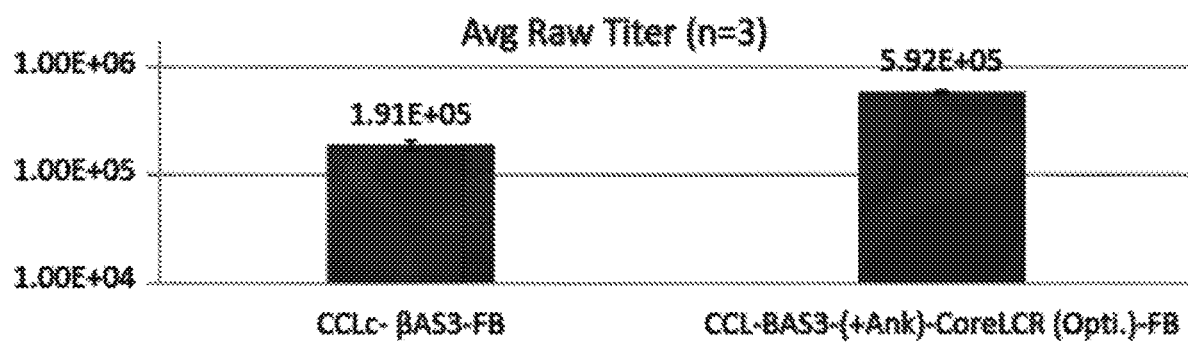
FIG. 11 shows raw titer produced by CCLc-βAS3-FB and CCLc-βAS3-(+Ank)-CoreLCR(Opti)-FB constructs.

Raw titer data for CCLc-βAS3-(+Ank)-(CoreLCR)-(Opti.)-FB are shown in Table 4 and FIG. 11.

TABLE 4

Raw titer data.

| Sample | Titer (tu/ml) Avg ± Std. Dev. n = 3 | Avg Fold Diff ± Std. Dev. |
|---|---|---|
| CCLc-MND-GFP | $3.51 \times 10^6 \pm 2.45 \times 10^5$ | 18.34 ± 1.28 |
| CCLc-βAS3-FB | $1.91 \times 10^5 \pm 2.13 \times 10^4$ | 1.00 ± 0.11 |
| CCL-BAS3-(+Ank)-CoreLCR(OPti.)-FB | $5.92 \times 10^5 \pm 1.37 \times 10^4$ | 3.09 ± 0.07 |

Figure 12:
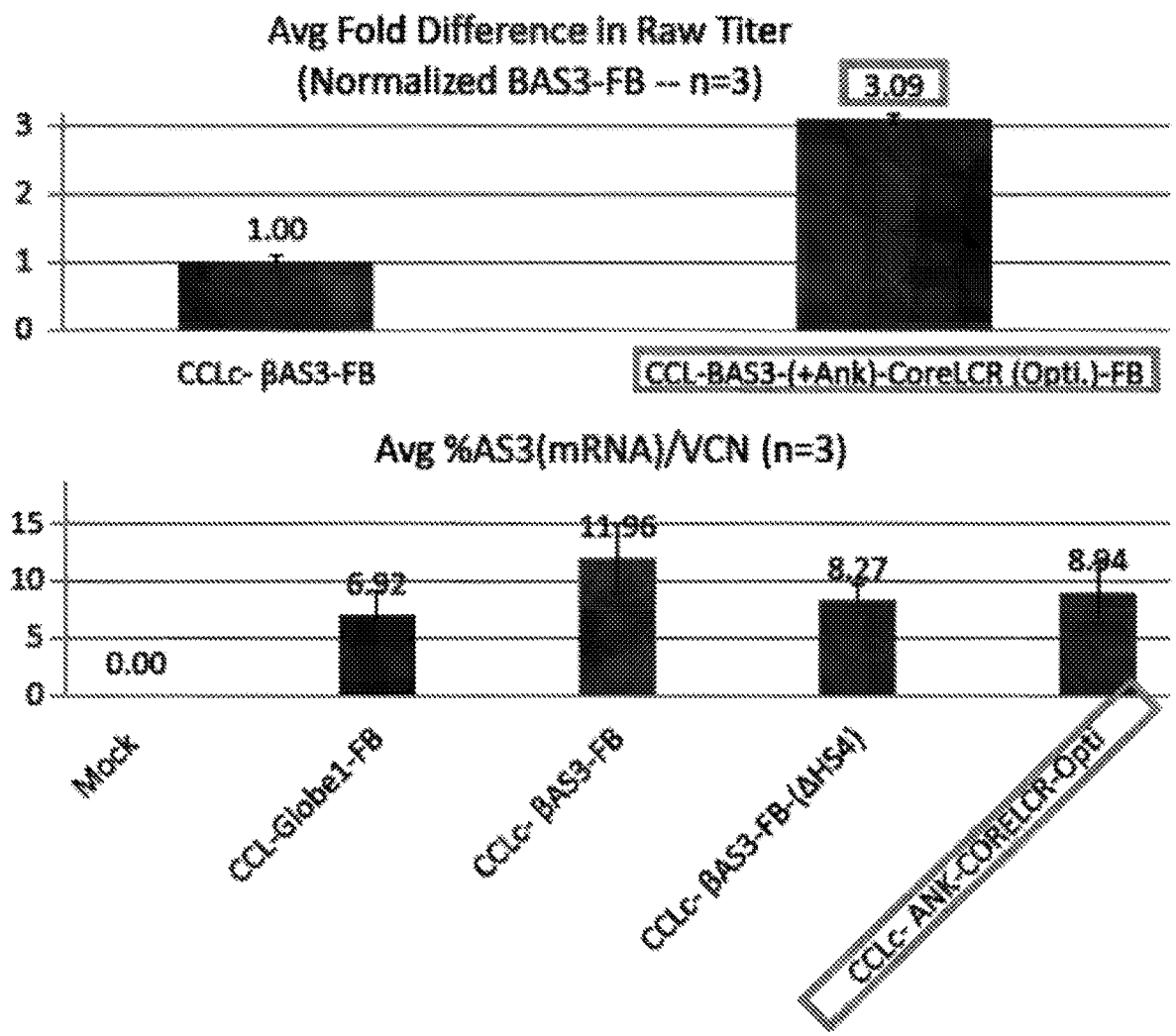
FIG. 12 (top panel) shows average fold difference in raw titer produced by CCLc-βAS3-FB and CCLc-βAS3-(+Ank)-CoreLCR(Opti)-FB constructs.

Average raw titer data CCLc-βAS3-(+Ank)-(CoreLCR)-(Opti.)-FB normalized to BAS3-FB are shown in FIG. 12, top panel, while expression data are shown in FIG. 12, bottom panel. CCL-GLOBE-FB expression (Avg % AS3) significantly lower than CCLc-BAS3-FB. CCLc-ANK-CORELCR-Opti expression not significantly different than CCLc-BAS3-FB.

Figure 13:
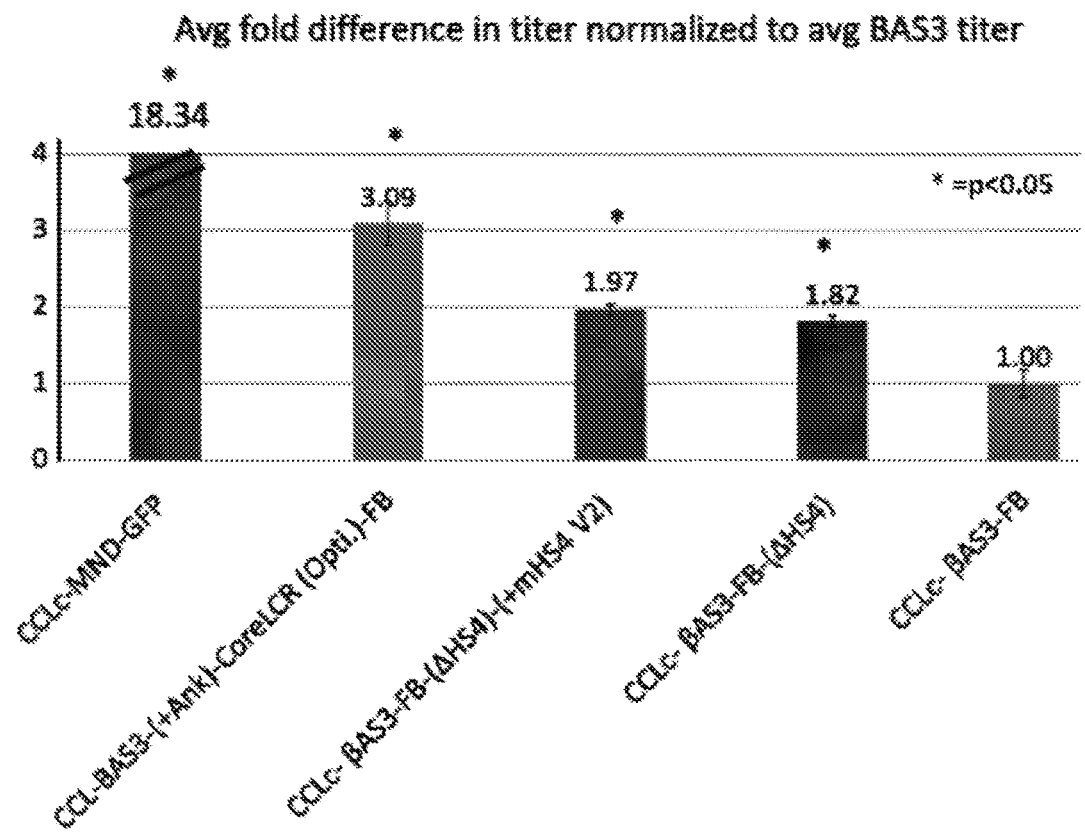
FIG. 13 shows the effect of replacing LCR with ANK and HS2, HS3, HS4 optimized core elements.
Figure 14:
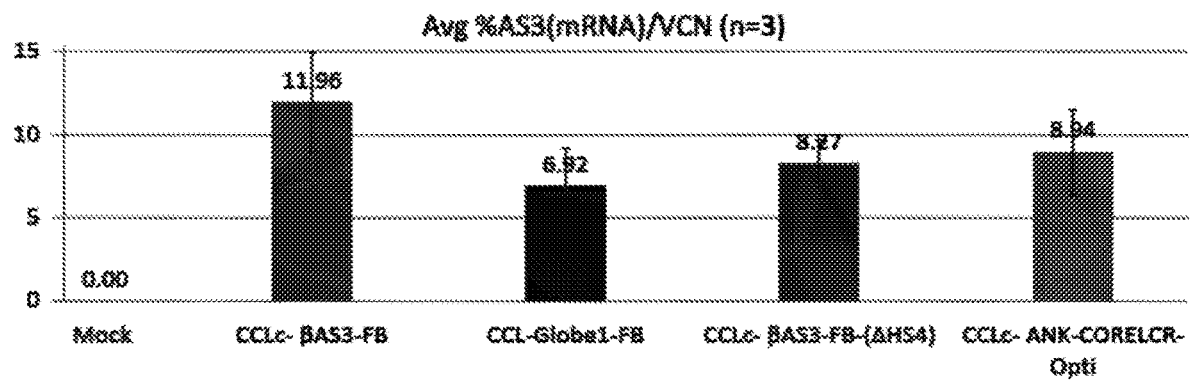
FIG. 14 shows the effect of replacing LCR with ANK and HS2, HS3, HS4 core elements.

FIG. 13 shows that replacing the LCR with ANK and optimized HS2, HS3, and HS4 core element increased titer by three fold. FIG. 14 and Table 5 shows that replacing the LCR with ANK and only core elements achieves levels of expression similar to CCLc-βAS3-FB(ΔHS4).

TABLE 5

Construct expression levels.

| | Mock | CCL-Globe1-FB | CCLc-βAS3-FB- | CCKc-βAS3-FB-(ΔHS4) | CCLc-ANK-CoreLCR-Opti |
|---|---|---|---|---|---|
| % BAS3(mRNA)/VCN | 0.0 | 6.9 | 12 | 8.3 | 8.9 |
| StdDev | 0.0 | 2.2 | 3 | 1.4 | 2.6 |

Example 2

Optimized Derivatives of CCLc-βAS3-FB

We have engineered optimized derivatives of "CCLc-βAS3-FB", which are capable of driving lineage-restricted expression of an anti-sickling β-globin like gene (βAS3). Creation of the "optimized mini-LCR", present within the derivative constructs, occurred through redefining the putative boundaries of the LCR's HS core sequences using published genomic data available through ENCODE (Accessible via the UCSC Genome Browser). Specifically, the "Open Chromatin" track sets, which combine DNaseI hypersensitivity, Formaldehyde-Assisted Isolation of Regulatory Elements, and chromatin immunoprecipitation data to identify accessible chromatin regions, was combined with the "transcription Factor ChIP-seq" and "histone modification" track sets to generate correct boundaries for the LCR's HS core sequences.

Figure 17:
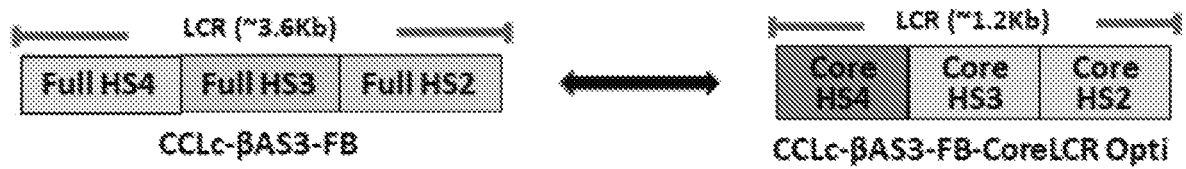
FIG. 17 schematically illustrates novel defined LCR HS core sequences (HS2 (~420 bp), HS3(~340 bp), and HS4 (~410 bp)) that were used to replace the putative LCR HS sequences present within the "mini-LCR" (~3.6 Kb reduced to ~1.2 Kb) to produce an "optimized mini-LCR".

These novel defined LCR HS core sequences (HS2(~420 bp), HS3(~340 bp), HS4(~410 bp)) were then used to replace the putative LCR HS sequences present within the "mini-LCR" (~3.6 Kb reduced to ~1.2 Kb) to produce an "optimized mini-LCR" (see, e.g., FIG. 17).

Figure 18A:
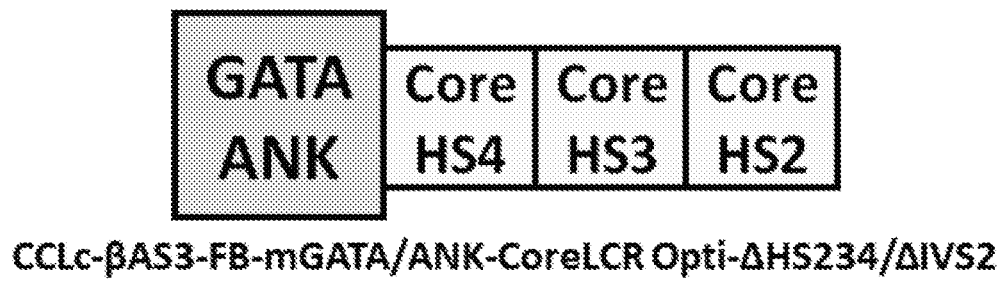
FIGS. 18A-18C, illustrate various constructs adding element to the "optimized mini-LCR".
Figure 18B:
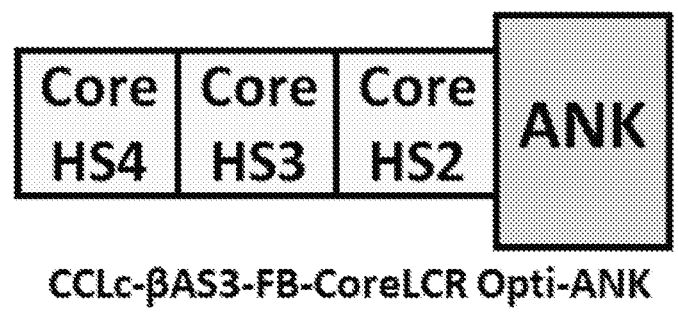

In addition, we added elements to the "optimized mini-LCR" known to facilitate position independent expression of β-globin such as the murine mGATA1-H52 (~220 bp) and/or the Human Ankyrin Insulator (~150 bp) elements (see, e.g., FIGS. 18A and 18B).

Figure 18C:
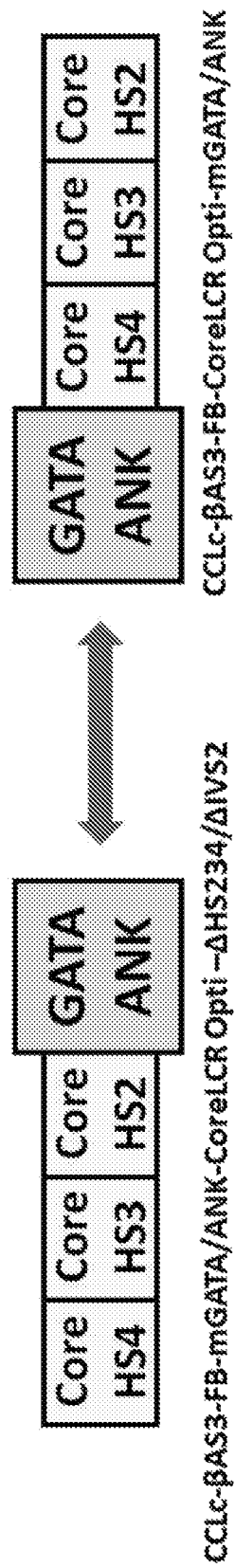

We also tested the mGATA1-H52 and the human ankyrin insulator elements in alternative configurations in combination with the "optimized mini-LCR" (see, e.g., FIG. 18C).

Figure 19:
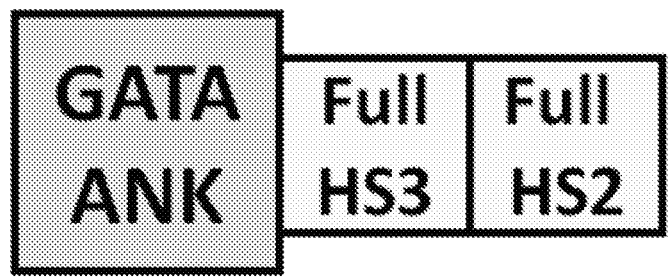
FIG. 19 schematically illustrates mGATA1-HS2 and human ankyrin insulator elements used in a construct with full-length erythroid enhancers (HS2 and HS3).

We also tested the murine mGATA1-H52 and the human ankyrin insulator elements with full-length erythroid enhancers (HS2 and HS3) (see, e.g., FIG. 19).

These vectors, rationally-designed for reduced sizes of the LCR fragments and added transcriptional enhancing elements may be produced at higher titers than the original β-globin lentiviral vector ("CCLc-βAS3-FB") and possess improved gene transfer to human HSPCs while retaining erythroid-specific gene expression.

Figure 20:
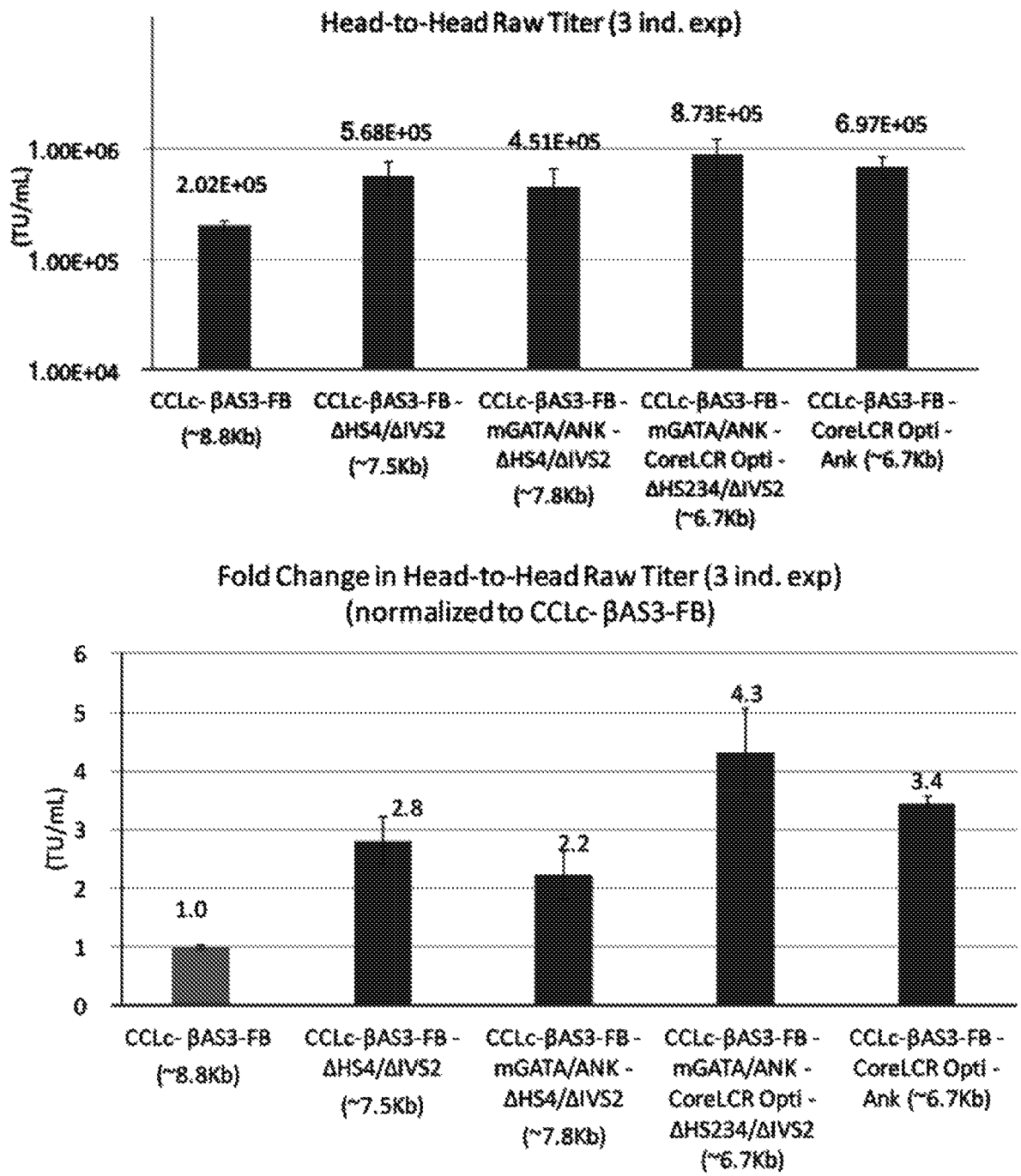
FIG. 20 illustrates head-to-head raw titer produced using different constructs.

As illustrated in FIG. 20, we observed that deletion of full-length HS4 (leaving HS 2 and 3 in place, as in GLOBE vectors) and partial deletion of intron-2 sequences from "CCLc-βAS3-FB" increased titer 2.8-fold (see "CCLc-βAS3-FB-ΔHS4/ΔIVS2"). Addition of mGATA/ANK element to "CCLc-βAS3-FB-ΔHS4/ΔIVS2" did not overtly negate gains in titer achieved from removal of sequence from "CCLc-βAS3-FB" (see "CCLc-βAS3-FB-mGATA/ANK-ΔHS4/ΔIVS2"). Replacement of full-length HS2 and HS3 elements in "CCLc-βAS3-FB-mGATA/ANK-ΔHS4/ΔIVS2" with "CoreLCR Opti" increased raw titer 4.3-fold when compared to parental (see "CCLc-βAS3-FB-mGATA/ANK-CoreLCR Opti-ΔHS234/ΔIVS2"). Addition of intron-2 sequence and replacement of mGATA/ANK with only ANK (and placed in an alternative location) did not overtly negate gains in titer achieved from size reduction (see "CCLc-βAS3-FB-CoreLCR Opti-ANK"). These data show that improved raw titer can be achieved through deletion of full-length HS elements and inclusion of core elements with mGATA-HS2 and/or ANK.

Figure 21:
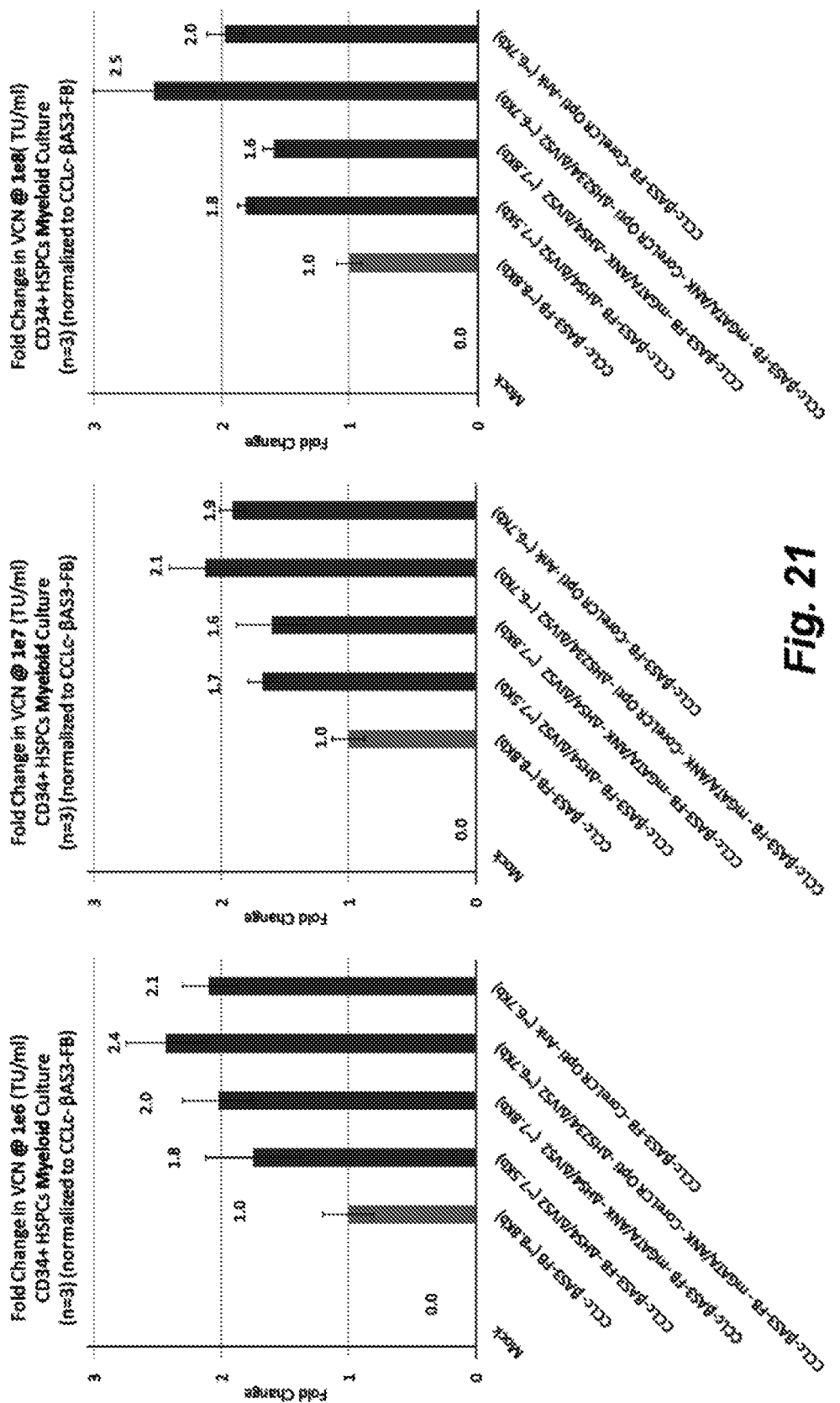
FIG. 21 illustrates the results of gene transfer studies. Escalating viral dose-CD34+BM HSPCs cultured under myeloid conditions.

Myeloid gene transfer studies typically reflect the level of gene marking seen in Human bone marrow following gene therapy. As shown in FIG. 21, we observed that deletion of full-length HS4 and partial deletion of intron-2 sequences from "CCLc-βAS3-FB" increased gene transfer ~1.8, ~1.7, or ~1.8-fold when CD34+HSPCs were transduced at 1e6, 1e7, or 1e8 (TU/ml), respectively (see "CCLc-βAS3-FB-ΔHS4/ΔIVS2"). Addition of mGATA/ANK element to "CCLc-βAS3-FB-ΔHS4/ΔIVS2" increased gene transfer ~2.0, ~1.6, or ~1.6-fold when CD34+ HSPCs were transduced at 1e6, 1e7, or 1e8 (TU/ml), respectively (see "CCLc-βAS3-FB-mGATA/ANK-ΔHS4/ΔIVS2"). Replacement of full-length HS2 and HS3 elements present within "CCLc-βAS3-FB-mGATA/ANK-ΔHS4/ΔIVS2" with "CoreLCR Opti" increased gene transfer ~2.4, ~2.1, or ~2.5-fold when CD34+ HSPCs were transduced at 1×106, 1×107, or 1×108 (TU/ml), respectively (see "CCLc-βAS3-FB-mGATA/

ANK-CoreLCR Opti-ΔHS234/ΔIVS2"). Addition of intron-2 sequence and replacement of mGATA/ANK with only ANK (and placed in an alternative location) increased gene transfer ~2.1, ~1.9, or ~2.0-fold when CD34+ HSPCs were transduced at $1\times10^6$, $1\times10^7$, or $1\times10^8$ (TU/ml), respectively (see "CCLc-βAS3-FB-CoreLCR Opti-ANK"). These data show that improved gene transfer to CD34+ HSPCs can be achieved through deletion of full-length HS elements and inclusion of "CoreLCR Opti" and mGATA-HS2 and/or ANK.

Figure 22:
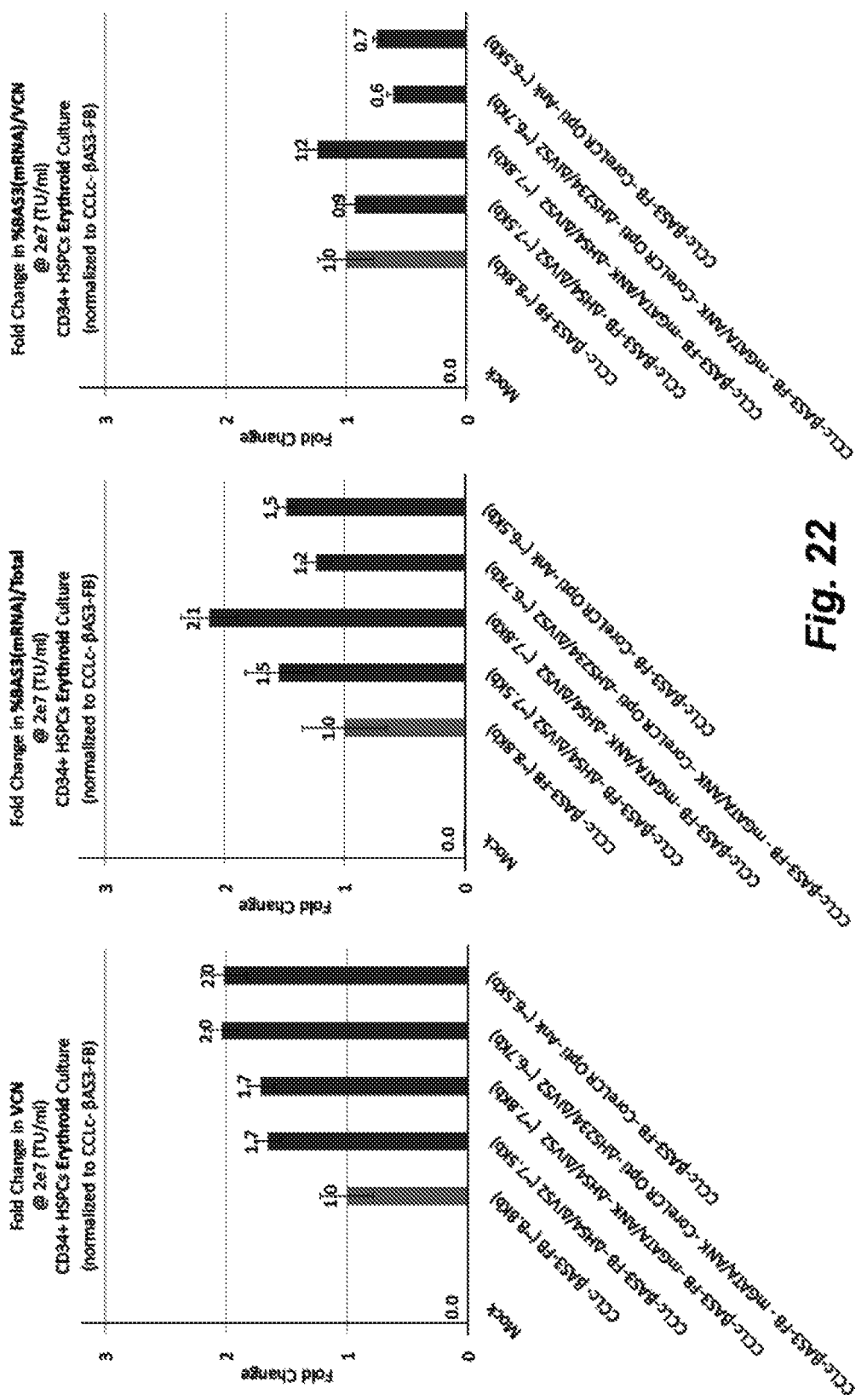
FIG. 22 illustrates the results of erythroid expression studies. Constant viral dose of $2 \times 10^7$(TU/ml)-CD34+BM HSPCs cultured under erythroid conditions.

Erythroid expression studies offer insight into the total level of expression that can be achieved globally (% transgene/(% transgene+total β-globin "like" transcripts)) and can be further normalized to vector copy number to estimate the level of expression per vector insertion. As shown in FIG. 22, we observed that deletion of full-length HS4 and partial deletion of intron-2 sequences from "CCLc-βAS3-FB" increased total transgene expression by ~1.5-fold by way of increased gene transfer to target cells. When expression was normalized to VCN, total transgene expression was ~0.9-fold that of the parental vector (see "CCLc-βAS3-FB-ΔHS4/ΔIVS2"). Addition of mGATA/ANK element to "CCLc-βAS3-FB-ΔHS4/ΔIVS2" increased total expression by ~2-fold when compared to parental. The increase in total expression results from synergy between greater gene transfer to target cells and higher expression per VCN when compared to parental (see "CCLc-βAS3-FB-mGATA/ANK-ΔHS4/ΔIVS2"). Replacement of full-length HS2 and HS3 elements present within "CCLc-βAS3-FB-mGATA/ANK-ΔHS4/ΔIVS2" with "CoreLCR Opti" resulted in comparable total transgene expression when compared to "CCLc-βAS3-FB" by way of increased gene transfer to target cells. When expression was normalized to VCN, total transgene expression was ~0.6-fold that of the parental vector (see "CCLc-βAS3-FB-mGATA/ANK-CoreLCR Opti-ΔHS234/ΔIVS2").

Figure 23:
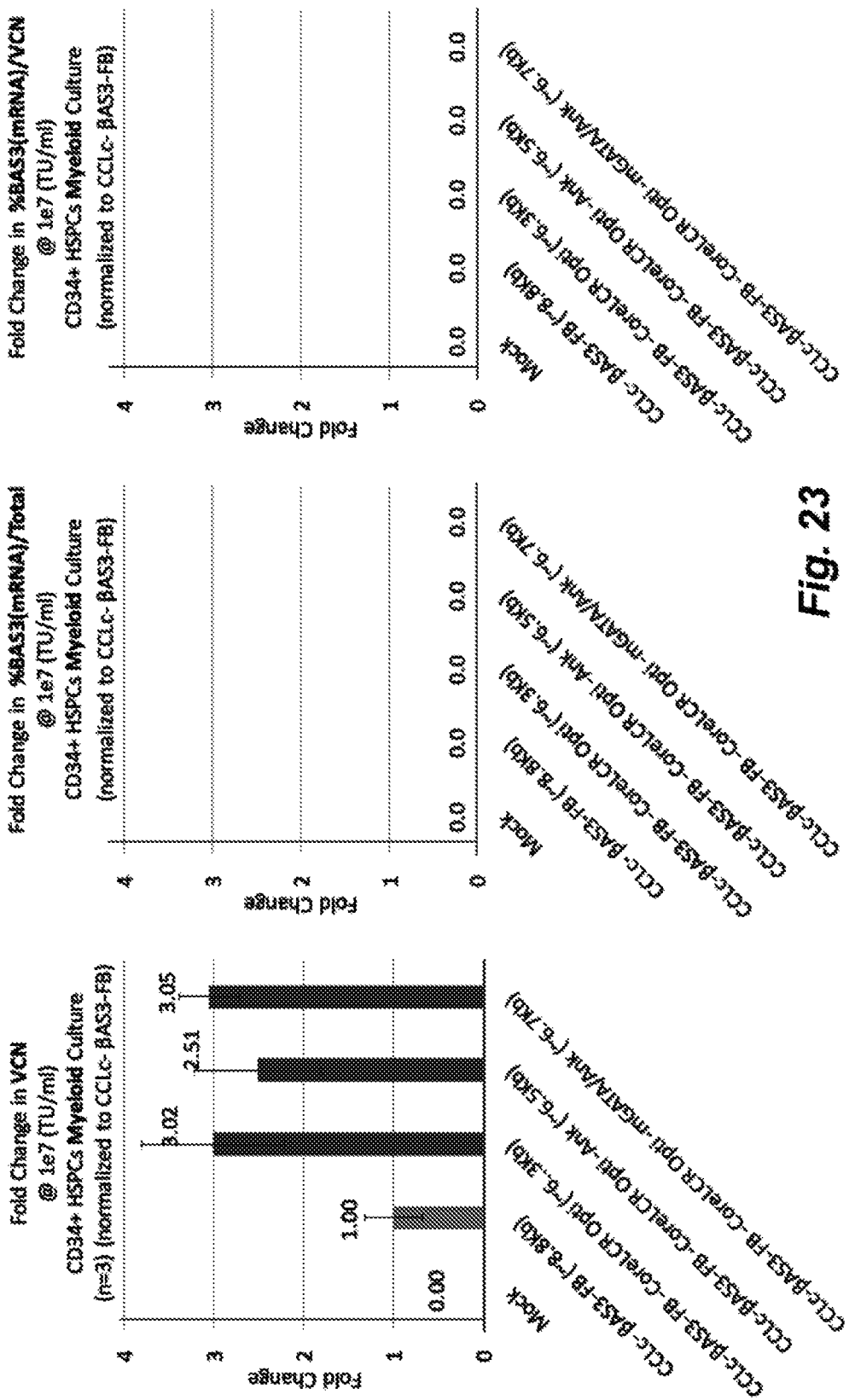
FIG. 23 illustrates the results of gene transfer studies to determine effect of placing mGATA/ANK in alternative configurations. Constant viral dose of $1 \times 10^7$(TU/ml)-CD34+ BM HSPCs cultured under myeloid conditions.

As illustrated in FIG. 23, when HS4, HS3, and HS2 were replaced with "CoreLCR Opti" alone, gene transfer was improved by ~3-fold when CD34+ HSPCs were transduced at $1\times10^7$ (TU/ml) (see "CCLc-βAS3-FB-CoreLCR Opti"). The addition of ANK to "CoreLCR Opti" did not overtly negate improvements in gene transfer gained by removing HS4, HS3, and HS2 elements (see "CCLc-βAS3-FB-CoreLCR Opti-Ank"). The addition of mGATA/ANK to "CoreLCR Opti" (now, same location as ANK in "CCLc-βAS3-FB-CoreLCR Opti-ANK"), resulted in a ~3-fold improvement in gene transfer (see "CCLc-βAS3-FB-CoreLCR Opti-mGATA/ANK"). Replacement of HS4, HS3, and HS2 with any "CoreLCR Opti" variant did not result in any detectable expression in CD34+ HSPCs cultured under myeloid culture conditions. When this finding is taken together with other expression data supplied herein, it implies that all "CoreLCR Opti" variants retain lineage restricted expression. Addition of intron-2 sequence and replacement of mGATA/ANK with only ANK (and placed in an alternative location) resulted in ~1.5-fold increased total transgene expression by way of increased gene transfer to target cells (see "CCLc-βAS3-FB-CoreLCR Opti-ANK"). These data show that, 1). Addition of mGATA/ANK element to "CCLc-βAS3-FB-ΔHS4/ΔIVS2" improved enhancer output, 2). "CCLc-βAS3-FB-mGATA/ANK-CoreLCR Opti-ΔHS234/ΔIVS2" or "CCLc-βAS3-FB-CoreLCR Opti-ANK" provide similar or superior total transgene expression when compared to parental.

Figure 24:
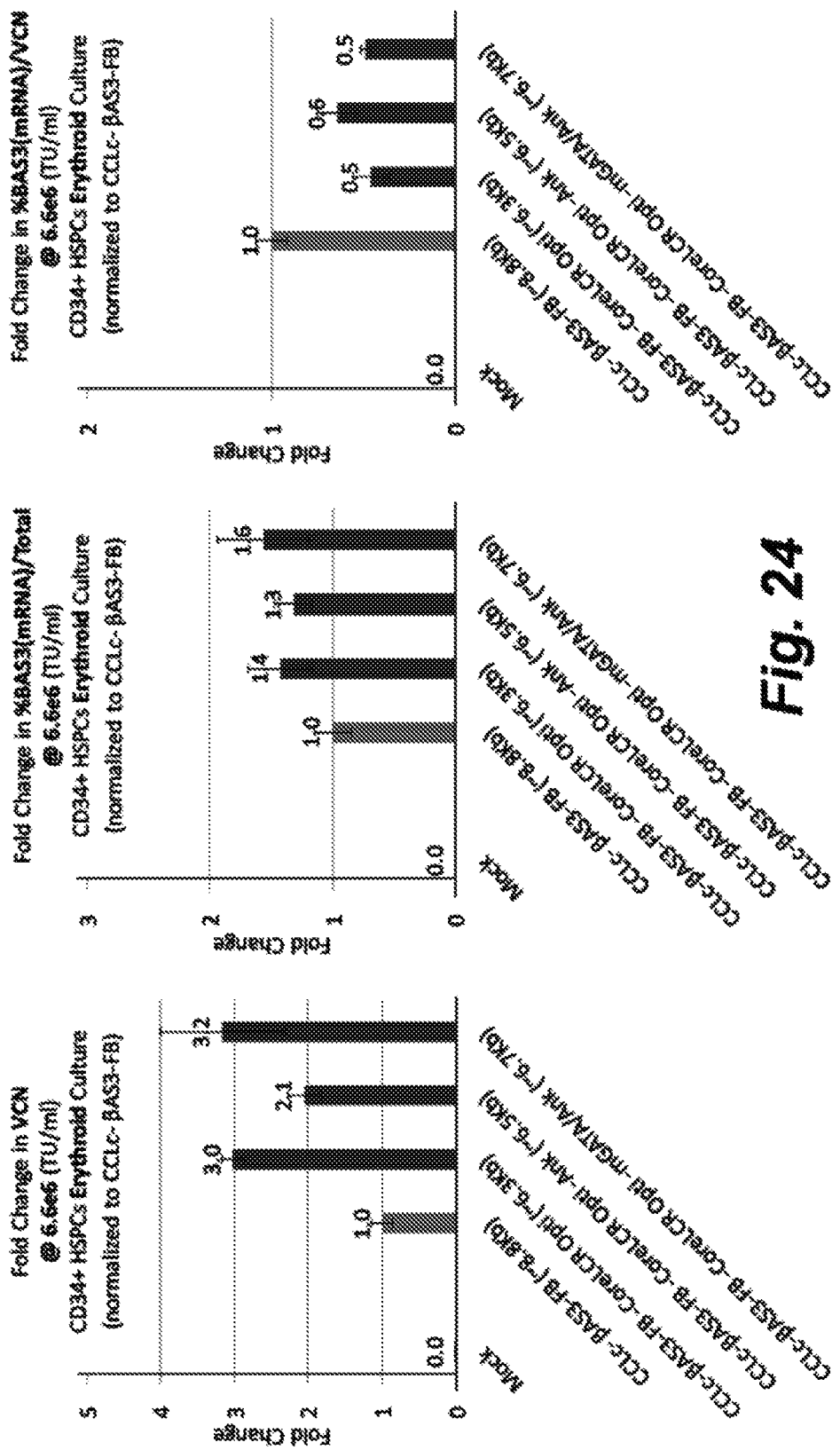
FIG. 24 illustrates the results of expression studies to determine effect of placing mGATA/ANK in alternative configurations. Constant viral dose of $6.6 \times 10^6$ or $1 \times 10^7$(TU/ml)-CD34+BM HSPCs cultured under erythroid conditions.

As shown in FIG. 24, when HS4, HS3, and HS2 were replaced with "CoreLCR Opti" alone or in combination with mGATA/ANK or only ANK, total expression was comparable or superior to "CCLc-βAS3-FB" by way of increased gene transfer to target cells. This observation can be made at the $6.6\times10^6$ or $1\times10^7$ (TU/ml) transduction conditions. When mGATA/ANK was placed adjacent to HS2 (now, same location as ANK in "CCLc-βAS3-FB-CoreLCR Opti-ANK"), increased total comparable or superior total transgene expression can be observed. This observation, when taken together with those stated herein, suggest that mGATA/ANK can work in alternate configurations (compare "CCLc-βAS3-FB-CoreLCR Opti-mGATA/ANK" to "CCLc-βAS3-FB-mGATA/ANK-CoreLCR Opti-ΔHS234/ΔIVS2").

It is understood that the examples and embodiments described herein are for illustrative purposes only and that various modifications or changes in light thereof will be suggested to persons skilled in the art and are to be included within the spirit and purview of this application and scope of the appended claims. All publications, patents, and patent applications cited herein are hereby incorporated by reference in their entirety for all purposes.

What is claimed is:

1. A recombinant lentiviral vector (LV) comprising:
an expression cassette comprising a nucleic acid construct comprising:
a human β-globin locus control region consisting of a hypersensitive site (HS) core sequence consisting of:
an HS2 core sequence that consists of a nucleic acid sequence ranging from nucleotide 5484 to 5908 of SEQ ID NO: 1;
an HS3 core sequence that consists of a nucleic acid sequence ranging from nucleotide 5909 to 6252 of SEQ ID NO: 1; and
an HS4 core sequence that consists of a nucleic acid sequence ranging from nucleotide 6253 to 6662 of SEQ ID NO: 1;
and a recombinant human beta globin gene encoding a beta globin polypeptide, wherein said LV is a TAT-independent and self-inactivating (SIN) lentiviral vector.

2. The vector of claim 1, wherein said human beta globin gene comprises an anti-sickling human beta globin gene encoding an anti-sickling beta globin polypeptide.

3. The vector of claim 2, wherein said human beta globin gene comprises an anti-sickling human beta globin gene encoding an anti-sickling-beta globin polypeptide comprise one or more mutations selected from the group consisting of Gly16Asp, Glu22Ala and Thr87Gln.

4. The vector of claim 3, wherein said vector comprises:
an anti-sickling human β-globin gene comprising about 2.3 kb of recombinant human β-globin gene including exons and introns under the control of the human β-globin gene 5' promoter and the human β-globin 3' enhancer; and/or
a β-globin intron 2 with a 375 bp RsaI deletion from IVS2; and/or
a β-globin gene comprising an SspI (S) to RsaI (R) deletion (~220 bp).

5. The vector of claim 1, wherein said vector comprises a human Ankyrin insulator element.

6. The vector of claim 5, wherein said human ankyrin insulator is adjacent to HS4 or adjacent to HS2.

7. The vector of claim 1, wherein said vector comprises a murine GATA1-HS2.

8. The vector of claim 7, wherein said GATA1-HS2 is adjacent to HS2 or adjacent to HS4.

9. The vector of claim 1, wherein said vector comprises an insulator in the 3' LTR.

10. The vector of claim 1, wherein said vector comprises:
a Rev Responsive Element (RRE); and/or
a ψ region vector genome packaging signal; and/or
a CMV enhancer/promoter; and/or
a Rev Responsive Element (RRE); and/or
a central polypurine tract; and/or
a post-translational regulatory element.

11. The vector of claim 1, wherein said vector comprises the nucleic acid sequence of SEQ ID NO: 1.

12. A host cell transduced with a vector of claim 1.

* * * * *